United States Patent
Baraldi et al.

(10) Patent No.: US 7,855,209 B2
(45) Date of Patent: Dec. 21, 2010

(54) ALLOSTERIC MODULATORS OF THE $A_1$ ADENOSINE RECEPTOR

(75) Inventors: Pier Giovanni Baraldi, Ferrara (IT); Allan R. Moorman, Durham, NC (US); Romeo Romagnoli, Ferrara (IT)

(73) Assignee: King Pharmaceuticals Research and Development, Inc., Cary, NC (US)

( * ) Notice: Subject to any disclaimer, the term of this patent is extended or adjusted under 35 U.S.C. 154(b) by 339 days.

(21) Appl. No.: 11/938,465

(22) Filed: Nov. 12, 2007

(65) Prior Publication Data

US 2008/0125438 A1    May 29, 2008

Related U.S. Application Data

(60) Provisional application No. 60/858,505, filed on Nov. 13, 2006.

(51) Int. Cl.
*A61K 31/497* (2006.01)
*C07D 403/06* (2006.01)

(52) U.S. Cl. .................. 514/252.13; 544/359

(58) Field of Classification Search ............ 514/252.13; 544/359
See application file for complete search history.

(56) References Cited

U.S. PATENT DOCUMENTS

| | | | | |
|---|---|---|---|---|
| 5,332,732 | A | 7/1994 | Scott et al. | 514/212 |
| 5,750,728 | A | 5/1998 | Wagner et al. | 549/57 |
| 5,939,432 | A | 8/1999 | Baraldi | 514/301 |
| 6,177,444 | B1 | 1/2001 | Baraldi | 514/301 |
| 6,194,449 | B1 | 2/2001 | Baraldi | 514/447 |
| 6,323,214 | B1 | 11/2001 | Baraldi | 514/301 |
| 6,713,638 | B2 | 3/2004 | Linden et al. | 549/57 |
| 6,727,258 | B2 | 4/2004 | Baraldi | 514/260.1 |
| 7,019,027 | B2 | 3/2006 | Linden et al. | 514/447 |
| 7,112,607 | B2 | 9/2006 | Baraldi | 514/443 |
| 2008/0119460 | A1* | 5/2008 | Baraldi et al. | 514/218 |

OTHER PUBLICATIONS

Baraldi et al., "Synthesis and Biological Effects of Novel 2-Amino-3-naphthoylthiophenes as Allosteric Enhancers of the $A_1$ Adenosine Receptor", *J. Med. Chem.* 2003, 46, 794-809.
Baraldi et al., "Synthesis of 2-amino-3-heteroaroylthiophenes and evaluation of their activity as potential allosteric enhancers at the human $A_1$ receptor", *European J. Med. Chem.* 2004, 39, 855-865.
Romagnoli et al., "Synthesis and Biological Evaluation of Allosteric $A_1$-Adenosine Receptor Modulators Structurally Related to (2-Amino-4,5,6,7-tetrahydro-benzo[b]thiophen-3-yl)-(4-chlorophenyl)-methanone, a Potent Compound Useful to Reduce Neuropathic Pain", *Med. Chem. Res.* 2005, 14(3), 125-142.
Romagnoli et al., "Synthesis and Biological Evaluation of 2-Amino-3-(3',4',5'-trimethoxybenzoyl)-5-aryl Thiophenes as a New Class of Potent Antitubuln Agents", *J. Med. Chem.* 2006, 49, 3906-3915.
Gutiérres-de-Terán et al., "Novel Approaches for Modeling of the $A_1$ Adenosine Receptor and Its Agonist Binding Site", PROTEINS: Structure, Function, and Bioinformatics, 2004, 54, 705-715.

* cited by examiner

*Primary Examiner*—James O Wilson
*Assistant Examiner*—Ebenezer Sackey
(74) *Attorney, Agent, or Firm*—Paivi Kukkola

(57) ABSTRACT

The present invention provides compounds of formula (I)

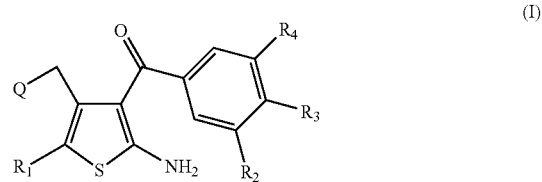

wherein $R_1$, $R_2$, $R_3$, $R_4$ and Q have a meaning as defined herein in the specification. The compounds of formula (I) are allosteric modulators of the $A_1$ adenosine receptor and, thus, may be employed for the treatment of conditions mediated by the $A_1$ adenosine receptor. Accordingly, the compounds of formula (I) may be employed for treatment of pain, in particular, chronic pain such as neuropathic pain; cardiac disease or disorder such as cardiac disarrhythmias, e.g., peroxysmal supraventricular tachycardia, angina, myocardial infarction and stroke; neurological disease or injury; sleep disorder; epilepsy; and depression.

21 Claims, No Drawings

ALLOSTERIC MODULATORS OF THE A₁ ADENOSINE RECEPTOR

This application claims the benefit of U.S. Provisional Application No. 60/858,505 filed Nov. 13, 2006, the entire contents of which are incorporated herein by reference.

The present invention relates to 2-aminothiophene derivatives, pharmaceutical compositions containing them, and to methods of treating conditions mediated by the $A_1$ adenosine receptor including pain, in particular, chronic pain such as neuropathic pain, cardiac disease or disorder such as cardiac disarrhythmias, e.g., paroxysmal supraventricular tachycardia, angina, myocardial infarction and stroke, neurological disease or injury, sleep disorders, epilepsy and depression, by employing such compounds.

Accordingly, the present invention provides compounds of formula (I)

(I)

wherein
$R_1$ is hydrogen, alkyl, substituted alkyl, aryl, substituted aryl, cycloalkyl or substituted cycloalkyl;
$R_2$, $R_3$, and $R_4$ are, independently from each other, hydrogen, alkyl, substituted alkyl, aryl, substituted aryl, cycloalkyl, substituted cycloalkyl, halogen, hydroxyl, nitro, cyano, alkoxy or substituted alkoxy;
Q is selected from the group consisting of in which
$R_5$ is hydrogen, alkyl, substituted alkyl, aryl, substituted aryl, cycloalkyl, substituted cycloalkyl, heteroaryl, substituted heteroaryl, heteroaralkyl, substituted heteroaralkyl, acyl or substituted acyl;
$R_6$ and $R_7$ are, independently from each other, hydrogen, $C_1$-$C_3$ alkyl or $C_1$-$C_3$ substituted alkyl; or
$R_6$ and $R_7$, provided they are attached to the same carbon atom, combined are alkylene which together with the carbon atom to which they are attached form a 3- to 7-membered spirocyclic ring;
$R_8$, $R_9$, $R_{10}$, $R_{11}$, $R_{12}$ and $R_{13}$ are, independently from each other, hydrogen, $C_1$-$C_3$ alkyl or $C_1$-$C_3$ substituted alkyl;
X is N; or
X is C—H; or
X is C—$NR_{14}R_{15}$ wherein $R_{14}$ and $R_{15}$ are, independently from each other, hydrogen, $C_1$-$C_3$ alkyl, $C_1$-$C_3$ substituted alkyl, aryl or substituted aryl; or
X is C—$R_{16}$ wherein $R_{16}$ and $R_5$ combined are a carbonyl oxygen; or
X is C—$R_{16}$ wherein $R_{16}$ and $R_5$ combined are a divalent radical of the formula $$\leftarrow Y-CHR_{17}-(CH_2)_n-CHR_{18}-Y\rightarrow$$

which together with the carbon atom to which $R_{16}$ and $R_5$ are attached form a 5- to 7-membered spirocyclic ring, and in which
Y is oxygen or sulfur;
$R_{17}$ and $R_{18}$ are, independently from each other, hydrogen, $C_1$-$C_6$ alkyl, $C_1$-$C_6$ substituted alkyl, cycloalkyl, substituted cycloalkyl, aryl or substituted aryl;
n is zero, or an integer of 1 or 2; or
X is C—$R_{16}$ wherein $R_{16}$ and $R_5$ combined are a divalent radical of the formula which together with the carbon atom to which $R_{16}$ and $R_5$ are attached form a 5-membered spirocyclic ring, and in which
Y is oxygen or sulfur;
$R_{19}$ and $R_{20}$ are, independently from each other, hydrogen, halogen, cyano, trifluoromethyl, $C_1$-$C_6$ alkyl, $C_1$-$C_6$ substituted alkyl or $C_1$-$C_6$ alkoxy;

or a pharmaceutically acceptable salt thereof.

The compounds of the present invention provide pharmacological agents which are allosteric modulators of the $A_1$ adenosine receptor and, thus, may be employed for the treatment of conditions mediated by the $A_1$ adenosine receptor. Accordingly, the compounds of formula (I) may be employed for the treatment of pain, in particular, chronic pain such as neuropathic pain, cardiac disease or disorder such as cardiac disarrhythmias, e.g., peroxysmal supraventricular tachycardia, angina, myocardial infarction and stroke, neurological disease or injury, sleep disorders, epilepsy and depression.

Listed below are definitions of various terms used to describe the compounds of the present invention. These definitions apply to the terms as they are used throughout the specification unless they are otherwise limited in specific instances either individually or as part of a larger group, e.g., wherein an attachment point of a certain group is limited to a specific atom within that group, the point of attachment is defined by an arrow at the specific atom.

The term "alkyl" refers to a hydrocarbon chain having 1-20 carbon atoms, preferably 1-10 carbon atoms, and more preferably 1-7 carbon atoms. The hydrocarbon chain may be straight, as for a hexyl or n-butyl chain, or branched, as for example t-butyl, 2-methyl-pentyl, 3-propyl-heptyl. Exemplary alkyl groups include methyl, ethyl, propyl, isopropyl, n-butyl, t-butyl, isobutyl, pentyl, hexyl, isohexyl, heptyl, 4,4-dimethylpentyl, octyl, and the like.

The term "substituted alkyl" refers to those alkyl groups as described above substituted by one or more, preferably 1-3, of the following groups: halo, hydroxy, alkanoyl, alkoxy, cycloalkyl, cycloalkoxy, alkanoyloxy, thiol, alkylthio, alkylthiono, sulfonyl, sulfamoyl, carbamoyl, cyano, carboxy, acyl, aryl, aryloxy, alkenyl, alkynyl, aralkoxy, guanidino, optionally substituted amino, heterocyclyl including imidazolyl, furyl, thienyl, thiazolyl, pyrrolidyl, pyridyl, pyrimidyl and the like.

The term "lower alkyl" refers to those alkyl groups as described above having 1-6, preferably 1-4 carbon atoms.

The term "alkenyl" refers to any of the above alkyl groups having at least two carbon atoms and further containing a carbon-to-carbon double bond at the point of attachment. Groups having 2-6 carbon atoms are preferred.

The term "alkynyl" refers to any of the above alkyl groups having at least two carbon atoms and further containing a carbon-to-carbon triple bond at the point of attachment. Groups having 2-6 carbon atoms are preferred.

The term "alkylene" refers to a straight-chain bridge of 1-6 carbon atoms connected by single bonds, e.g., —(CH$_2$)$_x$—, wherein x is 1-6, in those cases where x is greater than 1, the chain may be interrupted with one or more groups selected from O, S, S(O), S(O)$_2$, CH=CH, C≡C or NR, wherein R may be hydrogen, alkyl, alkenyl, alkynyl, cycloalkyl, aryl, heterocyclyl, aralkyl, heteroaralkyl, acyl, carbamoyl, sulfonyl, alkoxycarbonyl, aryloxycarbonyl or aralkoxycarbonyl and the like; and the alkylene may further be substituted with one or more substituents selected from optionally substituted alkyl, cycloalkyl, aryl, heterocyclyl, oxo, halogen, hydroxy, carboxy, alkoxy, alkoxycarbonyl and the like.

The term "cycloalkyl" refers to monocyclic, bicyclic or tricyclic hydrocarbon groups of 3-12 carbon atoms, each of which may contain one or more carbon-to-carbon double bonds.

The term "substituted cycloalkyl" refers to those cycloalkyl groups as described above substituted by one or more substituents, preferably 1-3, such as alkyl, halo, oxo, hydroxy, alkoxy, alkanoyl, acylamino, carbamoyl, alkylamino, dialkylamino, thiol, alkylthio, cyano, carboxy, alkoxycarbonyl, sulfonyl, sulfonamido, sulfamoyl, heterocyclyl and the like.

Exemplary monocyclic hydrocarbon groups include, but are not limited to, cyclopropyl, cyclobutyl, cyclopentyl, cyclopentenyl, cyclohexyl, cyclohexenyl, 4,4-dimethylcyclohex-1-yl, cyclooctenyl and the like.

Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like.

Exemplary tricyclic hydrocarbon groups include adamantyl and the like.

In the definitions listed herein, when a reference to an alkyl, cycloalkyl, alkenyl or alkynyl group is made as part of the term, a substituted alkyl, cycloalkyl, alkenyl or alkynyl group is also intended.

The term "alkoxy" refers to alkyl-O—.
The term "cycloalkoxy" refers to cycloalkyl-O—.
The term "alkanoyl" refers to alkyl-C(O)—.
The term "cycloalkanoyl" refers to cycloalkyl-C(O)—.
The term "alkenoyl" refers to alkenyl-C(O)—.
The term "alkynoyl" refers to alkynyl-C(O)—.
The term "alkanoyloxy" refers to alkyl-C(O)—O—.
The terms "alkylamino" and "dialkylamino" refer to alkyl-NH— and (alkyl)$_2$N—, respectively.
The term "alkanoylamino" refers to alkyl-C(O)—NH—.
The term "alkylthio" refers to alkyl-S—.
The term "trialkylsilyl" refers to (alkyl)$_3$Si—.
The term "trialkylsilyloxy" refers to (alkyl)$_3$SiO—.
The term "alkylthiono" refers to alkyl-S(O)—.
The term "alkylsulfonyl" refers to alkyl-S(O)$_2$—.
The term "alkoxycarbonyl" refers to alkyl-O—C(O)—.
The term "alkoxycarbonyloxy" refers to alkyl-O—C(O)O—.
The term "carbamoyl" refers to H$_2$NC(O)—, alkyl-NHC(O)—, (alkyl)$_2$NC(O)—, aryl-NHC(O)—, alkyl(aryl)-NC(O)—, heteroaryl-NHC(O)—, alkyl(heteroaryl)-NC(O)—, aralkyl-NHC(O)—, alkyl(aralkyl)-NC(O)— and the like.
The term "sulfamoyl" refers to H$_2$NS(O)$_2$—, alkyl-NHS(O)$_2$—, (alkyl)$_2$NS(O)$_2$—, aryl-NHS(O)$_2$—, alkyl(aryl)-NS(O)$_2$—, (aryl)$_2$NS(O)$_2$—, heteroaryl-NHS(O)$_2$—, aralkyl-NHS(O)$_2$—, heteroaralkyl-NHS(O)$_2$— and the like.
The term "sulfonamido" refers to alkyl-S(O)$_2$—NH—, aryl-S(O)$_2$—NH—, aralkyl-S(O)$_2$—NH—, heteroaryl-S(O)$_2$—NH—, heteroaralkyl-S(O)$_2$—NH—, alkyl-S(O)$_2$—N(alkyl)-, aryl-S(O)$_2$—N(alkyl)-, aralkyl-S(O)$_2$—N(alkyl)-, heteroaryl-S(O)$_2$—N(alkyl)-, heteroaralkyl-S(O)$_2$—N(alkyl)- and the like.
The term "sulfonyl" refers to alkylsulfonyl, arylsulfonyl, heteroarylsulfonyl, aralkylsulfonyl, heteroaralkylsulfonyl and the like.
The term "optionally substituted amino" refers to a primary or secondary amino group which may optionally be substituted by a substituent such as acyl, sulfonyl, alkoxycarbonyl, cycloalkoxycarbonyl, aryloxycarbonyl, heteroaryloxycarbonyl, aralkoxycarbonyl, heteroaralkoxycarbonyl, carbamoyl and the like.
The term "aryl" refers to monocyclic or bicyclic aromatic hydrocarbon groups having 6-12 carbon atoms in the ring portion, such as phenyl, biphenyl, naphthyl, 2,3-dihydro-1H-indenyl and tetrahydronaphthyl.
The term "substituted aryl" refers to those aryl groups as described above substituted by 1-4 substituents in each ring portion, such as alkyl, trifluoromethyl, cycloalkyl, halo, hydroxy, alkoxy, methylenedioxy, acyl, alkanoyloxy, aryloxy, optionally substituted amino, thiol, alkylthio, arylthio, nitro, cyano, carboxy, alkoxycarbonyl, carbamoyl, alkylthiono, sulfonyl, sulfonamido, heterocyclyl and the like.
The term "monocyclic aryl" refers to optionally substituted phenyl as described above under aryl. Preferably, the monocyclic aryl is substituted by 1-3 substituents selected from the group consisting of halogen, cyano or trifluoromethyl.
In the definitions listed herein, when a reference to an aryl group is made as part of the term, a substituted aryl group is also intended.
The term "aralkyl" refers to an aryl group bonded directly through an alkyl group, such as benzyl.
The term "aralkanoyl" refers to aralkyl-C(O)—.
The term "aralkylthio" refers to aralkyl-S—.
The term "aralkoxy" refers to an aryl group bonded directly through an alkoxy group.
The term "arylsulfonyl" refers to aryl-S(O)$_2$—.
The term "arylthio" refers to aryl-S—.
The term "aroyl" refers to aryl-C(O)—.
The term "aroyloxy" refers to aryl-C(O)—O—.
The term "aroylamino" refers to aryl-C(O)—NH—.
The term "aryloxycarbonyl" refers to aryl-O—C(O)—.

The term "heterocyclyl" or "heterocyclo" refers to fully saturated or unsaturated, aromatic or nonaromatic cyclic group, e.g., which is a 4- to 7-membered monocyclic, 7- to 12-membered bicyclic or 10- to 15-membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized. The heterocyclic group may be attached at a heteroatom or a carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, triazolyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl (pyridyl), pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, 1,1,4-trioxo-1,2,5-thiadiazolidin-2-yl and the like.

Exemplary bicyclic heterocyclic groups include indolyl, dihydroidolyl, benzothiazolyl, benzoxazinyl, benzoxazolyl, benzothienyl, benzothiazinyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl or furo[2,3-b]pyridinyl), dihydroisoindolyl, 1,3-dioxo-1,3-dihydroisoindol-2-yl, dihydroquinazolinyl (such as 3,4-dihydro-4-oxo-quinazolinyl), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

The term "substituted heterocyclyl" refers to those heterocyclic groups described above substituted with 1, 2 or 3 substituents selected from the group consisting of the following:

(a) alkyl;
(b) hydroxyl (or protected hydroxyl);
(c) halo;
(d) oxo, i.e., =O;
(e) optionally substituted amino;
(f) alkoxy;
(g) cycloalkyl;
(h) carboxy;
(i) heterocyclooxy;
(j) alkoxycarbonyl, such as unsubstituted lower alkoxycarbonyl;
(k) thiol;
(l) nitro;
(m) cyano;
(n) sulfamoyl;
(o) alkanoyloxy;
(p) aroyloxy;
(q) arylthio;
(r) aryloxy;
(s) alkylthio;
(t) formyl;
(u) carbamoyl;
(v) aralkyl; and
(w) aryl optionally substituted with alkyl, cycloalkyl, alkoxy, hydroxyl, amino, acylamino, alkylamino, dialkylamino or halo.

The term "heterocyclooxy" denotes a heterocyclic group bonded through an oxygen bridge.

The term "heterocycloalkyl" refers to nonaromatic heterocyclic groups as described above.

The term "heteroaryl" refers to an aromatic heterocycle, e.g., monocyclic or bicyclic aryl, such as pyrrolyl, pyrazolyl, imidazolyl, triazolyl, oxazolyi, isoxazolyi, thiazolyl, isotniazolyi, furyl, thienyl, pyridyl, pyrazinyl, pyrimidinyl, pyridazinyl, indolyl, benzothiazolyl, benzoxazolyl, benzothienyl, quinolinyl, isoquinolinyl, benzimidazolyl, benzofuryl and the like, optionally substituted by, e.g., halogen, cyano, nitro, trifluoromethyl, lower alkyl or lower alkoxy.

The term "heterocycloalkanoyl" refers to heterocycloalkyl-C(O)—.

The term "heteroarylsulfonyl" refers to heteroaryl-$S(O)_2$—.

The term "heteroaroyl" refers to heteroaryl-C(O)—.

The term "heteroaroylamino" refers to heteroaryl-C(O)NH—.

The term "heteroaralkyl" refers to a heteroaryl group bonded through an alkyl group.

The term "heteroaralkanoyl" refers to heteroaralkyl-C(O)—.

The term "heteroaralkanoylamino" refers to heteroaralkyl-C(O)NH—.

The term "acyl" refers to alkanoyl, cycloalkanoyl, alkenoyl, alkynoyl, aroyl, heterocycloalkanoyl, heteroaroyl, aralkanoyl, heteroaralkanoyl and the like.

The term "substituted acyl" refers to those acyl groups described above wherein the alkyl, cycloalkyl, alkenyl, alkynyl, aryl, heterocycloalkyl, heteroaryl, aralkyl or heteroaralkyl group is substituted as described herein above respectively.

The term "acylamino" refers to alkanoylamino, aroylamino, heteroaroylamino, aralkanoylamino, heteroaralkanoylamino and the like.

The term "halogen" or "halo" refers to fluorine, chlorine, bromine and iodine.

Pharmaceutically acceptable salts of the compounds of the present invention refer to salts formed with acids, namely acid addition salts, such as of mineral acids, organic carboxylic acids and organic sulfonic acids, e.g., hydrochloric acid, maleic acid and methanesulfonic acid, respectively.

Similarly, pharmaceutically acceptable salts of the compounds of the invention refer to salts formed with bases, namely cationic salts, such as alkali and alkaline earth metal salts, e.g., sodium, lithium, potassium, calcium and magnesium, as well as ammonium salts, e.g., ammonium, trimethylammonium, diethylammonium and tris(hydroxymethyl)-methyl-ammonium salts and salts with amino acids provided an acidic group constitutes part of the structure.

As described herein above, the present invention provides 2-aminothiophene derivatives of formula (I), pharmaceutical compositions containing them, methods for preparing said compounds, and methods of treating conditions mediated by the $A_1$ adenosine receptor including, but not limited to, pain, in particular, chronic pain such as neuropathic pain; cardiac disease or disorder such as congestive heart failure, cardiac disarrhythmias, e.g., peroxysmal supraventricular, tachycardia, angina, myocardial infarction and stroke, neurological disease or injury, sleep disorders, epilepsy, depression, and various inflammatory conditions, by administration of a therapeutically effective amount of a compound of the present invention, or a pharmaceutical composition thereof.

In one aspect, the present invention provides compounds of formula (I), designated as the A group, wherein
X is N;

or a pharmaceutical composition thereof.
Preferred are the compounds in the A group, wherein
$R_1$ is hydrogen, alkyl, substituted alkyl, aryl or substituted aryl;

or a pharmaceutical composition thereof.
Further preferred are the compounds in the A group, designated as the B group, wherein Q is

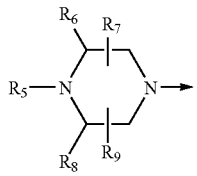

in which
$R_5$ is hydrogen, alkyl, substituted alkyl, aryl, substituted aryl, cycloalkyl, substituted cycloalkyl, heteroaryl, substituted heteroaryl, heteroaralkyl, substituted heteroaralkyl, acyl or substituted acyl;
$R_6$ and $R_7$ are, independently from each other, hydrogen, $C_1$-$C_3$ alkyl or $C_1$-$C_3$ substituted alkyl; or
$R_6$ and $R_7$, provided they are attached to the same carbon atom, combined are alkylene which together with the carbon atom to which they are attached form a 3- to 7-membered spirocyclic ring;
$R_8$ and $R_9$ are, independently from each other, hydrogen, $C_1$-$C_3$ alkyl or $C_1$-$C_3$ substituted alkyl;

or a pharmaceutically acceptable salt thereof.
Preferred are the compounds in the B group having formula (IA)

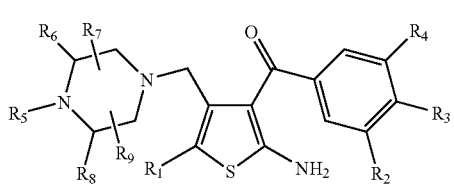

wherein
$R_1$ is hydrogen, alkyl, substituted alkyl, aryl or substituted aryl;
$R_2$, $R_3$, and $R_4$ are, independently from each other, hydrogen, alkyl, substituted alkyl, aryl, substituted aryl, cycloalkyl, substituted cycloalkyl, halogen, hydroxyl, nitro, cyano, alkoxy or substituted alkoxy;
$R_5$ is alkyl, substituted alkyl, aryl, substituted aryl, cycloalkyl, substituted cycloalkyl, heteroaryl, substituted heteroaryl, heteroaralkyl, substituted heteroaralkyl, acyl or substituted acyl;
$R_6$, $R_7$, $R_8$ and $R_9$ are, independently from each other, hydrogen, $C_1$-$C_3$ alkyl or $C_1$-$C_3$ substituted alkyl;

or a pharmaceutically acceptable salt thereof.
Preferred are the compounds of formula (IA), wherein
$R_1$ is hydrogen or $C_1$-$C_3$ alkyl;

or a pharmaceutically acceptable salt thereof.

Preferred are also the compounds of formula (IA), wherein
$R_5$ is monocyclic aryl optionally substituted by one to three substituents selected from the group consisting of halogen, cyano or trifluoromethyl;

or a pharmaceutically acceptable salt thereof.
Preferred are also the compounds of formula (IA), designated as the C group, wherein
$R_2$ and $R_4$ are hydrogen;

or a pharmaceutically acceptable salt thereof.
Preferred are the compounds in the C group, wherein
$R_3$ is halogen, cyano or trifluoromethyl;

or a pharmaceutically acceptable salt thereof.
Preferred are also the compounds of formula (IA), designated as the D group, wherein
$R_2$ and $R_3$ are hydrogen;

or a pharmaceutically acceptable salt thereof.
Preferred are the compounds in the D group, wherein
$R_4$ is halogen, cyano or trifluoromethyl;

or a pharmaceutically acceptable salt thereof.
Preferred are also the compounds of formula (IA), designated as the E group, wherein
$R_6$, $R_7$, $R_8$ and $R_9$ are, independently from each other, hydrogen or $C_1$-$C_3$ alkyl;

or a pharmaceutically acceptable salt thereof.
Preferred are the compounds in the E group, designated as the F group, wherein
$R_5$ is monocyclic aryl optionally substituted by one to three substituents selected from the group consisting of halogen, cyano or trifluoromethyl;

or a pharmaceutically acceptable salt thereof.
Preferred are the compounds in the F group, designated as the G group, wherein
$R_2$ and $R_4$ are hydrogen;

or a pharmaceutically acceptable salt thereof.
Preferred are the compounds in the G group, wherein
$R_3$ is halogen, cyano or trifluoromethyl;

or a pharmaceutically acceptable salt thereof.
Further preferred are the compounds in the G group, wherein
$R_1$ is hydrogen or $C_1$-$C_3$ alkyl;

or a pharmaceutically acceptable salt thereof.
Preferred are also the compounds in the F group, designated as the H group, wherein
$R_2$ and $R_3$ are hydrogen;

or a pharmaceutically acceptable salt thereof.
Preferred are the compounds in the H group, wherein
$R_4$ is halogen, cyano or trifluoromethyl;

or a pharmaceutically acceptable salt thereof.
Further preferred are the compounds in the H group, wherein
$R_1$ is hydrogen or $C_1$-$C_3$ alkyl;

or a pharmaceutically acceptable salt thereof.
In another aspect, the present invention provides compounds of formula (I), designated as the I group, wherein
X is C—H; or
X is C—$NR_{14}R_{15}$ wherein $R_{14}$ and $R_{15}$ are, independently from each other, hydrogen, $C_1$-$C_3$ alkyl, $C_1$-$C_3$ substituted alkyl, aryl or substituted aryl; or
X is C—$R_{16}$ wherein $R_{16}$ and $R_5$ combined are a carbonyl oxygen; or X is C—$R_{16}$ wherein $R_{16}$ and $R_5$ combined are a divalent radical of the formula

which together with the carbon atom to which $R_{16}$ and $R_5$ are attached form a 5- to 7-membered spirocyclic ring, and in which Y is oxygen or sulfur;

$R_{17}$ and $R_{18}$ are, independently from each other, hydrogen, $C_1$-$C_6$ alkyl, $C_1$-$C_6$ substituted alkyl, cycloalkyl, substituted cycloalkyl, aryl or substituted aryl;

n is zero, or an integer of 1 or 2; or

X is C—$R_{16}$ wherein $R_{16}$ and $R_5$ combined are a divalent radical of the formula

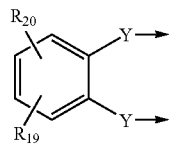

which together with the carbon atom to which $R_{16}$ and $R_5$ are attached form a 5-membered spirocyclic ring, and in which Y is oxygen or sulfur;

$R_{19}$ and $R_{20}$ are, independently from each other, hydrogen, halogen, cyano, trifluoromethyl, $C_1$-$C_6$ alkyl, $C_1$-$C_6$ substituted alkyl or $C_1$-$C_6$ alkoxy;

or a pharmaceutically acceptable salt thereof.

Preferred are the compounds in the I group, wherein $R_1$ is hydrogen, alkyl, substituted alkyl, aryl or substituted aryl;

or a pharmaceutical composition thereof.

Further preferred are the compounds in the I group, designated as the J group, wherein Q is

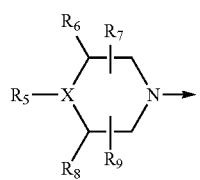

in which $R_5$ is hydrogen, alkyl, substituted alkyl, aryl, substituted aryl, cycloalkyl, substituted cycloalkyl, heteroaryl, substituted heteroaryl, heteroaralkyl, substituted heteroaralkyl, acyl or substituted acyl;

$R_6$ and $R_7$ are, independently from each other, hydrogen, $C_1$-$C_3$ alkyl or $C_1$-$C_3$ substituted alkyl; or $R_6$ and $R_7$, provided they are attached to the same carbon atom, combined are alkylene which together with the carbon atom to which they are attached form a 3- to 7-membered spirocyclic ring;

X is C—H; or

X is C—$NR_{14}R_{15}$ wherein $R_{14}$ and $R_{15}$ are, independently from each other, hydrogen, $C_1$-$C_3$ alkyl, $C_1$-$C_3$ substituted alkyl, aryl or substituted aryl; or X is C—$R_{16}$ wherein $R_{16}$ and $R_5$ combined are a divalent radical of the formula

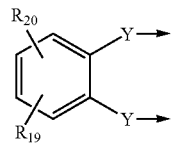

which together with the carbon atom to which $R_{16}$ and $R_5$ are attached form a 5-membered spirocyclic ring, and in which Y is oxygen or sulfur;

$R_{19}$ and $R_{20}$ are, independently from each other, hydrogen, halogen, cyano, trifluoromethyl, $C_1$-$C_6$ alkyl, $C_1$-$C_6$ substituted alkyl or $C_1$-$C_6$ alkoxy;

or a pharmaceutically acceptable salt thereof.

Preferred are the compounds in the J group wherein

X is C—$R_{16}$ wherein $R_{16}$ and $R_5$ combined are a divalent radical of the formula

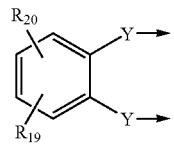

which together with the carbon atom to which $R_{16}$ and $R_5$ are attached form a 5-membered spirocyclic ring, and in which Y is oxygen;

$R_{19}$ and $R_{20}$ are, independently from each other, hydrogen, halogen, cyano, trifluoromethyl, $C_1$-$C_6$ alkyl, $C_1$-$C_6$ substituted alkyl or $C_1$-$C_6$ alkoxy;

or a pharmaceutically acceptable salt thereof.

Further preferred are the compounds in the J group having formula (IB)

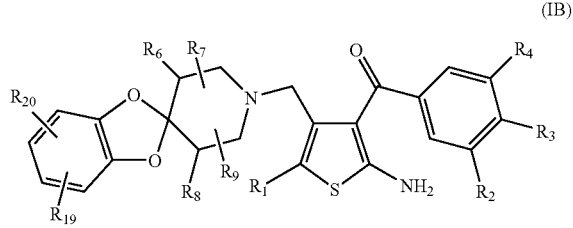

(IB)

wherein $R_1$ is hydrogen, alkyl, substituted alkyl, aryl or substituted aryl;

$R_2$, $R_3$, and $R_4$ are, independently from each other, hydrogen, alkyl, substituted alkyl, aryl, substituted aryl, cycloalkyl, substituted cycloalkyl, halogen, hydroxyl, nitro, cyano, alkoxy or substituted alkoxy;

$R_6$, $R_7$, $R_8$ and $R_9$ are, independently from each other, hydrogen, $C_1$-$C_3$ alkyl or $C_1$-$C_3$ substituted alkyl; or $R_{19}$ and $R_{20}$ are, independently from each other, hydrogen, halogen, cyano, trifluoromethyl $C_1$-$C_6$ alkyl, $C_1$-$C_6$ substituted alkyl or $C_1$-$C_6$ alkoxy;

or a pharmaceutically acceptable salt thereof.

Preferred are the compounds of formula (IB), wherein
$R_1$ is hydrogen or $C_1$-$C_3$ alkyl;

or a pharmaceutically acceptable salt thereof.

Preferred are also the compounds of formula (IB), wherein
$R_{19}$ and $R_{20}$ are, independently from each other, hydrogen, halogen, cyano, trifluoromethyl or $C_1$-$C_4$ alkyl;

or a pharmaceutically acceptable salt thereof.

Preferred are also the compounds of formula (IB), designated as the K group, wherein
$R_2$ and $R_4$ are hydrogen;

or a pharmaceutically acceptable salt thereof.

Preferred are the compounds in the K group, wherein
$R_3$ is halogen, cyano or trifluoromethyl;

or a pharmaceutically acceptable salt thereof.

Preferred are also the compounds of formula (IB), designated as the L group, wherein
$R_2$ and $R_3$ are hydrogen;

or a pharmaceutically acceptable salt thereof.

Preferred are the compounds in the L group, wherein
$R_4$ is halogen, cyano or trifluoromethyl;

or a pharmaceutically acceptable salt thereof.

Preferred are also the compounds of formula (IB), designated as the M group, wherein
$R_6$, $R_7$, $R_8$ and $R_9$ are hydrogen;

or a pharmaceutically acceptable salt thereof.

Preferred are the compounds in the M group, designated as the N group, wherein
$R_{19}$ and $R_{20}$ are, independently from each other, hydrogen, halogen, cyano, trifluoromethyl or $C_1$-$C_4$ alkyl;

or a pharmaceutically acceptable salt thereof.

Preferred are the compounds in the N group, designated as the O group, wherein
$R_2$ and $R_4$ are hydrogen;

or a pharmaceutically acceptable salt thereof.

Preferred are the compounds in the 0 group, wherein
$R_3$ is halogen, cyano or trifluoromethyl;

or a pharmaceutically acceptable salt thereof.

Further preferred are the compounds in the O group, wherein
$R_1$ is hydrogen or $C_1$-$C_3$ alkyl;

or a pharmaceutically acceptable salt thereof.

Preferred are also the compounds in the N group, designated as the P group, wherein
$R_2$ and $R_3$ are hydrogen;

or a pharmaceutically acceptable salt thereof.

Preferred are the compounds in the P group, wherein
$R_4$ is halogen, cyano or trifluoromethyl;

or a pharmaceutically acceptable salt thereof.

Further preferred are the compounds in the P group, wherein
$R_1$ is hydrogen or $C_1$-$C_3$ alkyl;

or a pharmaceutically acceptable salt thereof.

The compounds of the invention depending on the nature of the substituents may possess one or more asymmetric centers. The resulting diastereoisomers, optical isomers, i.e., enantiomers, and geometric isomers, and mixtures thereof, are encompassed by the instant invention.

Particular embodiments of the invention are:
{2-Amino-4-[(4-phenylpiperazin-1-yl)methyl]thiophen-3-yl}(4-chlorophenyl)methanone;
{2-Amino-4-[(4-methylpiperazin-1-yl)methyl]thiophen-3-yl}(4-chlorophenyl)methanone;
{2-Amino-4-[4-((4-fluorophenyl)piperazin-1-yl)methyl]thiophen-3-yl}(4-chlorophenyl)methanone;
{2-Amino-4-[4-((4-chlorophenyl)piperazin-1-yl)methyl]thiophen-3-yl}(4-chlorophenyl)methanone;
{2-Amino-4-[4-((4-methoxyphenyl)piperazin-1-yl)methyl]thiophen-3-yl}(4-chlorophenyl)methanone;
{2-Amino-4-[(4-p-tolylpiperazin-1-yl)methyl]thiophen-3-yl}(4-chlorophenyl)methanone;
{2-Amino-4-[(4-(pyridin-2-yl)piperazin-1-yl)methyl]thiophen-3-yl}(4-chlorophenyl)methanone;
{2-Amino-4-[(4-(pyrimidin-2-yl)piperazin-1-yl)methyl]thiophen-3-yl}(4-chlorophenyl)methanone;
{2-Amino-4-[(4-(3,4-dichlorophenyl)-piperazin-1-yl)methyl]thiophen-3-yl}(4-chlorophenyl)methanone;
4-{4-[(5-Amino-4-(4-chlorobenzoyl)thiophen-3-yl)methyl]piperazin-1-yl}benzonitrile;
{2-Amino-4-[(4-(3-chlorophenyl)-piperazin-1-yl)methyl]thiophen-3-yl}(4-chlorophenyl)methanone;
{2-Amino-4-[(4-(2-chlorophenyl)piperazin-1-yl)methyl]thiophen-3-yl}(4-chlorophenyl)methanone;
{2-Amino-4-[(4-(2-fluorophenyl)-piperazin-1-yl)methyl]thiophen-3-yl}(4-chlorophenyl)methanone;
{2-Amino-4-[(4-(3-(trifluoromethyl)phenyl)piperazin-1-yl)methyl]thiophen-3-yl}(4-chlorophenyl)methanone;
1-{4-[(5-Amino-4-(4-chlorobenzoyl)thiophen-3-yl)methyl]piperazin-1-yl}-2-(4-chlorophenyl)ethanone;
{2-Amino-4-[(4-(4-chlorobenzoyl)piperazin-1-yl)methyl]thiophen-3-yl}(4-chlorophenyl)methanone;
{2-Amino-4-[(4-(pyridin-4-yl)piperazin-1-yl)methyl]thiophen-3-yl}(4-chlorophenyl)methanone;
{2-Amino-4-[(4-(benzo[d][1,3]dioxol-5-yl)piperazin-1-yl)methyl]thiophen-3-yl}(4-chlorophenyl)methanone;
{2-Amino-4-[(4-(2,3-dichlorophenyl)piperazin-1-yl)methyl]thiophen-3-yl}(4-chlorophenyl)methanone;
{2-Amino-4-[(4-(3-fluorophenyl)piperazin-1-yl)methyl]thiophen-3-yl}(4-chlorophenyl)methanone;
{2-Amino-4-[(4-(3,5-dichlorophenyl)piperazin-1-yl)methyl]thiophen-3-yl}(4-chlorophenyl)methanone;
{2-Amino-4-[(4-(4-(trifluoromethyl)phenyl)piperazin-1-yl)methyl]thiophen-3-yl}(4-chlorophenyl)methanone;
2-{4-[(5-Amino-4-(4-chlorobenzoyl)thiophen-3-yl)methyl]piperazin-1-yl}-1-(4-chlorophenyl)ethanone;
{2-Amino-4-[(4-(2,4-difluorophenyl)piperazin-1-yl)methyl]thiophen-3-yl}(4-chlorophenyl)methanone;
{2-Amino-4-[(4-(2,6-difluorophenyl)piperazin-1-yl)methyl]thiophen-3-yl}(4-chlorophenyl)methanone;
{2-Amino-4-[(4-(3-chloro-4-fluorophenyl)piperazin-1-yl)methyl]thiophen-3-yl}(4-chlorophenyl)methanone;
{2-Amino-4-[(4-cyclohexylpiperazin-1-yl)methyl]thiophen-3-yl}(4-chlorophenyl)methanone;
{2-Amino-4-[(4-(4-chlorophenyl)piperidin-1-yl)methyl]thiophen-3-yl}(4-chlorophenyl)methanone;
{2-Amino-4-[(4-(4-nitrophenyl)piperazin-1-yl)methyl]thiophen-3-yl}(4-chlorophenyl)methanone;
{2-Amino-4-[(4-isopropyl)piperazin-1-yl)methyl]thiophen-3-yl}(4-chlorophenyl)methanone;
{2-Amino-4-[(4-naphthalen-1-yl)piperazin-1-yl)methyl]thiophen-3-yl}(4-chlorophenyl)methanone;
{2-Amino-4-[(4-(3,4-difluorophenyl)piperazin-1-yl)methyl]thiophen-3-yl}(4-chlorophenyl)methanone;

{2-Amino-4-[(4-cyclopentylpiperazin-1-yl)methyl]
thiophen-3-yl}(4-chlorophenyl)methanone;
{2-Amino-4-[(4-cycloheptylpiperazin-1-yl)methyl]
thiophen-3-yl}(4-chlorophenyl)methanone;
{2-Amino-4-[(4-(4-chlorobenzyl)piperazin-1-yl)methyl]
thiophen-3-yl}(4-chlorophenyl)methanone;
{2-Amino-4-[(4-benzylpiperazin-1-yl)methyl]thiophen-3-
yl}(4-chlorophenyl)methanone;
(2-Amino-4-{[4-(2-(4-chlorophenyl)ethyl)piperazin-1-yl]
methyl}thiophen-3-yl)(4-chlorophenyl)methanone;
{2-Amino-4-[(4-(4-fluorobenzyl)piperazin-1-yl)methyl]
thiophen-3-yl}(4-chlorophenyl)methanone;
{2-Amino-4-[(4-cyclooctylpiperazin-1-yl)methyl]thiophen-
3-yl}(4-chlorophenyl)methanone;
(2-Amino-4-{[4-[3-(4-chlorophenyl)propyl]piperazin-1-yl]
methyl}thiophen-3-yl)(4-chlorophenyl)methanone;
{2-Amino-4-[(4-(2,4-dichlorophenyl)piperazin-1-yl)me-
thyl]thiophen-3-yl}(4-chlorophenyl)methanone;
{2-Amino-4-[(4-(2,5-difluorophenyl)piperazin-1-yl)me-
thyl]thiophen-3-yl}(4-chlorophenyl)methanone;
{2-Amino-4-[(4-(2-(trifluoromethyl)phenyl)piperazin-1-yl)
methyl]thiophen-3-yl}(4-chlorophenyl)methanone;
{2-Amino-4-[(4-(4-chloro-3-(trifluoromethyl)phenyl)piper-
azin-1-yl)methyl]thiophen-3-yl}(4-chlorophenyl)metha-
none;
{2-Amino-4-[(4-(2,4,6-trifluorophenyl)piperazin-1-yl)me-
thyl]thiophen-3-yl}(4-chlorophenyl)methanone;
{2-Amino-4-[(4-(2-chloro-4-fluorophenyl)piperazin-1-yl)
methyl]thiophen-3-yl}(4-chlorophenyl)methanone;
{2-Amino-4-[(4-(2-fluoro-4-chlorophenyl)piperazin-1-yl)
methyl]thiophen-3-yl}(4-chlorophenyl)methanone;
{2-Amino-4-[(4-(3,5-difluorophenyl)piperazin-1-yl)me-
thyl]thiophen-3-yl}(4-chlorophenyl)methanone;
{2-Amino-4-[(4-(2,6-dichlorophenyl)piperazin-1-yl)me-
thyl]thiophen-3-yl}(4-chlorophenyl)methanone;
{2-Amino-4-[(4-(4-(trifluoromethoxy)phenyl)piperazin-1-
yl)methyl]thiophen-3-yl}(4-chlorophenyl)methanone;
{2-Amino-4-[(4-(pyridin-3-yl)piperazin-1-yl)methyl]
thiophen-3-yl}(4-chlorophenyl)methanone;
{2-Amino-4-[(4-(2,5-dichlorophenyl)piperazin-1-yl)me-
thyl]thiophen-3-yl}(4-chlorophenyl)methanone;
{2-Amino-4-[((4-(2,3-difluorophenyl)piperazin-1-yl)me-
thyl]thiophen-3-yl}(4-chlorophenyl)methanone;
{2-Amino-4-[(4-(4-chlorophenyl)-3-methylpiperazin-1-yl)
methyl]thiophen-3-yl}(4-chlorophenyl)methanone;
{2-Amino-4-[(4-(4-(trifluoromethyl)phenyl)piperazin-1-yl)
methyl]thiophen-3-yl}[3-(trifluoromethyl)phenyl]metha-
none;
{2-Amino-4-[(4-(3-fluorophenyl)piperazin-1-yl)methyl]
thiophen-3-yl}[3-(trifluoromethyl)phenyl]methanone;
{2-Amino-4-[(4-(2,6-difluorophenyl)piperazin-1-yl)me-
thyl]thiophen-3-yl}[3-(trifluoromethyl)phenyl]metha-
none;
{2-Amino-4-(spiro[benzo[d][1,3]-dioxole-2,4'-piperidine]-
1'-ylmethyl)thiophen-3-yl}(4-chlorophenyl)methanone;
{2-Amino-4-(5-tert-butylspiro[benzo[d][1,3]-dioxole-2,4'-
piperidine]-1'-ylmethyl)thiophen-3-yl}(4-chlorophenyl)
methanone;
{2-Amino-4-(4-fluorospiro[benzo[d][1,3]-dioxole-2,4'-pip-
eridine]-1'-ylmethyl)thiophen-3-yl}(4-chlorophenyl)
methanone;
{2-Amino-4-(4-methylspiro[benzo[d][1,3]-dioxole-2,4'-pi-
peridine]-1'-ylmethyl)thiophen-3-yl}(4-chlorophenyl)
methanone;
{2-Amino-4-(5-methylspiro[benzo[d][1,3]-dioxole-2,4'-pi-
peridine]-1'-ylmethyl)thiophen-3-yl}(4-chlorophenyl)
methanone;
{2-Amino-4-[4-((4-chlorophenylamino)piperidin-1-yl)me-
thyl]thiophen-3-yl}(4-chlorophenyl)methanone;
{2-Amino-4-[(4-(4-chlorophenyl)methylamino]piperidin-1-
yl)methyl]thiophen-3-yl}(4-chlorophenyl)methanone;
{2-Amino-4-[(4-(4-chlorophenyl)-[1,4]diazepan-1-yl)me-
thyl]thiophen-3-yl}(4-chlorophenyl)methanone;
{2-Amino-4-[(7-(4-chlorophenyl)-2,7-diaza-spiro[4.4]non-
2-yl)methyl]thiophen-3-yl}(4-chlorophenyl)methanone;
{2-Amino-4-[(5-(4-chlorophenyl)hexahydropyrrolo[3,4-c]
pyrrol-2-yl)methyl]thiophen-3-yl}(4-chlorophenyl)
methanone;
{2-Amino-4-[(5-(4-chlorophenyl)-2,5-diazabicyclo[2.2.1]
hept-2-yl)methyl]thiophen-3-yl}(4-chlorophenyl)metha-
none;
{2-Amino-4-[(4-(4-fluorophenyl)piperazin-1-yl)methyl]-5-
methylthiophen-3-yl}(4-chlorophenyl)methanone;
{2-Amino-5-methyl-4-[(4-phenylpiperazin-1-yl)methyl]
thiophen-3-yl}(4-chlorophenyl)methanone;
{2-Amino-5-methyl-4-[(4-(4-(trifluoromethyl)phenyl)pip-
erazin-1-yl)methyl]thiophen-3-yl}(4-chlorophenyl)
methanone;
{2-Amino-4-[(4-(4-chlorophenyl)piperazin-1-yl)methyl]-5-
methylthiophen-3-yl}(4-chlorophenyl)methanone;
{2-Amino-4-[(4-(4-bromophenyl)piperazin-1-yl)methyl]-5-
methylthiophen-3-yl}(4-chlorophenyl)methanone;
{2-Amino-4-[(4-(4-iodophenyl)piperazin-1-yl)methyl]-5-
methylthiophen-3-yl}(4-chlorophenyl)methanone;
{2-Amino-5-methyl-4-[(4-(4-nitrophenyl)piperazin-1-yl)
methyl]thiophen-3-yl}(4-chlorophenyl)methanone;
4-{4-[(5-Amino-4-(4-chlorobenzoyl)-2-methylthiophen-3-
yl)methyl]piperazin-1-yl}benzonitrile
{2-Amino-4-[(4-benzylpiperazin-1-yl)methyl)-5-methylth-
iophen-3-yl](4-chlorophenyl)methanone;
{2-Amino-4-[(4-(4-methoxyphenyl)piperazin-1-yl)methyl]-
5-methylthiophen-3-yl}(4-chlorophenyl)methanone;
{2-Amino-5-methyl-4-[(4-p-tolylpiperazin-1-yl)methyl]
thiophen-3-yl}(4-chlorophenyl)methanone;
{2-Amino-4-[(4-(3,4-dichlorophenyl)piperazin-1-yl)me-
thyl]-5-methylthiophen-3-yl}(4-chlorophenyl)metha-
none;
{2-Amino-5-methyl-4-[(4-(3-(trifluoromethyl)phenyl)pip-
erazin-1-yl)methyl]thiophen-3-yl}(4-chlorophenyl)
methanone;
{2-Amino-4-[(4-(3-chlorophenyl)piperazin-1-yl)methyl]-5-
methylthiophen-3-yl}(4-chlorophenyl)methanone;
{2-Amino-4-[(4-(4-chloro-3-(trifluoromethyl)phenyl)piper-
azin-1-yl)methyl]-5-methylthiophen-3-yl}(4-chlorophe-
nyl)methanone;
{2-Amino-5-phenyl-4-[(piperidin-1-yl)methyl]thiophen-3-
yl}(4-chlorophenyl)methanone;
{2-Amino-4-[4-(4-fluorophenyl)piperazin-1-yl)methyl]-5-
ethylthiophen-3-yl}(4-chlorophenyl)methanone;
{2-Amino-5-ethyl-4-[(4-phenylpiperazin-1-yl)methyl]
thiophen-3-yl}(4-chlorophenyl)methanone;
{2-Amino-4-[(4-(4-chlorophenyl)piperazin-1-yl)methyl]-5-
ethylthiophen-3-yl}(4-chlorophenyl)methanone; and
{2-Amino-4-[(4-(3-fluorophenyl)piperazin-1-yl)methyl]-5-
methylthiophen-3-yl}(4-chlorophenyl)methanone;

or a pharmaceutically acceptable salt thereof.

Preferred embodiments of the present invention include,
but are not limited to:
{2-Amino-4-[(4-phenylpiperazin-1-yl)methyl]thiophen-3-
yl}(4-chlorophenyl)methanone;
{2-Amino-4-[4-((4-chlorophenyl)piperazin-1-yl)methyl]
thiophen-3-yl}(4-chlorophenyl)methanone; and {2-Amino-4-[4-((4-trifluoromethylphenyl)piperazin-1-yl)methyl]thiophen-3-yl}(4-chlorophenyl)methanone;

or a pharmaceutically acceptable salt thereof.

Compounds of formula (I) may be prepared using methods well known in the art, or using modifications thereof, e.g., as outlined below in Scheme 1 for compounds of formula (I), wherein $R_1$ is hydrogen.

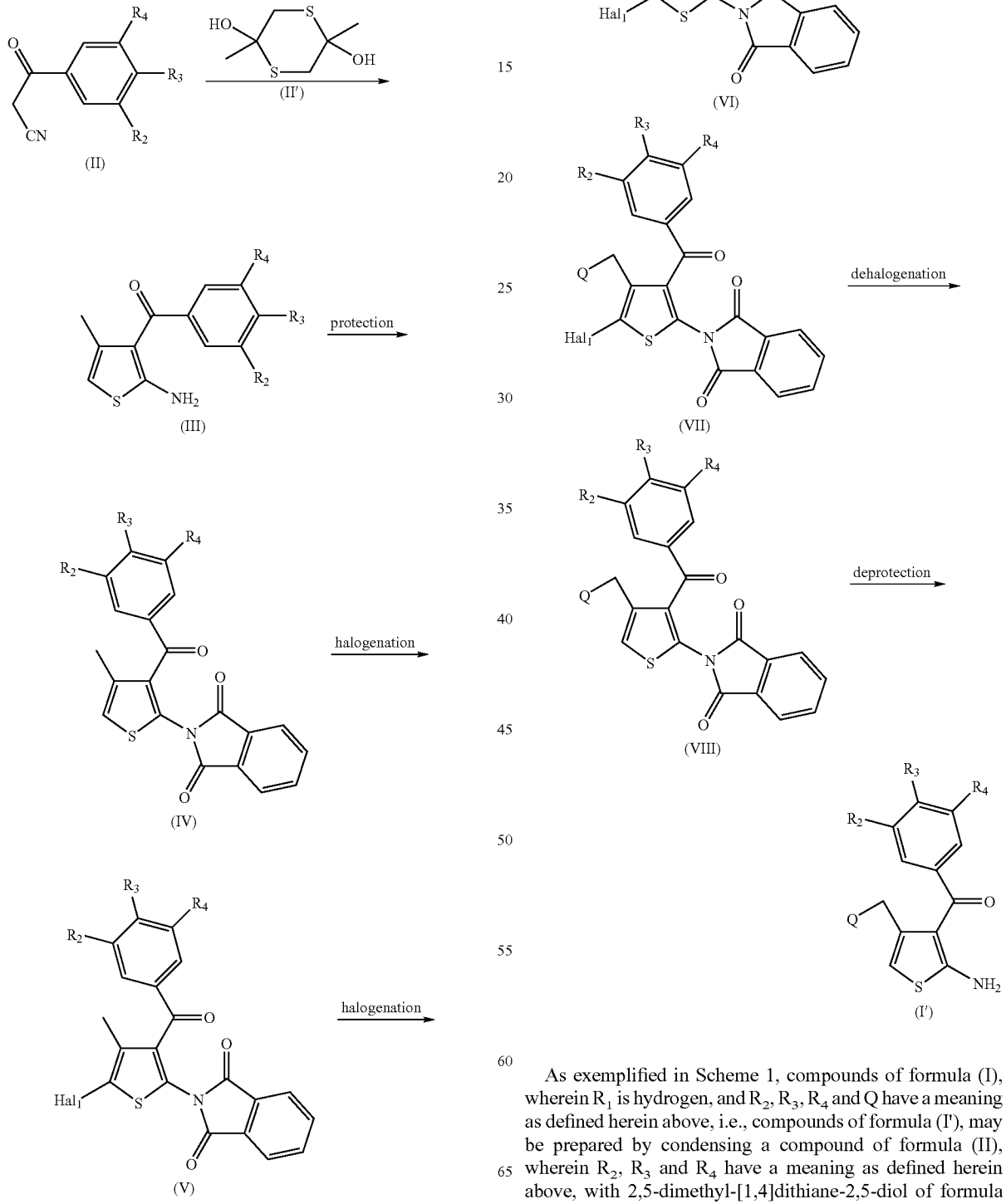

As exemplified in Scheme 1, compounds of formula (I), wherein $R_1$ is hydrogen, and $R_2$, $R_3$, $R_4$ and Q have a meaning as defined herein above, i.e., compounds of formula (I'), may be prepared by condensing a compound of formula (II), wherein $R_2$, $R_3$ and $R_4$ have a meaning as defined herein above, with 2,5-dimethyl-[1,4]dithiane-2,5-diol of formula (II') in the presence of a base such as triethylamine (TEA), diisopropylethylamine (DIEA), morpholine or N-methylmorpholine (NMM) in an organic solvent such as a lower alcohol, preferably, ethanol (EtOH), to afford a compound of formula (III), wherein $R_2$, $R_3$ and $R_4$ have a meaning as defined herein above.

Compounds of formula (II) are known, or if they are novel they may be prepared using methods well known in the art, or modifications thereof, e.g., as described in U.S. Pat. No. 6,323,214.

A resulting compound of formula (III) may then be converted to a compound (IV), wherein $R_2$, $R_3$ and $R_4$ have a meaning as defined herein above, and the amino group has been protected as a phthalimido group, under reaction conditions well known in the art, e.g., by treating a compound of formula (III) with phthalic anhydride in the presence of an acid, such as acetic acid, at an elevated temperature.

A resulting compound of formula (IV) may then be halogenated at the 5-position of the thiophene ring to afford a compound of formula (V), wherein $R_2$, $R_3$ and $R_4$ have a meaning as defined herein above, and $Hal_1$ represents chloride, bromide or iodide, using methods well known in the art, e.g., a compound of formula of formula (IV) may be treated with a halogenating agent such as N-halosuccinimide, e.g., N-bromosuccinimide, in the presence of a catalyst such as benzoyl peroxide, and an inert organic solvent, such as an aromatic hydrocarbon, e.g., benzene, to afford a compound of formula (V), wherein $Hal_1$ is, e.g., bromide.

Subsequent reaction of a resulting compound of formula (V) with a halogenating agent such as N-halosuccinimide, e.g., N-bromosuccinimide, in the presence of a catalyst such as benzoyl peroxide and an organic solvent such as a halogenated hydrocarbon, e.g., carbontetrachloride or dichloroethane, affords a compound of formula (VI), wherein $R_2$, $R_3$ and $R_4$ have a meaning as defined herein above, and $Hal_1$ and $Hal_2$ represent, independently from each other, chloride, bromide or iodide.

A resulting compound of formula (VI) may then be coupled with an amine of formula (VI'), wherein Q has a meaning as defined herein above, in the presence of a base such as TEA, DIEA, NMM, or potassium or cesium carbonate, and an appropriate organic solvent, such as dichloromethane (DCM), chloroform ($CHCl_3$) and N,N-dimethylformamide (DMF), to afford a compound of formula (VII), wherein $R_2$, $R_3$, $R_4$, Q and $Hal_1$ have a meaning as defined herein above.

Amines of formula (VI') are known, or if they are novel they may be prepared using methods well known in the art, or modifications thereof.

A resulting compound of formula (VII) may then be dehalogenated in the presence of a reducing agent, e.g., molecular hydrogen in the presence of a catalyst such as palladium on carbon, and an organic solvent, such as ethyl acetate (EtOAc), a lower alcohol, e.g., EtOH and methanol (MeOH), tetrahydrofuran (THF) or DMF, to afford a compound of formula (VIII), wherein $R_2$, $R_3$, $R_4$ and Q have a meaning as defined herein above. Preferably, the dehalogenation is conducted in the presence of an extrinsic base, e.g., TEA.

Finally, a compound of formula (VIII) may be converted to a compound of formula (I'), wherein $R_2$, $R_3$, $R_4$ and Q have a meaning as defined herein above, by removal of the phthalimido protecting group, e.g., by treatment with hydrazine in an organic solvent such as lower alcohol, e.g., EtOH.

As exemplified in Scheme 2, compounds of formula (I), wherein $R_1$ is alkyl, substituted alkyl, cycloalkyl, substituted cycloalkyl, aryl or substituted aryl, and $R_2$, $R_3$, $R_4$, and Q have a meaning as defined herein above may be prepared by the reaction of a compound of formula (II), wherein $R_2$, $R_3$, and $R_4$ have a meaning as defined herein above, with a ketone of formula (IX), wherein $R_1$ is alkyl, substituted alkyl, cycloalkyl, substituted cycloalkyl, aryl or substituted aryl, in the presence of elemental sulfur and an appropriate base, such as TEA, DIEA, morpholine or NMM, preferably morpholine, in an organic solvent such as a lower alcohol, preferably EtOH, to afford a compound of formula (III'), wherein $R_1$ is alkyl, substituted alkyl, cycloalkyl, substituted cycloalkyl, aryl or substituted aryl, and $R_2$, $R_3$, and $R_4$ have a meaning as defined herein above.

Scheme 2:

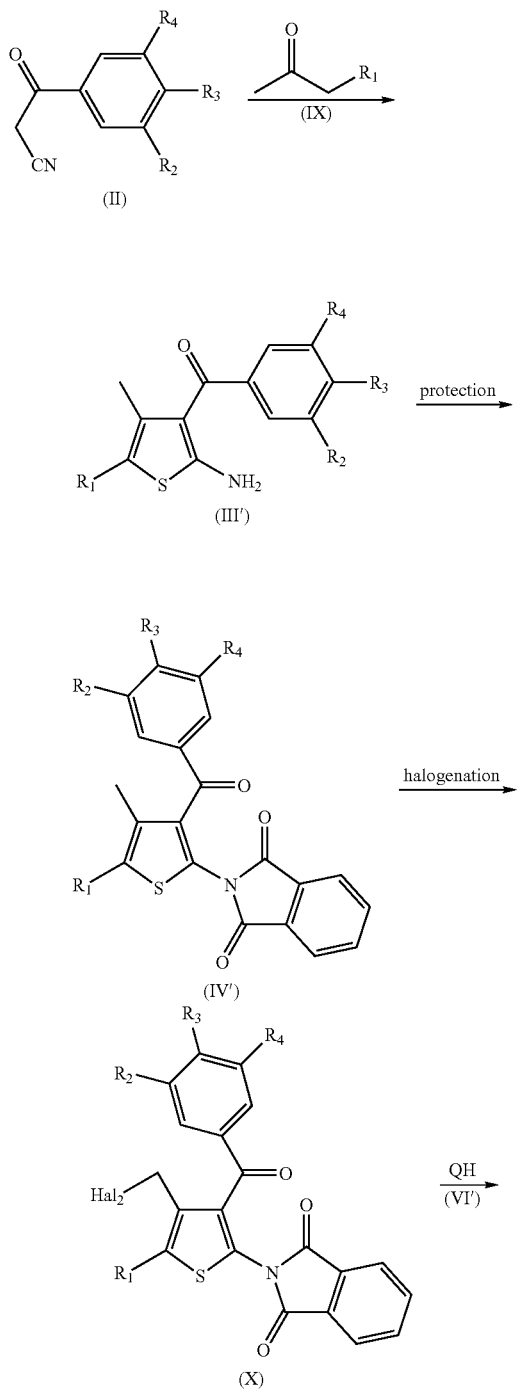

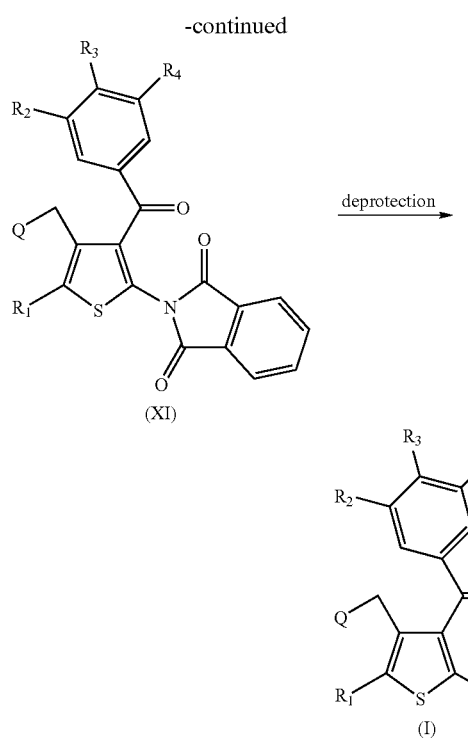

(XI)

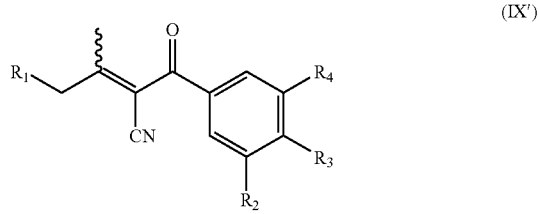

(I)

Alternatively, compounds of formula (II), wherein $R_2$, $R_3$, and $R_4$ have a meaning as defined herein above, may be first condensed (Knoevenagel condensation) with a ketone of formula (IX), wherein $R_1$ is alkyl, substituted alkyl, cycloalkyl, substituted cycloalkyl, aryl or substituted aryl, in the presence of a weak base, such as piperidine, pyrrolidine, morpholine or β-alanine, and an organic solvent, such as benzene or toluene, to afford a compound of the formula

(IX')

wherein $R_1$, $R_2$, $R_3$, and $R_4$ have a meaning as defined herein above, as a mixture of the E and Z isomers. Preferably, the condensation is conducted in the presence of an organic acid, such as acetic acid, at a temperature near the boiling point of the solvent. A subsequent treatment of a compound of formula (IX') with an elemental sulfur and an appropriate base, such as TEA, DIEA, morpholine or NMM, preferably TEA, in an organic solvent such as a lower alcohol, preferably EtOH, then affords a compound of formula (III'), wherein $R_1$ is alkyl, substituted alkyl, cycloalkyl, substituted cycloalkyl, aryl or substituted aryl, and $R_2$, $R_3$, and $R_4$ have a meaning as defined herein above.

Compounds of formula (IX) are known, or if they are novel they may be prepared using methods well known in the art, or modifications thereof.

A resulting compound of formula (III') may then be converted to a compound (IV'), wherein $R_1$ is alkyl, substituted alkyl, cycloalkyl, substituted cycloalkyl, aryl or substituted aryl, and $R_2$, $R_3$, and $R_4$ have a meaning as defined herein above, by treating a compound (III') with phthalic anhydride in the presence of an acid, such as acetic acid, at an elevated temperature.

Alternatively, compounds of formula (IV'), wherein $R_1$ is aryl or substituted aryl, and $R_2$, $R_3$, and $R_4$ have a meaning as defined herein above, may be obtained by coupling a compound of formula (V), wherein $Hal_1$, $R_2$, $R_3$, and $R_4$ have a meaning as defined herein above, in the presence of a catalyst, preferably a palladium catalyst, e.g., palladium(II)acetate or tetrakis(triphenylphosphine)palladium(0), and a base such as sodium hydroxide (NaOH) or sodium, potassium or cesium carbonate, in an appropriate solvent, e.g., acetonitrile, DMF, dimethoxyethane (DME) or toluene, or a mixture of solvents thereof, with a compound of the formula $$R_1-B(O-R')(O-R'') \quad (V')$$

wherein $R_1$ is aryl or substituted aryl, and R' and R" are hydrogen or lower alkyl, or R' and R" combined are alkylene which together with the boron and the oxygen atoms form a 5- or 6-membered ring, to afford a compound of formula (IV'), wherein $R_1$ is aryl or substituted aryl. Preferably, R' and R" are hydrogen, and the above coupling reaction, i.e., Suzuki reaction, is conducted in toluene in the presence of tetrakis (triphenylphosphine)palladium(0), and potassium carbonate ($K_2CO_3$) at a temperature close to the boiling point of the solvent.

Compounds of formula (V') are known, or if they are novel they may be prepared using methods well known in the art, or modifications thereof.

A resulting compound of formula (IV') may then be halogenated on the methyl group at the 4-position of the thiophene ring to afford a compound of formula (X), wherein $R_1$ is alkyl, substituted alkyl, cycloalkyl, substituted cycloalkyl, aryl or substituted aryl, $R_2$, $R_3$, and $R_4$ have a meaning as defined herein above, and $Hal_2$ represents chloride, bromide or iodide, using methods well known in the art, e.g., by the reaction of a compound of formula (IV') with a halogenating agent, such as an N-halosuccinimide, e.g. N-bromosuccinimide, in the presence of a catalyst such as benzoyl peroxide, and an organic solvent, such as acetonitrile (ACN) or a halogenated hydrocarbon, e.g., carbon tetrachloride or dichloroethane. It should be noted that the halogenation of the methyl group at the 4-position of the thiophene ring of compounds of formula (VI') may be conducted in the absence of a catalyst when ACN is employed as the solvent.

A resulting compound of formula (X) may then be coupled with an amine of formula (VI'), wherein Q has a meaning as defined herein above, in the presence of a base such as TEA, DIEA, NMM, or potassium or cesium carbonate, and an appropriate organic solvent such as DCM, $CHCl_3$ and DMF, to afford a compound of formula (XI), wherein $R_1$ is alkyl, substituted alkyl, cycloalkyl, substituted cycloalkyl, aryl or substituted aryl, and $R_2$, $R_3$, $R_4$, Q have a meaning as defined herein above.

Finally, a compound of formula (XI) may be converted to a compound of formula (I), wherein $R_1$ is alkyl, substituted alkyl, cycloalkyl, substituted cycloalkyl, aryl or substituted aryl, and $R_2$, $R_3$, $R_4$ and Q have a meaning as defined herein above, by removal of the phthalimido protecting group as described herein above.

The processes described herein above may be conducted under inert atmosphere, preferably under nitrogen or argon atmosphere.

In starting compounds and intermediates which are converted to the compounds of the present invention in a manner described herein, functional groups present, such as amino, thiol, carboxyl and hydroxyl groups, are optionally protected by conventional protecting groups that are common in preparative organic chemistry. Protected amino, thiol, carboxyl and hydroxyl groups are those that can be converted under mild conditions into free amino thiol, carboxyl and hydroxyl groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxyl group, amino group, etc.), the structure and stability of the molecule of which the substituent is a part and the reaction conditions.

Well-known protecting groups that meet these conditions and their introduction and removal are described, e.g., in McOmie, "Protective Groups in Organic Chemistry", Plenum Press, London, N.Y. (1973); and Greene and Wuts, "Protective Groups in Organic Synthesis", John Wiley and Sons, Inc., NY (1999).

The above-mentioned reactions are carried out according to standard methods, in the presence or absence of diluent, preferably, such as are inert to the reagents and are solvents thereof, of catalysts, condensing or said other agents, respectively and/or inert atmospheres, at low temperatures, room temperature (RT) or elevated temperatures; preferably at or near the boiling point of the solvents used, and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the reaction components are used in the form of their salts.

Compounds of the invention and intermediates can also be converted into each other according to methods generally known per se.

The present invention also relates to any novel starting materials, intermediates and processes for their manufacture.

Depending on the choice of starting materials and methods, the new compounds may be in the form of one of the possible isomers or mixtures thereof, for example, as substantially pure geometric (cis or trans) isomers, diastereomers, optical isomers, racemates or mixtures thereof. The aforesaid possible isomers or mixtures thereof are within the purview of the present invention.

Any resulting mixtures of isomers can be separated on the basis of the physicochemical differences of the constituents, into the pure geometric or optical isomers, diastereomers, for example, by fractional crystallization and/or chromatography, e.g., by high pressure liquid chromatography (HPLC) using a chiral adsorbent.

Finally, compounds of the invention are either obtained in the free form, or in a salt form thereof, preferably, in a pharmaceutically acceptable salt form thereof.

In particular, compounds of the invention which contain basic groups may be converted into acid addition salts, especially pharmaceutically acceptable acid addition salts. These are formed, e.g., with inorganic acids, such as mineral acids, e.g., sulfuric acid, phosphoric or hydrohalic acid, or with organic carboxylic acids, such as $(C_1$-$C_4)$-alkanecarboxylic acids which, e.g., are unsubstituted or substituted by halogen, e.g., acetic acid, such as saturated or unsaturated dicarboxylic acids, e.g., oxalic, succinic, maleic or fumaric acid, such as hydroxycarboxylic acids, e.g., glycolic, lactic, malic, tartaric or citric acid, such as amino acids, e.g., aspartic or glutamic acid, or with organic sulfonic acids, such as $(C_1$-$C_4)$-alkylsulfonic acids, e.g., methanesulfonic acid; or arylsulfonic acids which are unsubstituted or substituted (for example by halogen). Preferred are salts formed with hydrochloric acid, maleic acid and methanesulfonic acid. Salts may be formed using conventional methods, advantageously in the presence of an ethereal or alcoholic solvent, such as a lower alkohol. From the solutions of the latter, the salts may be precipitated with ethers, e.g., with diethyl ether or petroleum ether. Resulting salts may be converted into the free compounds by treatment with a suitable base, e.g., sodium hydroxide. These or other salts can also be used for the purification of the compounds obtained.

In view of the close relationship between the free compounds and the compounds in the form of their salts, whenever a compound is referred to a corresponding salt is also intended, provided such is possible or appropriate under the circumstances.

The compounds, including their salts, can also be obtained in the form of their hydrates, or include other solvents used for their crystallization.

As described herein above, the compounds of the present invention are allosteric modulators of the $A_1$ adenosine receptor. Thus, the present invention provides a method for the modulation of the $A_1$ adenosine receptor in mammals which method comprises administering to a mammal in need thereof a therapeutically effective amount of a compound of formula (I).

Furthermore, compounds of formula (I) may be employed for the treatment of conditions mediated by the $A_1$ adenosine receptor. Such compounds may, thus, be employed therapeutically for the treatment of pain, in particular, chronic pain such as neuropathic pain, cardiac disease or disorder such as cardiac disarrhythmias, e.g., peroxysmal supraventricular tachycardia, angina, myocardial infarction and stroke, neurological disease or injury, sleep disorders, epilepsy and depression.

In other words, the present invention provides a method for the treatment of conditions mediated by the $A_1$ adenosine receptor, which comprises administering to a mammal in need thereof a therapeutically effective amount of a compound of the present invention.

As used throughout the specification and in the claims, the term "treatment" embraces all the different forms or modes of treatment as known to those of the pertinent art and, in particular, includes preventive, curative, delay of progression and palliative treatment.

The term "therapeutically effective amount" as used herein refers to an amount of a drug or a therapeutic agent that will elicit the desired biological or medical response of a tissue, system or an animal (including man) that is being sought by a researcher or clinician.

The term "mammal" or "patient" are used interchangeably herein and include, but are not limited to, humans, dogs, cats, horses, pigs, cows, monkeys, rabbits, mice and laboratory animals. The preferred mammals are humans.

Preferably, the methods of the present invention are directed to the treatment of pain, including pain management generally, and particularly treatment and management of chronic pain, especially neuropathic pain. Neuropathic pain has been recognized as pain resulting from some type of pathological damage to or condition relating to the nervous system. Various types of neuropathic pain may be treated in accordance with the present invention, e.g., diabetic neuropathy and post herpetic neuralgia. Additional pathological conditions that can give rise to neuropathic pain that may be treated in accordance with the present invention include trigeminal neuralgia, AIDS associated neuropathies due to HIV infection and/or treatment, pain associated with cancer treatment, whip-lash pain, phantom limb pain, traumatic injury pain, complex regional pain syndrome, and pain due to peripheral vascular disease. Furthermore, methods of the present invention will be useful for the management and treatment of post surgical pain.

Preferred methods of the invention also include treatment of cardiac disease or disorder, and ischemia induced injuries, e.g., cardiac disarrhythmias, angina, myocardial infarction, stroke, and the like. Typical subjects for such treatments include, e.g., myocardial infarction, stroke, brain or spinal injury patients, patients undergoing major surgery such as heart surgery where brain ischemia is a potential complication, and the like.

Likewise, the present invention provides a method as defined above comprising co-administration, e.g., concomitantly or in sequence, of a therapeutically effective amount of a compound of formula (I), or a pharmaceutically acceptable salt thereof, and a second drug substance, said second drug substance being a hypolipidemic agent, an anti-inflammatory agent, an anti-hypertensive agent or an opioid analgesic agent, e.g., as indicated herein below.

The present invention further provides pharmaceutical compositions comprising a therapeutically effective amount of a compound of the present invention, alone or in combination with one or more pharmaceutically acceptable carriers.

In carrying out the methods of the present invention, the allosteric adenosine $A_1$ receptor enhancers of the present invention may be formulated into pharmaceutical compositions suitable for administration via a variety of routes, e.g., enteral such as oral or rectal, transdermal, intrathecal and parenteral administration to mammals, including man, for the treatment of conditions mediated by the $A_1$ adenosine receptor. Such conditions include, but are not limited to, pain, in particular, chronic pain such as neuropathic pain, cardiac disease or disorder such as cardiac disarrhythmias, e.g., peroxysmal supraventricular tachycardia, angina, myocardial infarction and stroke, neurological disease or injury, sleep disorders, epilepsy and depression.

For oral administration the pharmaceutical composition comprising an allosteric adenosine $A_1$ receptor enhancer, or a pharmaceutically acceptable salt thereof, can take the form of solutions, suspensions, tablets, pills, capsules, powders, microemulsions, unit dose packets and the like.

Thus, the compounds of the present invention may be employed in the manufacture of pharmaceutical compositions comprising an effective amount thereof in conjunction or admixture with excipients or carriers suitable for administration via a variety of routes, in particular, for enteral or parenteral application. Preferred are tablets and hard or soft shell gelatin capsules comprising the active ingredient together with:

a) diluents, e.g., lactose, dextrose, sucrose, mannitol, sorbitol, cellulose, glycine and/or vegetable oils;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; and if desired d) disintegrants, e.g., starches, agar, alginic acid or its sodium salt, or effervescent mixtures; and/or e) absorbants, colorants, flavors and sweeteners.

Injectable compositions are preferably aqueous isotonic solutions or suspensions, and suppositories are advantageously prepared from fatty emulsions or suspensions.

Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

A unit dosage for a mammal of about 50-70 kg may contain between about 0.005 mg and 2000 mg, advantageously between about 1-1000 mg of the active ingredient. The therapeutically effective dosage of active compound is dependent on the species of warm-blooded animal (mammal), the body weight, age and individual condition, on the form of administration, and on the compound involved.

Accordingly, the present invention provides pharmaceutical compositions as described above for the treatment of conditions mediated by the $A_1$ adenosine receptor including pain, in particular, chronic pain such as neuropathic pain, cardiac disease or disorder such as cardiac disarrhythmias, e.g., peroxysmal supraventricular tachycardia, angina, myocardial infarction and stroke, neurological disease or injury, sleep disorders, epilepsy and depression.

The pharmaceutical compositions may contain a therapeutically effective amount of a compound of the invention as defined above, either alone or in a combination with another therapeutic agent, e.g., each at an effective therapeutic dose as reported in the art. Such therapeutic agents include:

a) hypolipidemic agents such as HMG-CoA (3-hydroxy-3-methyl-glutaryl coenzyme A) reductase inhibitors, squalene synthase inhibitors, FXR (farnesoid X receptor) and LXR (liver X receptor) ligands, cholestyramine, fibrates, nicotinic acid and aspirin;

b) anti-inflammatory agents;

c) anti-hypertensive agents, e.g., loop diuretics, ACE (angiotensin converting enzyme) inhibitors, inhibitors of the Na-K-ATPase membrane pump, NEP (neutral endopeptidase) inhibitors, ACE/NEP inhibitors, angiotensin II antagonists, renin inhibitors, β-adrenergic receptor blockers, inotropic agents, calcium channel blockers, aldosterone receptor antagonists, and aldosterone synthase inhibitors; and d) opioid analgesic agents.

As described above, a compound of the present invention may be administered either simultaneously, before or after the other active ingredient, either separately by the same or different route of administration or together in the same pharmaceutical formulation.

The structure of the therapeutic agents known by their generic or trade names may be taken, e.g., from the actual edition of the standard compendium "The Merck Index" or from databases, e.g., Patents International (e.g. IMS World Publications). Any person skilled in the art is fully enabled to identify the active agents and, based on these references, likewise enabled to manufacture and test the pharmaceutical indications and properties in standard test models, both in vitro and in vivo.

Accordingly, the present invention provides pharmaceutical compositions comprising a therapeutically effective amount of a compound of the invention in combination with another therapeutic agent, preferably selected from hypolipidemic agents, anti-inflammatory agents, anti-hypertensive agents and opioid analgesic agents.

Since the present invention has an aspect that relates to treatment with a combination of compounds which may be co-administered separately, the invention also relates to combining separate pharmaceutical compositions in kit form. The kit comprises two separate pharmaceutical compositions: (1) a composition comprising a compound of formula (I), or a pharmaceutically acceptable salt thereof, plus a pharmaceutically acceptable carrier or diluent; and (2) a composition comprising a hypolipidemic agent, an anti-inflammatory agent, an anti-hypertensive agent, or an opioid analgesic agent, or a pharmaceutically acceptable salt thereof, plus a pharmaceutically acceptable carrier or diluent. The amounts of (1) and (2) are such that, when co-administered separately, a beneficial therapeutic effect(s) is achieved. The kit comprises a container for containing the separate compositions such as a divided bottle or a divided foil packet, wherein each compartment contains a plurality of dosage forms (e.g., tablets) comprising (1) or (2). Alternatively, rather than separating the active ingredient-containing dosage forms, the kit may contain separate compartments each of which contains a whole dosage which in turn comprises separate dosage forms. An example of this type of kit is a blister pack wherein each individual blister contains two (or more) tablets, one (or more) tablet(s) comprising a pharmaceutical composition (1), and the second (or more) tablet(s) comprising a pharmaceutical composition (2). Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician. In the case of the present invention a kit therefore comprises:

(1) a therapeutically effective amount of a composition comprising a compound of formula (I), or a pharmaceutically acceptable salt thereof, and a pharmaceutically acceptable carrier or diluent, in a first dosage form;

(2) a composition comprising a hypolipidemic agent, an anti-inflammatory agent, an anti-hypertensive agent, or an opioid analgesic agent, or a pharmaceutically acceptable salt thereof, in an amount such that, following administration, a beneficial therapeutic effect(s) is achieved, and a pharmaceutically acceptable carrier or diluent, in a second dosage form; and (3) a container for containing said first and second dosage forms.

The present invention further relates to pharmaceutical compositions as described above for use as a medicament.

The present invention further relates to use of pharmaceutical compositions or combinations as described above for the preparation of a medicament for the treatment of conditions mediated by the $A_1$ adenosine receptor including pain, in particular, chronic pain such as neuropathic pain, cardiac disease or disorder such as cardiac disarrhythmias, e.g., peroxysmal supraventricular tachycardia, angina, myocardial infarction and stroke, neurological disease or injury, sleep disorders, epilepsy and depression.

Thus, the present invention also relates to a compound of formula (I) for use as a medicament, to the use of a compound of formula (I) for the preparation of a pharmaceutical composition for the treatment of conditions mediated by the $A_1$ adenosine receptor, and to a pharmaceutical composition for use in conditions mediated by the $A_1$ adenosine receptor comprising a compound of formula (I), or a pharmaceutically acceptable salt thereof, in association with a pharmaceutically acceptable diluent or carrier therefore.

Finally, the present invention provides a method or use which comprises administering a compound of formula (I) in combination with a therapeutically effective amount of a hypolipidemic agent, an anti-inflammatory agent, an anti-hypertensive agent or an opioid analgesic agent.

Ultimately, the present invention provides a method or use which comprises administering a compound of formula (I) in the form of a pharmaceutical composition as described herein.

The above-cited properties are demonstrable in vitro and in vivo tests using advantageously mammals, e.g., mice, rats, dogs, monkeys or isolated organs, tissues and preparations thereof. Said compounds can be applied in vitro in the form of solutions, e.g., preferably aqueous solutions, and in vivo either enterally, parenterally, advantageously intrathecal or intravenously, e.g., as a suspension or in aqueous solution. The dosage in vitro may range between about $10^{-2}$ molar and $10^{-1}$ molar concentrations. A therapeutically effective amount in vivo may range depending on the route of administration, between about 0.000001 mg/kg and 1000 mg/kg, preferably between about 0.00001 mg/kg and 100 mg/kg, more preferably between about 0.001 mg/kg and 10 mg/kg.

The activity of compounds according to the invention may be assessed using methods well-described in the art, e.g., as described herein below:

Membrane Preparation from CHO Cells Transfected with the Human Recombinant $A_1$, $A_{2A}$ and $A_3$ Adenosine Receptors:

The hCHO-$A_1$, hCHO-$A_{2A}$ and hCHO-$A_3$ cell clones are grown adherently and maintained in Dulbecco's modified Eagle's medium with nutrient mixture F12, containing 10% fetal calf serum, penicillin (100 U/mL), streptomycin (100 μg/mL), L-glutamine (2 mM), geneticine (G418, 0.2 mg/mL) at 37° C. in 5% $CO_2$/95% air (Klotz et al. *Naunyn-Schmied. Arch Pharm.* 1998, 357, 1-9). Cells are split two or three times weekly at a ratio of between 1:5 and 1:10. For membrane preparation the culture medium is removed. The cells are washed with PBS and scraped off T75 flasks in ice-cold hypotonic buffer (5 mM Tris HCl, 2 mM EDTA, pH 7.4). The cell suspension is homogenized with Polytron and the homogenate is spun for 10 min at 1,000×g. The supernatant is then centrifuged for 30 min at 100,000×g. The membrane pellet is resuspended in 50 mM Tris HCl buffer pH 7.4 for $A_1$ adenosine receptors, 50 mM Tris HCl buffer pH 7.4, 10 mM $MgCl_2$ for $A_{2A}$ adenosine receptors, 50 mM Tris HCl buffer pH 7.4, 10 mM $MgCl_2$, 1 mM EDTA for $A_3$ adenosine receptors and incubated with 3 UI/mL of adenosine deaminase for 30 min at 37° C. The protein concentration is determined according to a Bio-Rad method (Bradford, 1976) with bovine albumin as a standard reference.

Adenosine Receptor Binding Experiments:

To determine the effect of the compounds of the present invention on the binding to $A_1$, $A_{2A}$ and $A_3$ receptors, membranes from hCHO-$A_1$, hCHO-$A_{2A}$, hCHO-$A_3$ are incubated in a buffer solution in the absence and in the presence of the examined compounds. Test agents are dissolved in DMSO and added to the assay from a 100-fold concentrated solution in DMSO. Control incubations also contain 1% DMSO. Bound and free radioactivity are separated by filtering the assay mixture through Whatman GF/B glass fibre filters using a Micro-mate 196 cell harvester (Packard Instrument Company). The filter bound radioactivity was counted on Top Count Microplate Scintillation Counter (efficacy 57%) with Micro-Scint 20.

Saturation Binding of [$^3$H]CCPA to hCHO-$A_1$:

Saturation binding experiments of [$^3$H]CCPA (0.05 to 20 nM) to human $A_1$ receptors expressed in CHO membranes are performed in triplicate at 25° C. for 1 h in 50 mM Tris-HCl, pH 7.4, in the absence and presence of the tested compounds (10 μM). Non specific binding is defined as binding in the presence of 1 μM R-PIA.

Competition Binding of [$^3$H]CCPA to hCHO-$A_1$:

Competition experiments are carried out in triplicate in a final volume of 250 μL in test tubes containing 1 nM [$^3$H] CCPA, 50 mM Tris-HCl, pH 7.4 and 100 μL of diluted membranes and at least six to eight different concentrations of the tested compounds in the range from 1 nM to 50 μM for 90 min at 25° C. (Baraldi et al. *J. Med. Chem.* 2003, 46, 794-809). Non specific binding is defined as binding in the presence of 1 μM R-PIA. Allosteric enhancement is measured as the action of different concentrations of the tested compounds to increase the specific binding of 1 nM [$^3$H]CCPA to hCHO-$A_1$ membranes.

Competition Binding Experiments:

Competition experiments of 1 nM [$^3$H]DPCPX (Borea et al. *Life Sciences* 1996, 59, 1373-1388), 2 nM [$^3$H]ZM 241385 (Borea et al. *Biochem. Pharmacol.* 1995, 49, 461-469) and 2 nM [$^3$H]MRE 3008F20 (Varani et al. *Mol. Pharmacol.* 2000, 57, 968-975) to hCHO-$A_1$, hCHO-$A_{2A}$ and hCHO-$A_3$ are performed incubating membranes (100 μg of protein/assay) at 25° C. for 90 min, at 4° C. for 60 min and at 4° C. for 150 min, respectively. Competition experiments are performed in duplicate in a final volume of 100 μL in test tubes containing 50 mM Tris HCl buffer (10 mM MgCl$_2$, 1 mM EDTA for $A_3$), pH 7.4 and 100 μL of membranes and at least six to eight different concentrations of the test compound. Non-specific binding is defined as the binding in the presence of 1 μM DPCPX, ZM 241385 and MRE 3008F20 for $A_1$, $A_{2A}$ and $A_3$, respectively, and is about 30% of total binding.

[$^3$H]DPCPX (specific activity, 120 Ci/mmol) and [$^3$H] CCPA (specific activity, 55 Ci/mmol) may be obtained from NEN Research Products (Boston, Mass.); [$^3$H]ZM 241385 (specific activity, 17 Ci/mmol) may be obtained from Tocris Cookson (Bristol, UK); [$^3$H]MRE 3008F20 (specific activity, 67 Ci/mmol) may be obtained from Amersham International (Buckinghamshire, UK).

Measurement of cAMP Enhancement in CHO Cells (Functional Assay):

Allosteric enhancement is measured as the action of a test compound at different concentrations (0.01, 0.1, 1 and 10 μM) to reduce the cAMP content of hCHO-$A_1$ cells. To initiate an experiment, growth medium is removed from the 12-well plates and cells are washed once with warm Hanks' buffered saline. The wash solution is then removed and replaced with fresh Hanks' solution containing forskolin (1 μM), rolipram (20 μM), N$^6$-cyclopentyladenosine (CPA, 0.01 nM), adenosine deaminase (2 U/mL), and the test compound. Forskolin is used to stimulate the activity of adenylyl cyclase, rolipram to inhibit cAMP phosphodiesterase, adenosine deaminase to degrade endogenous adenosine, and CPA to cause a small increase of the number of activated adenosine receptors. After 6 min of incubation at 36° C. in the presence of a test compound, the incubation solution is removed and hydrochloric acid (final concentration 50 mM) is added to terminate drug action. The content of cAMP in acidified extracts of cells is determined by radioimmunoassay as previously described (Kollias-Baker et al. *J. Pharmacol. Exp. Ther.* 1997, 281, 761-768). Because the magnitude of the effects of allosteric modulators on hCHO-$A_1$ cells change subtly with passage number and differ slightly among different aliquots of cells, the actions of the test compounds and the action of a reference compound (PD 81,723) are assessed in each experiment. The effect of each test compound on cAMP content is presented as a percentage of the value of cAMP content in the absence of drug (control, 100%).

Chronic Inflammatory Pain Model:

The intraplantar injection of zymosan-induced mechanical hyperalgesia may be used as a model of chronic inflammatory pain (Meller et al., *Neuropharmacology,* 33:1471-1478, 1994). In this model, typically male Sprague-Dawley or Wistar rats (200-250 g) receives an intraplantar injection of 3 mg/100 μL zymosan into one hind paw. A marked inflammation occurs in this hind paw. Drugs are generally administered for evaluation of efficacy, 24 h after the inflammatory insult, when mechanical hyperalgesia is considered fully established.

Chronic Neuropathic Pain Models:

Two animal models of chronic neuropathic pain may be used that involve some form of peripheral nerve damage. In the Seltzer model (Seltzer et al., *Pain,* 43: 205-218, 1990) Sprague-Dawley or Wistar rats (200-250 g) are anaesthetized and a small incision made mid-way up one thigh (usually the left) to expose the sciatic nerve. The nerve is carefully cleared of surrounding connective tissues at a site near the trochanter just distal to the point at which the posterior biceps semitendinosus nerve branches off the common sciatic nerve. A 7-0 silk suture is inserted into the nerve with a ⅜ curved, reversed-cutting mini-needle, and tightly ligated so that the dorsal ⅓ to ½ of the nerve thickness is held within the ligature. The muscle and skin are closed with sutures and clips and the wound dusted with antibiotic powder. In sham animals the sciatic nerve is exposed but not ligated and the wound closed as in nonsham animals.

In the Chronic Constriction Injury (CCI) model (Bennett, G. J. and Xie, Y. K. *Pain,* 33: 87-107, 1988) rats are anaesthetized and a small incision is made mid-way up one thigh (usually the left) to expose the sciatic nerve. The nerve is cleared of surrounding connective tissue and four ligatures of 4/0 chromic gut are tied loosely around the nerve with approximately 1 mm between each, so that the ligatures just barely constrict the surface of the nerve. The wound is closed with sutures and clips as described above. In sham animals the sciatic nerve is exposed but not ligated and the wound closed as in nonsham animals.

In contrast to the Seltzer and CCI models, the Chung model involves ligation of the spinal nerve (Kim, S. O. and Chung, J. M. *Pain,* 50: 355-363, 1992). In this model, Sprague-Dawley or Wistar rats (200-250 g) are anesthetized and placed into a prone position and an incision is made to the left of the spine at the L4-S2 level. A deep dissection through the paraspinal muscles and separation of the muscles from the spinal processes at the L4-S2 level will reveal part of the sciatic nerve as it branches to form the L4, L5 and L6 spinal nerves. The L6 transverse process is carefully removed with a small rongeur enabling visualization of these spinal nerves. The L5 spinal nerve is isolated and tightly ligated with 7-0 silk suture. The wound is closed with a single muscle suture (6-D silk) and one or two skin closure clips and dusted with antibiotic powder. In sham animals the L5 nerve is exposed as before but not ligated and the wound closed as before.

Behavioral Index:

In all chronic pain models (inflammatory and neuropathic) mechanical hyperalgesia is assessed by measuring paw withdrawal thresholds of both hind paws to an increasing pressure stimulus using an Analgesymeter. Mechanical allodynia is assessed by measuring withdrawal thresholds to non-noxious mechanical stimuli applied with von Frey hairs to the planter surface of both hind paws. Thermal hyperalgesia is assessed by measuring withdrawal latencies to a noxious thermal stimulus applied to the underside of each hind paw. With all models, mechanical hyperalgesia and allodynia and thermal hyperalgesia develop within 1-3 days following surgery and persist for at least 50 days. For the assays described herein, drugs may be applied before and after surgery to assess their effect on the development of hyperalgesia, approximately 14 days following surgery, to determine their ability to reverse established hyperalgesia.

The percentage reversal of hyperalgesia is calculated as follows:

$$\% \ reversal = \frac{postdose\ threshold - predose\ threshold}{naive\ threshold - predose\ threshold} \times 100$$

In the above described pain models, all surgery may be performed under enflurane/$O_2$ inhalation anesthesia. In all cases the wound is closed after the procedure and the animals are allowed to recover. In all pain models employed, after a few days, in all but the sham operated animals, a marked mechanical and thermal hyperalgesia and allodynia develops in which there is a lowering of pain threshold and an enhanced reflex withdrawal response of the hind paw to touch, pressure or thermal stimuli. After surgery, the animals may also exhibit characteristic changes to the affected paw. In the majority of animals the toes of the affected hind paw are held together and the foot is turned slightly to one side, and in some rats the toes are also curled under. The gait of the ligated rats varies, but limping is uncommon. Some rats are seen to raise the affected hind paw from the cage floor and demonstrate an unusual rigid extension of the hind limb when held. The rats tend to be very sensitive to touch and may vocalize. Otherwise the general health and condition of the rats is good.

Illustrative of the invention, the compound of Example 4 demonstrates an $IC_{50}$ value of about 100 nM in a functional assay measuring the cAMP level in CHO cells expressing the human $A_1$-adenosine receptor. Furthermore, the compound of Example 4 increases the $B_{MAX}$ value of the agonist [$^3$H] CCPA to human $A_1$ adenosine receptors up to 600% at 10 μM concentration. Likewise, the compound of Example 60 exhibits about 6-fold increase in the $B_{MAX}$ value of the agonist [$^3$H]CCPA.

The following Examples are intended to illustrate the invention and are not to be construed as being limitations thereon. If not mentioned otherwise, all evaporations are performed under reduced pressure, preferably between about 10 mmHg and 100 mmHg. The structure of final products, intermediates and starting materials is confirmed by standard analytical methods, e.g., microanalysis, melting point (m.p.) and spectroscopic characteristics, e.g., MS, IR and NMR. Abbreviations used are those conventional in the art.

EXAMPLE 1

{2-Amino-4-[(4-phenylpiperazin-1-yl)methyl]thiophen-3-yl}(4-chlorophenyl)methanone

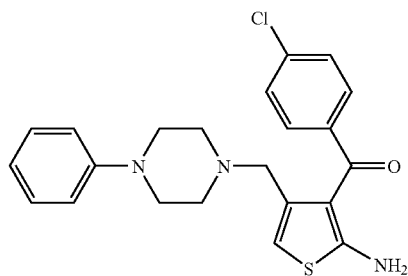

A. (2-Amino-4-methylthiophen-3-yl)(4-chlorophenyl)methanone

To a suspension of 3-(4-chlorophenyl)-3-oxo-propionitrile (900 mg, 5 mmol) and 2,5-dimethyl-[1,4]dithiane-2,5-diol (450 mg, 2.5 mmol) in absolute EtOH (10 mL), cooled in a bath of water/ice (4° C.), is added TEA (5 mmol, 0.7 mL). After stirring for 10 min at RT, the mixture is refluxed for 2 h. The resulting red-brown solution is cooled and concentrated, and the residue dissolved in EtOAc (10 mL). The organic phase is subsequently washed with 1% w/v aqueous HCl (5 mL), a saturated solution of NaHCO$_3$ (5 mL), water (5 mL) and brine (5 mL), dried (Na$_2$SO$_4$) and concentrated to give a brown residue. The residue is suspended in ethyl ether (15 mL), the suspension stirred for 30 min and filtered. The filtrate is concentrated, suspended with petroleum ether and the resulting suspension is stirred for 30 min and filtered. The filtrate is concentrated, and the residue is purified by column chromatography using a mixture of EtOAc-petroleum ether 2-8 as eluent to give (2-amino-4-methylthiophen-3-yl)(4-chlorophenyl)methanone as an orange solid: m.p. 148-150° C. $^1$H NMR (CDCl$_3$) δ: 1.66 (s, 3H), 5.85 (s, 1H), 6.61 (br s, 2H), 7.38 (d, J=6.4 Hz, 2H), 7.45 (d, J=6.4 Hz, 2H); IR (KBr) cm$^{-1}$: 3345, 1589, 1435, 1267.

B. 2-[3-(4-Chlorobenzoyl)-4-methylthiophen-2-yl]isoindoline-1,3-dione

The title A compound (755 mg, 3 mmol) is dissolved in acetic acid (20 mL), then to the solution is added phthalic anhydride (3.6 mmol, 533 mg) and the mixture is heated under reflux for 15 h. The solvent is evaporated and the residual material is dissolved in ethyl acetate (20 mL). The organic solution is washed with a saturated solution of NaHCO$_3$ (5 mL), water (5 mL) and brine (5 mL), dried (Na$_2$SO$_4$) and concentrated. The residue is stirred for 1 h with petroleum ether (20 mL), and the solids are collected by filtration to afford 2-[3-(4-chlorobenzoyl)-4-methylthiophen-2-yl]isoindoline-1,3-dione as a brown powder: $^1$H NMR (CDCl$_3$) δ: 2.24 (s, 3H), 7.02 (s, 1H), 7.22 (d, J=7.2 Hz, 2H), 7.62-8.00 (m, 6H).

C. 2-[5-Bromo-3-(4-chlorobenzoyl)-4-methylthiophen-2-yl]isoindole-1,3-dione

To a solution of the title B compound (20 mmol, 7.6 g) in benzene (150 mL) is added benzoyl peroxide (484 mg, 2 mmol) and the mixture is heated under reflux. At refluxing conditions, a mixture of N-bromosuccinimide (20 mmol, 3.56 g) and benzoyl peroxide (484 mg, 2 mmol) is added and the mixture is refluxed for 6 h further. The solvent is removed under reduced pressure, and the residue is dissolved in EtOAc (330 mL). The organic solution is subsequently washed a saturated solution of NaHCO$_3$ (200 mL), water (50 mL) and brine (50 mL), dried (Na$_2$SO$_4$) and concentrated to give a brown powder. The powder is suspended with petroleum ether (200 mL), the mixture is stirred for 30 min and the solids are collected by filtration to afford 2-[5-bromo-3-(4-chlorobenzoyl)-4-methylthiophen-2-yl]isoindoline-1,3-dione which is used as such in the next step without further purification: m.p. 194-195° C. $^1$H NMR (CDCl$_3$) δ: 2.09 (s, 3H), 7.19 (d, J=7.4 Hz, 2H), 7.62-7.71 (m, 6H); IR (KBr) cm$^{-1}$: 1728, 1664, 1587, 1368, 717.

D. 2-[5-Bromo-4-bromomethyl-3-(4-chlorobenzoyl)thiophen-2-yl]isoindole-1,3-dione To a suspension of the title C compound (20 mmol, 9.2 g) in CCl$_4$ (150 mL) is added benzoyl peroxide (242 mg, 1 mmol) and the mixture is heated under reflux. At refluxing conditions, a mixture of N-bromosuccinimide (20 mmol, 3.56 g) and benzoyl peroxide (242 mg, 1 mmol) is added and the mixture is refluxed for 1 h further. After this time, if the reaction is not finished, a mixture of N-bromosuccinimide (2 mmol, 356 mg) and benzoyl peroxide (242 mg, 1 mmol) is added and the mixture is refluxed for another h. The resulting yellow solution is cooled to RT and the precipitated succinimide is removed by filtration and washed with CCl$_4$ (25 mL). The filtrate is washed with 5% NaHCO$_3$ solution (50 mL), water (50 mL) and brine (50 mL), dried (Na$_2$SO$_4$) and concentrated to give a yellow powder. The powder is suspended with petroleum ether (100 mL), the mixture is stirred for 30 min and the solids are collected by filtration to give 2-[5-bromo-4-bromomethyl-3-(4-chlorobenzoyl)thiophen-2-yl]isoindoline-1,3-dione as a yellow solid: m.p. 173-175° C. $^1$H NMR (CDCl$_3$) δ: 4.65 (s, 2H), 7.20 (d, J=6.6 Hz 2H), 7.66 (d, J=6.6 Hz, 2H), 7.62-7.71 (m, 4H). IR (KBr) cm$^{-1}$: 1727, 1658, 1348, 1330, 1084.

E. 2-[5-Bromo-3-(4-chlorobenzoyl)-4-((4-phenylpiperazin-1-yl)methyl)thiophen-2-yl]isoindoline-1,3-dione To a stirred solution of the title D compound (900 mg, 1.6 mmol) in dry DCM (5 mL) is added TEA (1.1 equiv., 1.76 mmol, 243 mg). The mixture is cooled with a bath of ice/water, and 4-phenylpiperazine (3 equiv., 5 mmol, 810 mg) is added. The mixture is stirred at RT for 2 h, diluted with DCM (5 mL), washed with water (5 mL) and brine (5 mL). The organic layer is dried (Na$_2$SO$_4$) and concentrated in vacuo to give a brown residue which is purified by column chromatography (EtOAc-petroleum ether 4-6 as eluent) to afford 2-[5-bromo-3-(4-chlorobenzoyl)-4-((4-phenyl-piperazin-1-yl)methyl)thiophen-2-yl]isoindoline-1,3-dione as a yellow solid: m.p. 186-193° C. $^1$H NMR (CDCl$_3$) δ: 2.85 (t, J=5.0 Hz, 2H), 3.14 (s, 2H), 3.34 (t, J=5.0 Hz, 2H), 3.42 (t, J=5.2 Hz, 2H), 3.94 (t, J=5.2 Hz, 2H), 6.80-6.93 (m, 4H), 6.93-7.28 (m, 4H), 7.39 (d, J=8.4 Hz, 2H), 7.58-7.62 (m, 2H), 7.82 (d, J=6.8 Hz, 1H).

F. 2-[3-(4-Chlorobenzoyl)-4-((4-phenylpiperazin-1-yl)methyl)thiophen-2-yl]isoindoline-1,3-dione A solution of the title E compound (2 mmol) in DMF (20 mL), containing Et$_3$N (0.3 mL, 2 mmol, 1 equiv) is hydrogenated over 120 mg of 10% Pd/C at 60 psi for 3 h. The catalyst is removed by filtration, the filtrate is concentrated. The residue is dissolved in DCM (20 mL), washed with water (5 mL) and brine (5 mL), and dried (Na$_2$SO$_4$). The solvent is removed under reduced pressure and the residue is purified by column chromatography (EtOAc-DCM 2-8 as eluent) to afford 2-[3-(4-chloro-benzoyl)-4-((4-phenylpiperazin-1-yl)methyl)thiophen-2-yl]isoindoline-1,3-dione as a white solid: m.p. 220-222° C. $^1$H NMR (CDCl$_3$) δ: 2.92 (t, J=5.0 Hz, 2H), 3.14 (s, 2H), 3.34 (t, J=5.0 Hz, 2H), 3.44 (t, J=5.2 Hz, 2H), 3.94 (t, J=5.2 Hz, 2H), 6.69 (s, 1H), 6.87 (d, J=6.8 Hz, 2H), 7.21 (d, J=6.8 Hz, 2H), 7.37-7.52 (m, 4H), 7.52 (t, J=6.8 Hz, 1H), 7.58-7.60 (m. 3H), 7.83 (d, J=6.8 Hz, 1H).

G. {2-Amino-4-[(4-phenylpiperazin-1-yl)methyl]thiophen-3-yl}(4-chlorophenyl)methanone A stirred suspension of the title F compound (0.5 mmol) and 100% hydrazine monohydrate (1.2 eq, 0.6 mmol, 29 μL) in absolute ethanol (10 mL) is heated at reflux for 3 h. After this time, the resulting solution is left at RT for 1 h. The reaction is finished after the complete solubilization of the starting material. The solvent is evaporated and the residue is partitioned between EtOAc (10 mL) and water (5 mL). The organic phase is separated, washed with brine (2 mL), dried and concentrated in vacuo. The residue is purified by column chromatography (EtOAc-DCM/2-8 as eluent) to give {2-amino-4-[(4-phenylpiperazin-1-yl)methyl]thiophen-3-yl}(4-chlorophenyl)methanone as a yellow solid: m.p. 112° C. $^1$H NMR (CDCl$_3$) δ: 2.04 (m, 4H), 2.94 (m. 4H), 3.00 (s, 2H), 6.07 (br s, 2H), 6.14 (s, 1H), 6.83 (m, 3H), 7.23 (m, 2H), 7.35 (d, J=8.4 Hz, 2H), 7.55 (d, J=8.4 Hz, 2H).

The following compounds are prepared analogously as described in Example 1.

EXAMPLE 2

{2-Amino-4-[(4-methylpiperazin-1-yl)methyl]thiophen-3-yl}(4-chlorophenyl)methanone

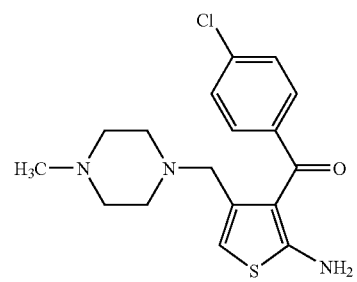

The title compound is purified by column chromatography (MeOH as eluent). Yellow oil.

$^1$H NMR (CDCl$_3$) δ: 2.24 (s, 3H), 2.32 2.44 (m, 6H), 3.37 (t, J=5.4 Hz, 2H), 3.58 (t, J=5.4 Hz, 2H), 6.10 (m, 3H), 7.34 (d, J=8.4 Hz, 2H), 7.52 (d, J=8.4 Hz, 2H).

EXAMPLE 3

{2-Amino-4-[4-((4-fluorophenyl)piperazin-1-yl)methyl]thiophen-3-yl}(4-chlorophenyl)methanone

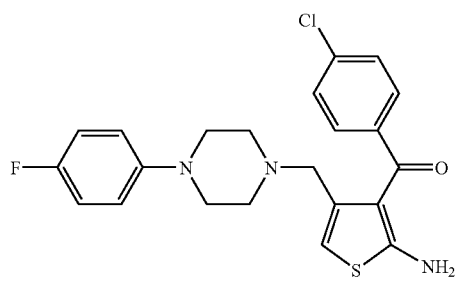

The title compound is purified by column chromatography (EtOAc:DCM/2:8 as eluent). Yellow solid, m.p. 70-72° C. $^1$H NMR (CDCl$_3$) δ: 2.04 (t, J=5.2 Hz, 4H), 2.85 (t, J=5.2 Hz, 4H), 3.00 (s, 2H), 6.06 (s, 2H), 6.13 (s, 1H), 6.82 (m, 2H), 6.92 (t, J=9.0 Hz, 2H), 7.38 (d, J=8.2 Hz, 2H), 7.56 (d, J=8.2 Hz, 2H). IR (KBr) cm$^{-1}$: 3421, 1587, 1509, 1262, 1087.

EXAMPLE 4

{2-Amino-4-[4-((4-chlorophenyl)piperazin-1-yl)methyl]thiophen-3-yl}(4-chlorophenyl)methanone

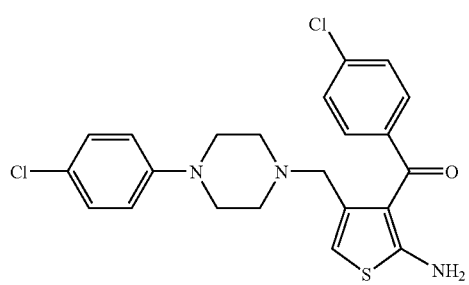

The title compound is purified by column chromatography (EtOAc:DCM/1:9 as eluent). Yellow solid, m.p. 148-150° C. $^1$H NMR (CDCl$_3$) δ: 2.04 (t, J=4.6 Hz, 4H), 2.88 (t, J=4.6 Hz, 4H), 3.00 (s, 2H), 6.07 (br s, 2H), 6.13 (s, 1H), 6.74 (d, J=9.2 Hz, 2H), 7.19 (d, J=9.0 Hz, 2H), 7.39 (d, J=8.4 Hz, 2H), 7.55 (d, J=8.4 Hz, 2H). IR (KBr) cm$^{-1}$: 3366, 1591, 1498, 1426, 1234, 1085, 815.

EXAMPLE 5

{2-Amino-4-[4-((4-methoxyphenyl)piperazin-1-yl)methyl]thiophen-3-yl}(4-chlorophenyl)methanone

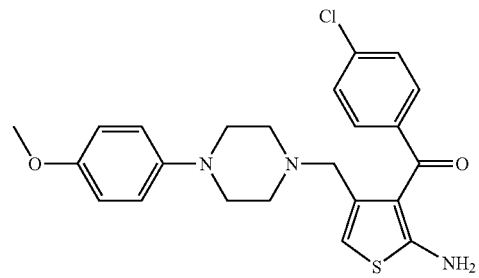

The title compound is purified by column chromatography (EtOAc:DCM/2:8 as eluent). Yellow oil. $^1$H NMR (CDCl$_3$) δ: 2.04 (t, J=5.4 Hz, 4H), 2.83 (t, J=5.4 Hz, 4H), 3.10 (s, 2H), 3.75 (s, 3H), 6.08 (br s, 2H), 6.14 (s, 1H), 6.82 (d, J=10.2 Hz, 2H), 6.86 (d, J=10.2 Hz, 2H), 7.36 (d, J=8.4 Hz, 2H), 7.55 (d, J=8.4 Hz, 2H). IR (KBr) cm$^{-1}$: 3366, 1591, 1498, 1426, 1234, 1085, 815.

EXAMPLE 6

{2-Amino-4-[(4-p-tolylpiperazin-1-yl)methyl]thiophen-3-yl}(4-chlorophenyl)methanone

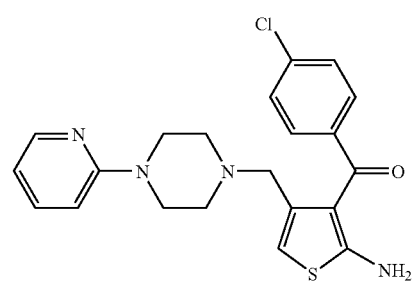

The title compound is purified by column chromatography (EtOAc:DCM/1:9 as eluent). Yellow solid, m.p. 73-75° C. $^1$H NMR (CDCl$_3$) δ: 2.26 (s, 3H), 2.32 (t, J=5.6 Hz, 4H), 2.86 (t, J=5.6 Hz, 4H), 3.12 (s, 2H), 6.10 (br s, 2H), 6.13 (s, 1H), 6.83 (d, J=8.0 Hz, 2H), 7.08 (d, J=8.0 Hz, 2H), 7.32 (d, J=8.2 Hz, 2H), 7.43 (d, J=8.2 Hz, 2H). IR (KBr) cm$^{-1}$: 1722, 1614, 1514, 1261, 1089, 1021.

EXAMPLE 7

{2-Amino-4-[(4-(pyridin-2-yl)piperazin-1-yl)methyl]thiophen-3-yl}(4-chlorophenyl)methanone The title compound is purified by column chromatography (EtOAc:DCM/4:6 as eluent). Yellow solid, m.p. 130-131° C. $^1$H NMR (CDCl$_3$) δ: 2.01 (t, J=5.0 Hz, 4H), 3.00 (s, 2H), 3.27 (t, J=5.0 Hz, 4H), 6.09 (br s, 2H), 6.13 (s, 1H), 6.53-6.61 (m, 3H), 7.40 (d, J=6.6 Hz, 2H), 7.57 (d, J=6.6 Hz, 2H), 8.15 (m, 1H). IR (KBr) cm$^1$: 2963, 1595, 1434, 1261, 1096, 1022.

EXAMPLE 8

{2-Amino-4-[(4-(pyrimidin-2-yl)piperazin-1-yl)methyl]thiophen-3-yl}(4-chlorophenyl)methanone

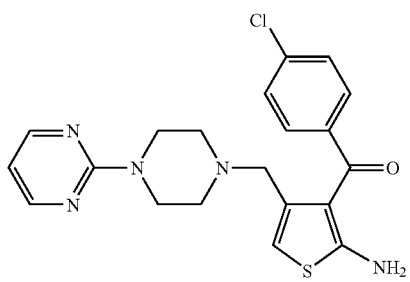

The title compound is purified by column chromatography (EtOAc:DCM/1:1 as eluent). Yellow solid, m.p. 141-143° C. $^1$H NMR (CDCl$_3$) δ: 1.95 (t, J=4.8 Hz, 4H), 2.99 (s, 2H), 3.55 (t, J=4.8 Hz, 4H), 6.13 (br s, 3H), 6.44 (t, J=4.8 Hz, 1H), 7.40 (d, J=8.2 Hz, 2H), 7.53 (d, J=8.2 Hz, 2H), 8.26 (d, J=4.8 Hz, 2H). IR (KBr) cm$^{-1}$: 3386, 1712, 1586, 1423, 1260, 1084, 798.

EXAMPLE 9

{2-Amino-4-[(4-(3,4-dichlorophenyl)piperazin-1-yl)methyl]thiophen-3-yl}(4-chlorophenyl)methanone

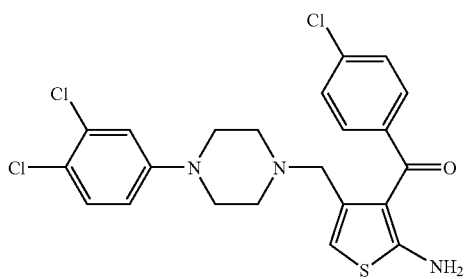

The title compound is purified by column chromatography (EtOAc:DCM/1:9 as eluent). Yellow solid, m.p. 102-104° C. $^1$H NMR (CDCl$_3$) δ: 2.04 (t, J=4.6 Hz, 4H), 2.90 (t, J=4.6 Hz, 4H), 3.00 (s, 2H), 6.08 (br s, 2H), 6.13 (s, 1H), 6.66 (dd, J=9.0 and 2.8 Hz, 1H), 6.87 (d, J=2.8 Hz, 1H), 7.21 (s, 1H), 7.40 (d, J=8.6 Hz, 2H), 7.56 (d, J=8.6 Hz, 2H). IR (KBr) cm$^{-1}$: 2964, 1591, 1435, 1262, 1096, 1020, 800.

EXAMPLE 10

4-{4-[(5-Amino-4-(4-chlorobenzoyl)thiophen-3-yl)methyl]piperazin-1-yl}benzonitrile

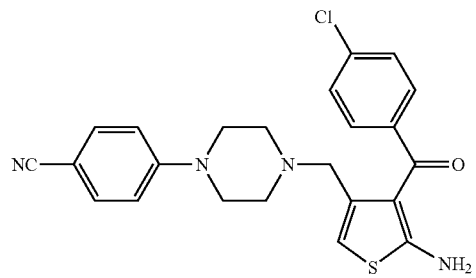

The title compound is purified by column chromatography (EtOAc:DCM/1:9 as eluent). Yellow solid, m.p. 173-175° C. $^1$H NMR (CDCl$_3$) δ: 2.01 (t, J=4.8 Hz, 4H), 3.03 (s, 2H), 3.08 (t, J=4.8 Hz, 4H), 6.08 (br s, 2H), 6.14 (s, 1H), 6.78 (d, J=9.0 Hz, 2H), 7.36 (d, J=7.8 Hz, 2H), 7.43 (d, J=9.0 Hz, 2H), 7.56 (d, J=7.8 Hz, 2H). IR (KBr) cm$^{-1}$: 2963, 1606, 1261, 1097, 1016, 808.

EXAMPLE 11

{2-Amino-4-[(4-(3-chlorophenyl)piperazin-1-yl)methyl]thiophen-3-yl}(4-chlorophenyl)methanone

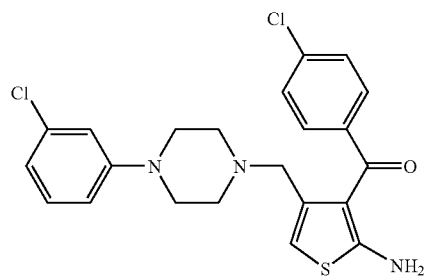

The title compound is purified by column chromatography (EtOAc:DCM/1:9 as eluent). Yellow solid, m.p. 197-199° C. $^1$H NMR (CDCl$_3$) δ: 2.01 (t, J=5.2 Hz, 4H), 2.93 (t, J=5.2 Hz, 4H), 3.00 (s, 2H), 6.08 (br s, 2H), 6.13 (s, 1H), 6.68 (d, J=7.6 Hz, 1H), 6.78 (d, J=7.6 Hz, 1H), 6.81 (s, 1H), 7.12 (t, J=8.0 Hz, 1H), 7.37 (d, J=8.4 Hz, 2H), 7.55 (d, J=8.4 Hz, 2H). IR (KBr) cm$^{-1}$: 3356, 1587, 1512, 1430 and 1076.

EXAMPLE 12

{2-Amino-4-[(4-(2-chlorophenyl)piperazin-1-yl)methyl]thiophen-3-yl}(4-chlorophenyl)methanone

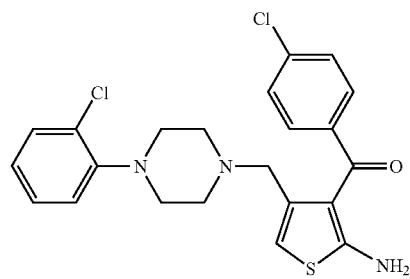

The title compound is purified by column chromatography (EtOAc:DCM/1:9 as eluent). Yellow solid, m.p. 115-117° C. $^1$H NMR (CDCl$_3$) δ: 2.04 (t, J=5.2 Hz, 4H), 2.78 (t, J=5.2 Hz, 4H), 3.10 (s, 2H), 6.06 (br s, 2H), 6.11 (s, 1H), 6.60 (d, J=7.4 Hz, 1H), 6.72 (d, J=7.4 Hz, 1H), 6.80 (t, J=7.4 Hz, 1H), 7.02 (t, J=7.4 Hz, 1H), 7.42 (d, J=8.2 Hz, 2H), 7.52 (d, J=8.2 Hz, 2H). IR (KBr) cm$^{-1}$: 3342, 1578, 1534, 1432 and 1084.

EXAMPLE 13

{2-Amino-4-[(4-(2-fluorophenyl)piperazin-1-yl)methyl]thiophen-3-yl}(4-chlorophenyl)methanone

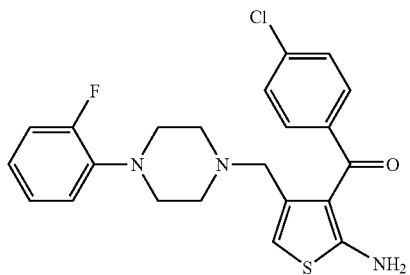

The title compound is purified by column chromatography (EtOAc:DCM/1:9 as eluent). Yellow solid, m.p. 102-104° C. $^1$H NMR (CDCl$_3$) δ: 2.04 (t, J=5.2 Hz, 4H), 2.86 (t, J=5.2 Hz, 4H), 3.02 (s, 2H), 6.04 (s, 2H), 6.12 (s, 1H), 6.74 (d, J=7.8 Hz, 1H), 6.82 (d, J=7.8 Hz, 1H), 6.86 (t, J=7.6 Hz, 1H), 6.92 (t, J=7.6 Hz, 1H), 7.38 (d, J=8.2 Hz, 2H), 7.54 (d, J=8.2 Hz, 2H). IR (KBr) cm$^{-1}$: 3417, 1578, 1512, 1264, 1092.

EXAMPLE 14

{2-Amino-4-[(4-(3-(trifluoromethyl)phenyl)piperazin-1-yl)methyl]thiophen-3-yl}(4-chlorophenyl)methanone

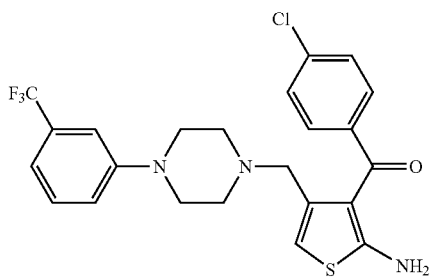

The title compound is purified by column chromatography (EtOAc:DCM/0.5:9.5 as eluent). Yellow solid, m.p. 167-169° C. $^1$H NMR (CDCl$_3$) δ: 2.04 (t, J=5.2 Hz, 4H), 2.97 (t, J=5.2 Hz, 4H), 3.00 (s, 2H), 6.07 (br s, 2H), 6.14 (s, 1H), 7.01 (m, 3H), 7.26 (t, J=9.6 Hz, 1H), 7.38 (d, J=8.4 Hz, 2H), 7.54 (d, J=8.4 Hz, 2H). IR (KBr) cm$^{-1}$: 3346, 1578, 1522, 1424 and 1082.

EXAMPLE 15

1-{4-[(5-Amino-4-(4-chlorobenzoyl)thiophen-3-yl)methyl]piperazin-1-yl}-2-(4-chlorophenyl)ethanone The title compound is purified by column chromatography (EtOAc:DCM/2:8 as eluent). Yellow solid, m.p. 60-61° C. $^1$H NMR (CDCl$_3$) δ: 1.73 (t, J=4.8 Hz, 2H), 1.78 (t, J=4.8 Hz, 2H), 2.93 (s, 2H), 3.19 (t, J=5.2 Hz, 2H), 3.64 (t, J=5.2 Hz, 2H), 3.59 (s, 2H), 6.06 (s, 1H), 6.09 (s, 2H), 7.10 (d, J=8.4 Hz, 2H), 7.28 (d, J=8.4 Hz, 2H), 7.39 (d, J=8.6 Hz, 2H), 7.53 (d, J=8.6 Hz, 2H). IR (KBr) cm$^{-1}$: 3342, 1578, 1502, 1442 and 1082.

EXAMPLE 16

{2-Amino-4-[(4-(4-chlorobenzoyl)piperazin-1-yl)methyl]thiophen-3-yl}(4-chlorophenyl)methanone

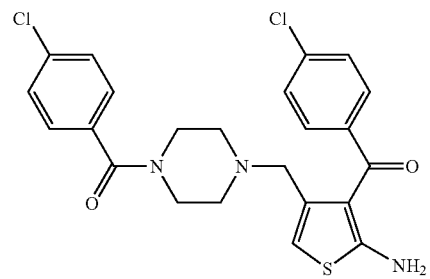

The title compound is purified by column chromatography (EtOAc:DCM/1:9 as eluent). Yellow solid, m.p. 185-186° C. $^1$H NMR (CDCl$_3$) δ: 1.83 (t, J=4.8 Hz, 2H), 1.92 (t, J=4.8 Hz, 2H), 2.99 (s, 2H), 3.15 (t, J=5.0 Hz, 2H), 3.49 (t, J=5.0 Hz, 2H), 6.08 (s, 1H), 6.10 (s, 2H), 7.24 (d, J=8.2 Hz, 2H), 7.28 (d, J=8.2 Hz, 2H), 7.36 (d, J=8.2 Hz, 2H), 7.54 (d, J=8.2 Hz, 2H). IR (KBr) cm$^{-1}$: 3352, 1564, 1512, 1434 and 1068.

EXAMPLE 17

{2-Amino-4-[(4-(pyridin-4-yl)piperazin-1-yl)methyl]thiophen-3-yl}(4-chlorophenyl)methanone

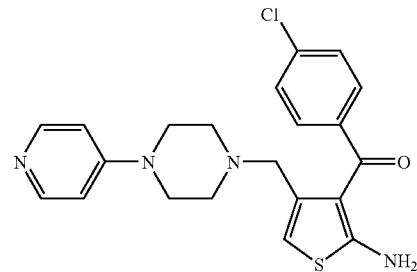

The title compound is purified by column chromatography (EtOAc:MeOH/7:3 as eluent). Yellow solid, m.p. 86-88° C. $^1$H NMR (CDCl$_3$) δ: 2.01 (t, J=5.2 Hz, 4H), 3.00 (s, 2H), 3.24 (t, J=5.2 Hz, 4H), 6.09 (br s, 2H), 6.12 (s, 1H), 6.72 (d, J=5.6 Hz, 2H), 6.87 (d, J=5.6 Hz, 2H), 8.06 (d, J=7.4 Hz, 2H), 8.19 (d, J=7.4 Hz, 2H). IR (KBr) cm$^{-1}$: 2956, 1578, 1445, 1256, 1077, 1012.

EXAMPLE 18

{2-Amino-4-[(4-(benzo[d][1,3]dioxol-5-yl)piperazin-1-yl)methyl]thiophen-3-yl}(4-chlorophenyl)methanone

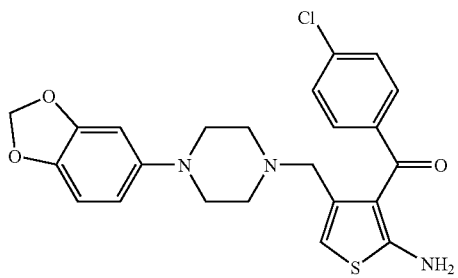

The title compound is purified by column chromatography (EtOAc:DCM/1:1 as eluent). Yellow solid, m.p. 85-86° C. $^1$H NMR (CDCl$_3$) δ: 2.38 (t, J=5.2 Hz, 4H), 2.66 (t, J=5.2 Hz, 4H), 3.34 (s, 2H), 5.72 (s, 2H), 5.84 (s, 2H), 5.86 (dd, J=8.2 and 2.4 Hz, 1H), 6.05 (d, J=2.2 Hz, 1H), 6.24 (d, J=2.2 Hz, 1H), 6.65 (d, J=8.2 Hz, 1H), 7.20 (d, J=8.4 Hz, 2H), 7.54 (d, J=8.4 Hz, 2H). IR (KBr) cm$^{-1}$: 3376, 1577, 1532, 1423 and 1054.

EXAMPLE 19

{2-Amino-4-[(4-(2,3-dichlorophenyl)piperazin-1-yl)methyl]thiophen-3-yl}(4-chlorophenyl)methanone

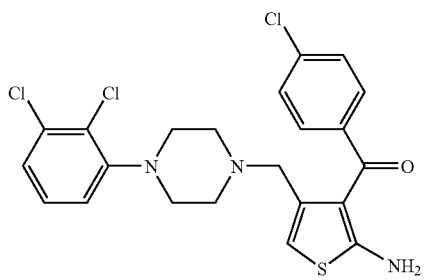

The title compound is purified by column chromatography (EtOAc:DCM/1:9 as eluent). Yellow oil. $^1$H NMR (CDCl$_3$) δ: 2.05 (t, J=4.4 Hz, 4H), 2.78 (t, J=4.4 Hz, 4H), 3.01 (s, 2H), 6.07 (br s, 2H), 6.14 (s, 1H), 6.89 (d, J=4.8 Hz, 1H), 7.11 (d, J=5.2 Hz, 2H), 7.58 (d J=8.6 Hz, 2H). IR (KBr) cm$^{-1}$: 2978, 1578, 1452, 1267, 1078, 1012.

EXAMPLE 20

{2-Amino-4-[(4-(3-fluorophenyl)piperazin-1-yl)methyl]thiophen-3-yl}(4-chlorophenyl)methanone

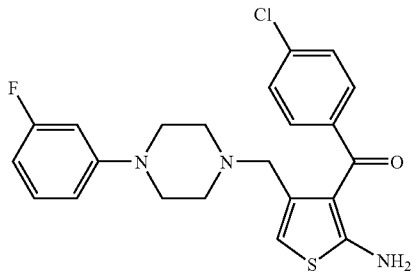

The title compound is purified by column chromatography (EtOAc:DCM/2:8 as eluent). Yellow solid, m.p. 150-152° C. $^1$H NMR (CDCl$_3$) δ: 2.02 (t, J=4.8 Hz, 4H), 2.93 (t, J=4.8 Hz, 4H), 3.00 (s, 2H), 6.08 (s, 2H), 6.13 (s, 1H), 6.45 (t, J=7.0 Hz, 1H), 6.53 (m, 2H), 7.17 (q, J=7.6 Hz, 1H), 7.40 (d, J=8.2 Hz, 2H), 7.56 (d, J=8.2 Hz, 2H). IR (KBr) cm$^{-1}$: 3434, 1577, 1534, 1256, 1077.

EXAMPLE 21

{2-Amino-4-[(4-(3,5-dichlorophenyl)piperazin-1-yl)methyl]thiophen-3-yl}(4-chlorophenyl)methanone

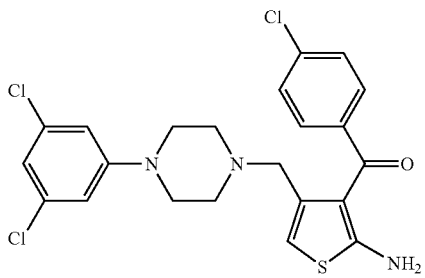

The title compound is purified by column chromatography (EtOAc:DCM/1:9 as eluent). Yellow solid, m.p. 185-187° C. $^1$H NMR (CDCl$_3$) δ: 1.99 (t, J=4.8 Hz, 4H), 2.92 (t, J=4.8 Hz, 4H), 2.99 (s, 2H), 6.09 (br s, 2H), 6.13 (s, 1H), 6.64 (s, 2H), 6.76 (s, 1H), 7.38 (d, J=8.6 Hz, 2H), 7.53 (d, J=8.6 Hz, 2H). IR (KBr) cm$^{-1}$: 2965, 1587, 1444, 1272, 1085 and 1033.

EXAMPLE 22

{2-Amino-4-[(4-(4-(trifluoromethyl)phenyl)piperazin-1-yl)methyl]thiophen-3-yl}(4-chlorophenyl)methanone

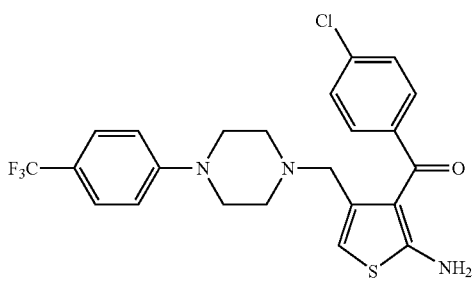

EXAMPLE 23

2-{4-[(5-Amino-4-(4-chlorobenzoyl)thiophen-3-yl)methyl]piperazin-1-yl}-1-(4-chlorophenyl)ethanone

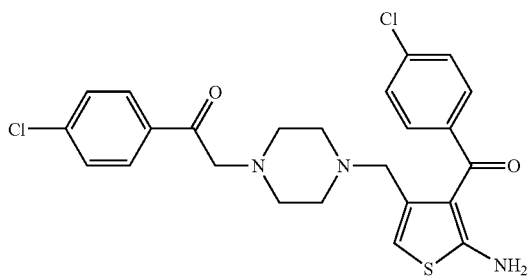

The title compound is purified by column chromatography (EtOAc:MeOH/9.5:0.5 as eluent). Yellow solid, m.p. 77-78° C. $^1$H NMR (CDCl$_3$) δ: 2.73 (t, J=4.8 Hz, 4H), 3.42 (t, J=4.8 Hz, 4H), 3.56 (s, 2H), 3.72 (s, 2H), 6.06 (br s, 2H), 6.08 (s, 1H), 7.22 (d, J=8.4 Hz, 2H), 7.35 (d, J=8.4 Hz, 2H), 7.44 (d, J=8.4 Hz, 2H), 7.62 (d, J=8.4 Hz, 2H). IR (KBr) cm$^{-1}$: 3333, 1584, 1512, 1434 and 1074.

EXAMPLE 24

{2-Amino-4-[(4-(2,4-difluorophenyl)piperazin-1-yl)methyl]thiophen-3-yl}(4-chlorophenyl)methanone

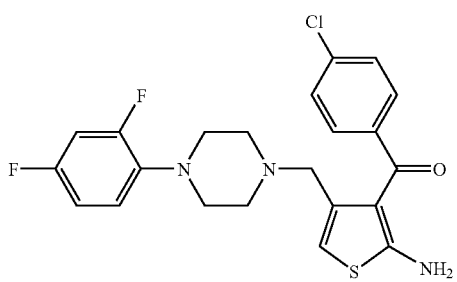

The title compound is purified by column chromatography (EtOAc:DCM/1:9 as eluent). Yellow solid, m.p. 170-172° C. $^1$H NMR (CDCl$_3$) δ: 2.04 (t, J=4.8 Hz, 4H), 2.77 (t, J=4.8 Hz, 4H), 3.00 (s, 2H), 6.06 (br s, 2H), 6.13 (s, 1H), 6.80 (m, 3H), 7.35 (d, J=8.6 Hz, 2H), 7.56 (d, J=8.6 Hz, 2H). IR (KBr) cm$^{-1}$: 2955, 1592, 1424, 1278, 1092 and 1034.

EXAMPLE 25

{2-Amino-4-[(4-(2,6-difluorophenyl)piperazin-1-yl)methyl]thiophen-3-yl}(4-chlorophenyl)methanone

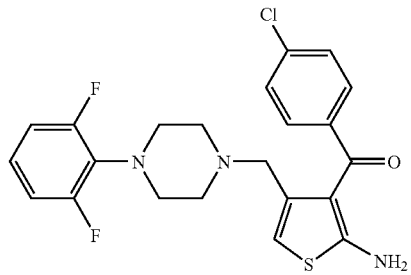

The title compound is purified by column chromatography (EtOAc:DCM/1:9 as eluent). Yellow oil. $^1$H NMR (CDCl$_3$) δ: 1.99 (t, J=4.8 Hz, 4H), 2.95 (t, J=4.8 Hz, 4H), 2.98 (s, 2H), 6.08 (br s, 2H), 6.13 (s, 1H), 6.82 (m, 3H), 7.36 (d, J=6.6 Hz, 2H), 7.58 (d, J=6.6 Hz, 2H). IR (neat) cm$^{-1}$: 2988, 1564, 1433, 1256, 1082 and 1047.

EXAMPLE 26

{2-Amino-4-[(4-(3-chloro-4-fluorophenyl)piperazin-1-yl)methyl]thiophen-3-yl}(4-chlorophenyl)methanone

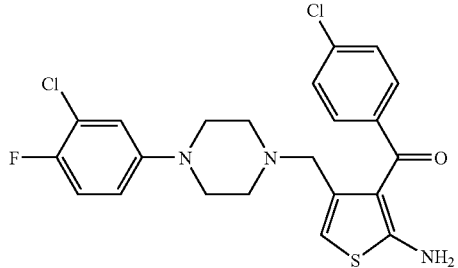

The title compound is purified by column chromatography (EtOAc:DCM/1:9 as eluent). Yellow solid, m.p. 161-163° C. $^1$H NMR (CDCl$_3$) δ: 2.01 (t, J=4.6 Hz, 4H), 2.85 (t, J=4.6 Hz, 4H), 3.00 (s, 2H), 6.07 (br s, 2H), 6.13 (s, 1H), 6.68 (m, 1H), 6.81 (dd, J=6.4 and 3.0 Hz, 1H), 6.93 (t, J=8.8 Hz, 1H), 7.38 (d, J=8.6 Hz, 2H), 7.56 (d, J=8.6 Hz, 2H). IR (KBr) cm$^{-1}$: 2972, 1577, 1432, 1271, 1094 and 1032.

EXAMPLE 27

{2-Amino-4-[(4-cyclohexylpiperazin-1-yl)methyl]thiophen-3-yl}(4-chlorophenyl)methanone

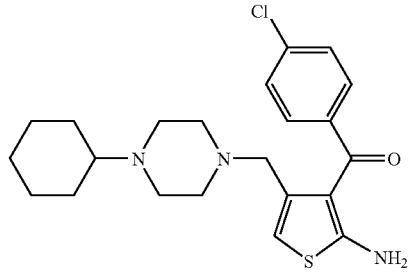

The title compound is purified by column chromatography (EtOAc:MeOH/1:1 as eluent). Yellow solid, m.p. 120-122° C. $^1$H NMR (CDCl$_3$) δ: 1.17 (m, 6H), 1.64 (m, 5H), 1.78 (t, J=5.2 Hz, 4H), 2.39 (t, J=5.2 Hz, 4H), 3.13 (s, 2H), 5.69 (br s, 2H), 6.91 (s, 1H), 7.39 (d, J=7.2 Hz, 2H), 7.48 (d, J=7.2 Hz, 2H).

EXAMPLE 28

{2-Amino-4-[(4-(4-chlorophenyl)piperidin-1-yl)methyl]thiophen-3-yl}(4-chlorophenyl)methanone

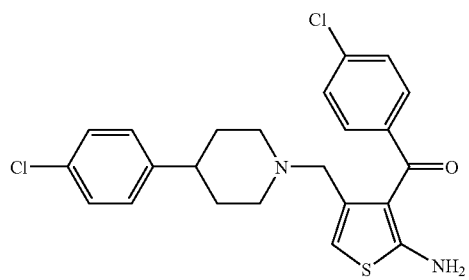

The title compound is purified by column chromatography (EtOAc:DCM/1:9 as eluent). Yellow oil. $^1$H NMR (CDCl$_3$) δ: 1.67 (m, 4H), 2.27 (m, 1H), 2.54 (t, J=5.4 Hz, 4H), 3.04 (s, 2H), 6.09 (s, 2H), 6.16 (s, 1H), 7.33 (s, 4H), 7.39 (d, J=8.6 Hz, 2H), 7.51 (t, J=8.6 Hz, 2H). IR (KBr) cm$^{-1}$: 3378, 1556, 1443, 1412, 1074 and 822.

EXAMPLE 29

{2-Amino-4-[(4-(4-nitrophenyl)piperazin-1-yl)methyl]thiophen-3-yl}(4-chlorophenyl)methanone

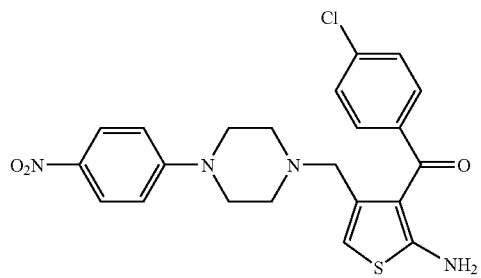

The title compound is purified by column chromatography (EtOAc:DCM/1:9 as eluent). Yellow solid, m.p. 110-112° C. $^1$H NMR (CDCl$_3$) δ: 2.46 (t, J=5.4 Hz, 4H), 2.84 (t, J=5.4 Hz, 4H), 3.03 (s, 2H), 6.21 (br s, 2H), 6.24 (s, 1H), 6.81 (d, J=9.6 Hz, 2H), 7.46 (d, J=9.2 Hz, 2H), 7.65 (d, J=9.6 Hz, 2H), 8.13 (d, J=9.2 Hz, 2H). IR (KBr) cm$^{-1}$: 3455, 1733, 1551, 1533.

EXAMPLE 30

{2-Amino-4-[(4-isopropylpiperazin-1-yl]methyl)thiophen-3-yl}(4-chlorophenyl)methanone

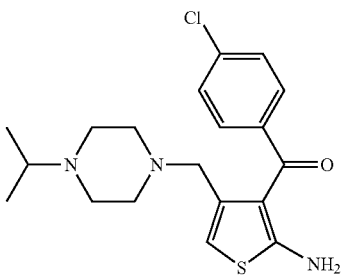

The title compound is purified by column chromatography (EtOAc:MeOH/3:7 as eluent). Yellow oil. $^1$H NMR (CDCl$_3$) δ: 1.02 (m, 6H), 1.99 (t, J=5.2 Hz, 4H), 2.35 (t, J=5.2 Hz, 4H), 2.57 (m, 1H), 2.93 (s, 2H), 6.05 (br s, 2H), 6.10 (s, 1H), 7.36 (d, J=8.6 Hz, 2H), 7.52 (d, J=8.6 Hz, 2H).

EXAMPLE 31

{2-Amino-4-[(4-naphthalen-1-yl)piperazin-1-yl)methyl]thiophen-3-yl}(4-chlorophenyl)methanone

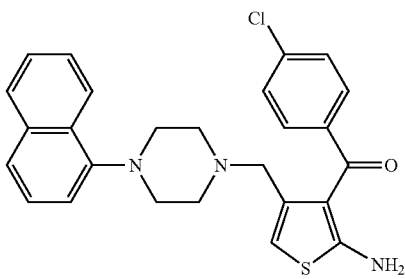

The title compound is purified by column chromatography (EtOAc:DCM/2:8 as eluent). Brown solid, m.p. 178° C. $^1$H NMR (CDCl$_3$) δ: 2.42 (t, J=5.4 Hz, 4H), 2.54 (t, J=5.4 Hz, 4H), 3.03 (s, 2H), 6.04 (s, 2H), 6.11 (s, 1H), 6.93 (d, J=7.2 Hz, 2H), 7.06 (d, J=7.2 Hz, 2H), 7.33 (m, 3H), 7.56 (d, J=7.8 Hz, 2H), 7.87 (d, J=7.8 Hz, 2H).

EXAMPLE 32

{2-Amino-4-[(4-(3,4-difluorophenyl)piperazin-1-yl)methyl]thiophen-3-yl}(4-chlorophenyl)methanone

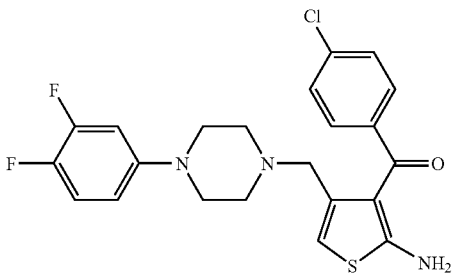

The title compound is purified by column chromatography (EtOAc:DCM/1:9 as eluent). Yellow solid, m.p. 143-145° C. $^1$H NMR (CDCl$_3$) δ: 2.01 (t, J=4.8 Hz, 4H), 2.84 (t, J=4.8 Hz, 4H), 3.00 (s, 2H), 6.07 (br s, 2H), 6.13 (s, 1H), 6.52 (m, 2H), 7.02 (m, 1H), 7.36 (d, J=8.2 Hz, 2H), 7.53 (d, J=8.2 Hz, 2H). IR (KBr) cm$^{-1}$: 2967, 1587, 1433, 1267, 1085 and 1033.

EXAMPLE 33

{2-Amino-4-[(4-cyclopentylpiperazin-1-yl)methyl] thiophen-3-yl}(4-chlorophenyl)methanone

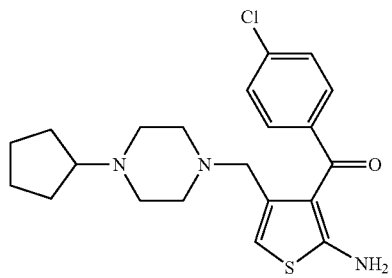

The title compound is purified by column chromatography (EtOAc:MeOH/6:4 as eluent). Yellow solid, m.p. 95-97° C. $^1$H NMR (CDCl$_3$) δ: 1.16 (m, 4H), 1.48 (m, 5H), 1.82 (t, J=5.2 Hz, 4H), 2.79 (s, 2H), 2.85 (t, J=5.2 Hz, 4H), 5.72 (br s, 2H), 6.90 (s, 1H), 7.32 (d, J=7.0 Hz, 2H), 8.00 (d, J=7.0 Hz, 2H).

EXAMPLE 34

{2-Amino-4-[(4-cycloheptylpiperazin-1-yl)methyl] thiophen-3-yl}(4-chlorophenyl)methanone

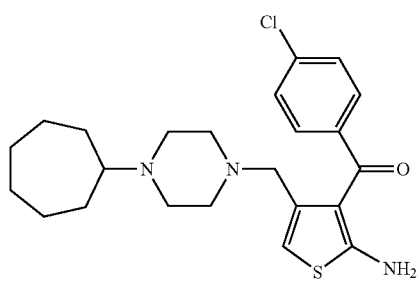

The title compound is purified by column chromatography (EtOAc:MeOH/7:3 as eluent). Yellow oil. $^1$H NMR (CDCl$_3$) δ: 1.26 (m, 12H), 1.79 (t, J=5.2 Hz, 4H), 2.09 (t, J=5.2 Hz, 4H), 2.81 (m, 1H), 3.03 (s, 2H), 6.03 (br s, 2H), 6.09 (s, 1H), 7.31 (d, J=8.8 Hz, 2H), 7.45 (d, J=8.8 Hz, 2H).

EXAMPLE 35

{2-Amino-4-[(4-(4-chlorobenzyl)piperazin-1-yl) methyl]thiophen-3-yl}(4-chlorophenyl)methanone

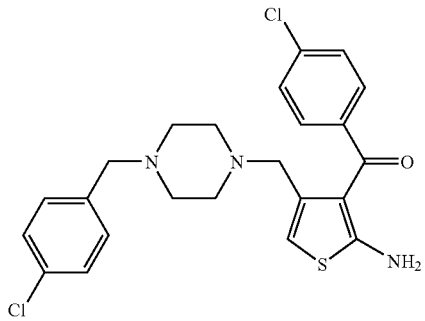

The title compound is purified by column chromatography (EtOAc:DCM/1:1 as eluent). Yellow solid, m.p. 65-67° C. $^1$H NMR (CDCl$_3$) δ: 1.88 (t, J=4.6 Hz, 4H), 2.21 (m, 4H), 2.92 (s, 2H), 3.36 (s, 2H), 6.02 (br s, 2H), 6.09 (s, 1H), 7.24 (m, 4H), 7.34 (d, J=8.6 Hz, 2H), 7.52 (d, J=8.6 Hz, 2H). IR (KBr) cm$^{-1}$: 3372, 1589, 1478, 1433, 1241.

EXAMPLE 36

{2-Amino-4-[(4-benzylpiperazin-1-yl)methyl] thiophen-3-yl}(4-chlorophenyl)methanone

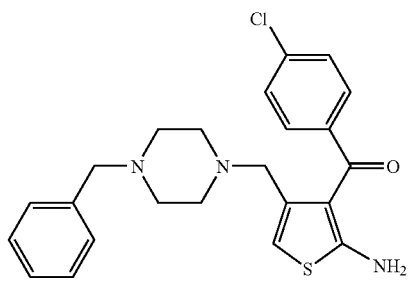

The title compound is purified by column chromatography (DCM:MeOH/9.5:0.5 as eluent). Yellow solid, m.p. 153-155° C. $^1$H NMR (CDCl$_3$) δ: 1.88 (t, J=4.6 Hz, 4H), 2.24 (t, J=4.6 Hz, 4H), 3.41 (s, 2H), 3.48 (s, 2H), 6.01 (br s, 2H), 6.06 (s, 1H), 7.24 (m, 5H), 7.42 (d, J=8.6 Hz, 2H), 7.64 (d, J=8.6 Hz, 2H). IR (KBr) cm$^{-1}$: 3377, 1592, 1468, 1423, 1251.

EXAMPLE 37

(2-Amino-4-{[4-(2-(4-chlorophenyl)ethyl)piperazin-1-yl]methyl}thiophen-3-yl)(4-chlorophenyl)methanone

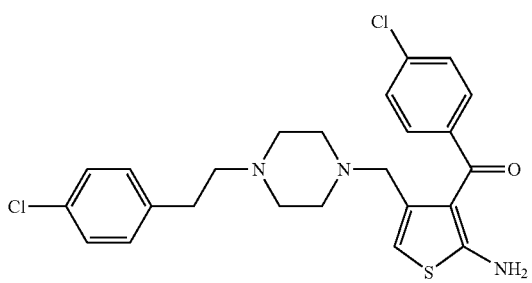

The title compound is purified by column chromatography (DCM:MeOH/9.5:0.5 as eluent). Yellow oil. $^1$H NMR (CDCl$_3$) δ: 1.92 (t, J=4.6 Hz, 4H), 2.27 (m, 4H), 2.47 (t, J=7.2 Hz, 2H), 2.67 (t, J=7.2 Hz, 2H), 2.95 (s, 2H), 6.09 (br s, 3H), 7.08 (d, J=8.6 Hz, 2H), 7.23 (d, J=8.6 Hz, 2H), 7.36 (d, J=8.6 Hz, 2H), 7.52 (d, J=8.6 Hz, 2H). IR (KBr) cm$^{-1}$: 3376, 1588, 1456, 1434, 1242.

EXAMPLE 38

{2-Amino-4-[(4-(4-fluorobenzyl)piperazin-1-yl)methyl]thiophen-3-yl}(4-chlorophenyl)methanone

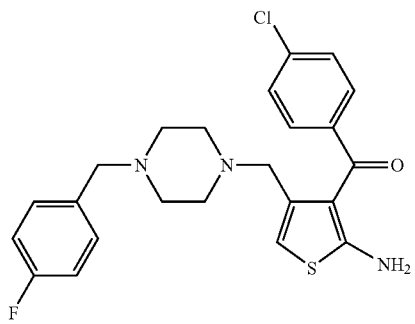

The title compound is purified by column chromatography (MeOH:DCM/0.5:9.5 as eluent). Yellow solid, m.p. 230-231° C. $^1$H NMR (CDCl$_3$) δ: 1.55 (t, J=4.6 Hz, 4H), 1.88 (t, J=4.6 Hz, 4H), 2.92 (s, 2H), 2.92 (s, 2H), 6.02 (br s, 2H), 6.09 (s, 1H), 6.96 (t, J=8.8 Hz, 2H), 7.21 (dd, J=8.8 and 5.6 Hz, 2H), 7.35 (d, J=8.4 Hz, 2H), 7.52 (d, J=8.4 Hz, 2H). IR (KBr) cm$^{-1}$: 3358, 1577, 1468, 1423, 1267.

EXAMPLE 39

{2-Amino-4-[(4-cyclooctylpiperazin-1-yl)methyl]thiophen-3-yl}(4-chlorophenyl)methanone

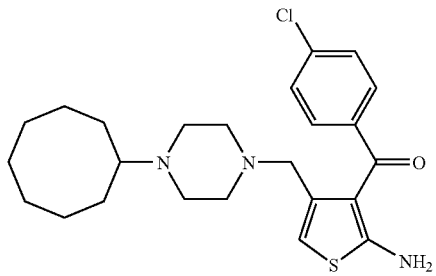

The title compound is purified by column chromatography (DCM:MeOH/0.5:9.5 as eluent). Yellow oil. $^1$H NMR (CDCl$_3$) δ: 1.21 (m, 10H), 1.44 (m, 4H), 1.76 (m, 5H), 2.42 (t, J=5.2 Hz, 4H), 3.14 (s, 2H), 5.74 (br s, 2H), 6.88 (s, 1H), 7.41 (d, J=8.8 Hz, 2H), 7.56 (d, J=8.8 Hz, 2H).

EXAMPLE 40

(2-Amino-4-{[4-[3-(4-chlorophenyl)propyl]piperazin-1-yl]methyl}thiophen-3-yl)(4-chlorophenyl)methanone

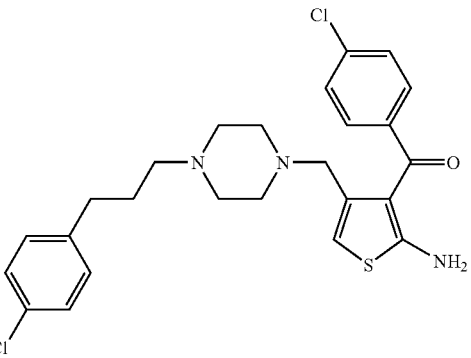

The title compound is purified by column chromatography (DCM:MeOH/9.5:0.5 as eluent). Yellow solid, m.p. 60-61° C. $^1$H NMR (CDCl$_3$) δ: 1.62 (m, 2H), 1.90 (t, J=4.8 Hz, 4H), 2.24 (m, 4H), 2.58 (t, J=4.8 Hz, 4H), 2.95 (s, 2H), 6.02 (br s, 2H), 6.09 (s, 1H), 7.10 (d, J=8.6 Hz, 2H), 7.20 (d, J=8.6 Hz, 2H), 7.34 (d, J=8.6 Hz, 2H), 7.52 (d, J=8.6 Hz, 2H). IR (KBr) cm$^{-1}$: 3382, 1578, 1455, 1432, 1222.

EXAMPLE 41

{2-Amino-4-[(4-(2,4-dichlorophenyl)piperazin-1-yl)methyl]thiophen-3-yl}(4-chlorophenyl)methanone

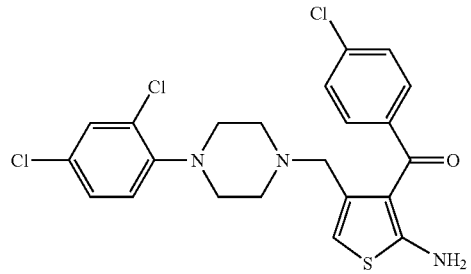

The title compound is purified by column chromatography (EtOAc:DCM 1:9 as eluent). Yellow solid, m.p. 142-143° C. $^1$H NMR (CDCl$_3$) δ: 2.04 (t, J=4.6 Hz, 4H), 2.76 (t, J=4.6 Hz, 4H), 3.01 (s, 2H), 6.05 (br s, 2H), 6.14 (s, 1H), 6.88 (d, J=8.6 Hz, 1H), 7.14 (dd, J=11 and 2.6 Hz, 1H), 7.31 (d, J=2.6 Hz, 1H), 7.38 (d, J=8.8 Hz, 2H), 7.56 (d, J=8.8 Hz, 2H). IR (KBr) cm$^{-1}$: 2972, 1578, 1455, 1265.

EXAMPLE 42

{2-Amino-4-[(4-(2,5-difluorophenyl)piperazin-1-yl)methyl]thiophen-3-yl}(4-chlorophenyl)methanone

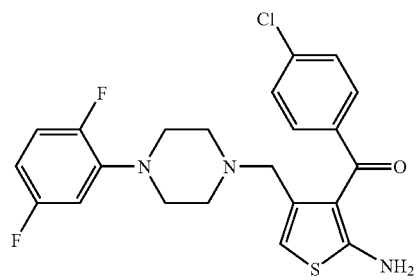

The title compound is purified by column chromatography (EtOAc:DCM/1:9 as eluent). Yellow solid, m.p. 62-63° C. $^1$H NMR (CDCl$_3$) δ: 1.99 (t, J=4.8 Hz, 4H), 2.95 (t, J=4.8 Hz, 4H), 2.98 (s, 2H), 6.08 (br s, 2H), 6.13 (s, 1H), 6.82 (m, 3H), 7.36 (d, J=8.6 Hz, 2H), 7.58 (d, J=8.6 Hz, 2H). IR (neat) cm$^{-1}$: 2976, 1555, 1442, 1265, 1077.

EXAMPLE 43

{2-Amino-4-[(4-(2-(trifluoromethyl)phenyl)piperazin-1-yl)methyl]thiophen-3-yl}(4-chlorophenyl)methanone

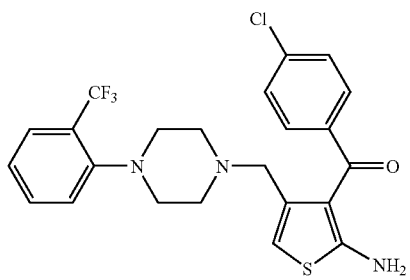

The title compound is purified by column chromatography (EtOAc:DCM/1:9 as eluent). Yellow oil. $^1$H NMR (CDCl$_3$) δ: 2.01 (t, J=4.8 Hz, 4H), 2.67 (t, J=5.2 Hz, 4H), 3.00 (s, 2H), 6.05 (br s, 2H), 6.13 (s, 1H), 7.12 (t, J=8.4 Hz, 1H), 7.18 (m, 2H), 7.36 (d, J=8.8 Hz, 2H), 7.44 (m, 1H), 7.57 (d, J=8.8 Hz, 2H). IR (KBr) cm$^{-1}$: 3353, 1563, 1533, 1438 and 1077.

EXAMPLE 44

{2-Amino-4-[(4-(4-chloro-3-(trifluoromethyl)phenyl)piperazin-1-yl)methyl]thiophen-3-yl}(4-chlorophenyl)methanone

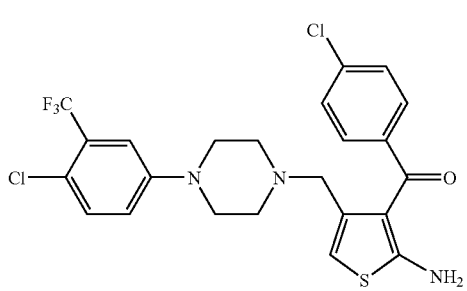

The title compound is purified by column chromatography (EtOAc:DCM/1:9 as eluent). Yellow solid, m.p. 141-143° C. $^1$H NMR (CDCl$_3$) δ: 1.96 (t, J=4.4 Hz, 4H), 2.87 (t, J=4.4 Hz, 4H), 2.94 (s, 2H), 6.01 (br s, 2H), 6.07 (s, 1H), 6.78 (dd, J=8.2 and 2.8 Hz, 1H), 7.00 (s, 1H), 7.19 (d, J=8.2 Hz, 1H), 7.33 (d, J=8.2 Hz, 2H), 7.48 (d, J=8.2 Hz, 2H). IR (KBr) cm$^{-1}$: 2977, 1578, 1443, 1277, 1078.

EXAMPLE 45

{2-Amino-4-[(4-(2,4,6-trifluorophenyl)piperazin-1-yl)methyl]thiophen-3-yl}(4-chlorophenyl)methanone

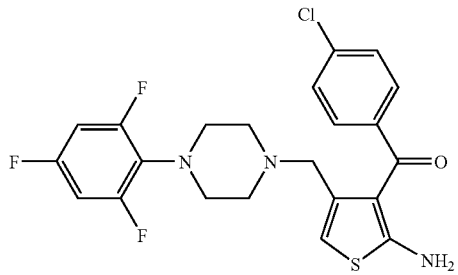

The title compound is purified by column chromatography (EtOAc:DCM/1:9 as eluent). Yellow solid, m.p. 153-155° C. $^1$H NMR (CDCl$_3$) δ: 1.98 (t, J=4.6 Hz, 4H), 2.87 (t, J=4.8 Hz, 4H), 2.98 (s, 2H), 6.08 (br s, 2H), 6.13 (s, 1H), 6.58 (t, J=9.0 Hz, 2H), 7.37 (d, J=8.6 Hz, 2H), 7.56 (d, J=8.6 Hz, 2H). IR (KBr) cm$^{-1}$: 2977, 1583, 1443, 1277, 1083.

EXAMPLE 46

{2-Amino-4-[(4-(2-chloro-4-fluorophenyl)piperazin-1-yl)methyl]thiophen-3-yl}(4-chlorophenyl)methanone

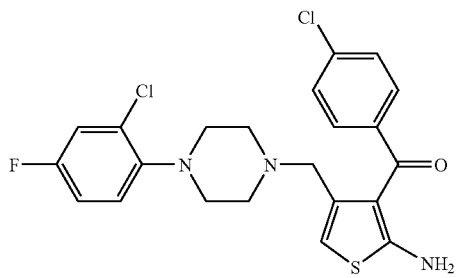

The title compound is purified by column chromatography (EtOAc:DCM/1:9 as eluent). Yellow solid, m.p. 59-61° C. $^1$H NMR (CDCl$_3$) δ: 2.06 (t, J=4.6 Hz, 4H), 2.75 (t, J=4.6 Hz, 4H), 3.02 (s, 2H), 6.07 (br s, 2H), 6.15 (s, 1H), 6.92 (d, J=8.4 Hz, 1H), 7.08 (d, J=8.4 Hz, 1H), 6.93 (t, J=8.8 Hz, 1H), 7.38 (d, J=8.6 Hz, 2H), 7.58 (d, J=8.6 Hz, 2H). IR (KBr) cm$^{-1}$: 2984, 1583, 1443, 1283, 1123.

EXAMPLE 47

{2-Amino-4-[(4-(2-fluoro-4-chlorophenyl)piperazin-1-yl)methyl]thiophen-3-yl}(4-chlorophenyl)methanone

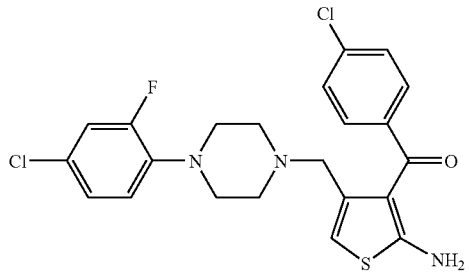

The title compound is purified by column chromatography (EtOAc:DCM/1:9 as eluent). Yellow solid, m.p. 161-163° C. $^1$H NMR (CDCl$_3$) δ: 2.04 (t, J=4.8 Hz, 4H), 2.80 (t, J=4.8 Hz, 4H), 3.01 (s, 2H), 6.07 (br s, 2H), 6.14 (s, 1H), 6.78 (t, J=7.6 Hz, 1H), 7.01 (m, 2H), 7.37 (d, J=8.6 Hz, 2H), 7.55 (d, J=8.6 Hz, 2H). IR (KBr) cm$^{-1}$: 2967, 1577, 1452, 1271, 1110.

EXAMPLE 48

{2-Amino-4-[(4-(3,5-difluorophenyl)piperazin-1-yl) methyl]thiophen-3-yl}(4-chlorophenyl)methanone

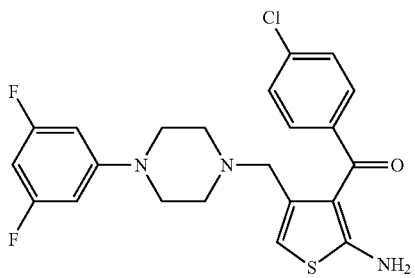

The title compound is purified by column chromatography (EtOAc:DCM/1:9 as eluent). Yellow solid, m.p. 162-163° C. $^1$H NMR (CDCl$_3$) δ: 2.00 (t, J=4.8 Hz, 4H), 2.93 (t, J=4.8 Hz, 4H), 3.00 (s, 2H), 6.10 (br s, 2H), 6.13 (s, 1H), 6.26 (m, 3H), 7.38 (d, J=8.8 Hz, 2H), 7.55 (d, J=8.8 Hz, 2H). IR (neat) cm$^{-1}$: 2982, 1551, 1434, 1255, 1082.

EXAMPLE 49

{2-Amino-4-[(4-(2,6-dichlorophenyl)piperazin-1-yl) methyl]thiophen-3-yl}(4-chlorophenyl)methanone

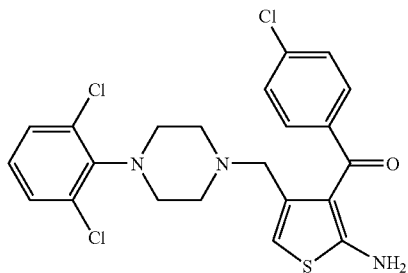

The title compound is purified by column chromatography (EtOAc:DCM/1:9 as eluent). Yellow solid, m.p. 128-130° C. $^1$H NMR (CDCl$_3$) δ: 2.02 (t, J=4.8 Hz, 4H), 2.82 (t, J=4.6 Hz, 4H), 3.02 (s, 2H), 6.05 (br s, 2H), 6.09 (s, 1H), 7.01 (d, J=8.6 Hz, 1H), 7.17 (t, J=8.6 Hz, 1H), 7.29 (d, J=2.6 Hz, 1H), 7.34 (d, J=8.8 Hz, 2H), 7.52 (d, J=8.8 Hz, 2H). IR (KBr) cm$^{-1}$: 2977, 15678, 1466, 1272.

EXAMPLE 50

{2-Amino-4-[(4-(4-(trifluoromethoxy)phenyl)piperazin-1-yl)methyl]thiophen-3-yl}(4-chlorophenyl) methanone

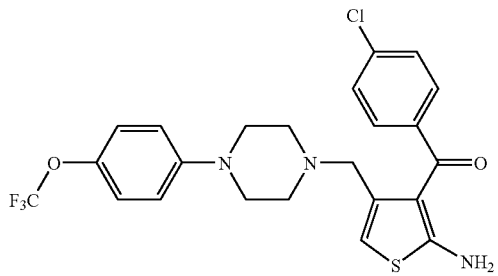

The title compound is purified by column chromatography (EtOAc:DCM/1:9 as eluent). Yellow solid, m.p. 151-153° C. $^1$H NMR (CDCl$_3$) δ: 2.04 (t, J=4.8 Hz, 4H), 2.92 (t, J=4.8 Hz, 4H), 3.01 (s, 2H), 6.09 (br s, 2H), 6.14 (s, 1H), 6.80 (d, J=8.6 Hz, 2H), 7.07 (d, J=8.6 Hz, 2H), 7.38 (d, J=7.8 Hz, 2H), 7.56 (d, J=7.8 Hz, 2H). IR (KBr) cm$^{-1}$: 2973, 1614, 1264, 1087, 1032.

EXAMPLE 51

{2-Amino-4-[(4-(pyridin-3-yl)piperazin-1-yl)methyl]thiophen-3-yl}(4-chlorophenyl)methanone

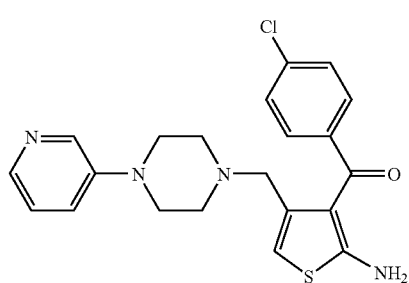

The title compound is purified by column chromatography (EtOAc:MeOH/6:4 as eluent). Yellow solid, m.p. 101-103° C. $^1$H NMR (CDCl$_3$) δ: 2.01 (t, J=4.8 Hz, 4H), 2.84 (t, J=4.8 Hz, 4H), 3.00 (s, 2H), 6.09 (br s, 2H), 6.13 (s, 1H), 6.52 (d, J=7.8 Hz, 1H), 6.78 (m, 1H), 7.42 (d, J=8.6 Hz, 2H), 7.57 (d, J=8.6 Hz, 2H), 8.07 (s, 1H), 8.24 (d, J=9.0 Hz, 1H). IR (KBr) cm$^{-1}$: 2958, 1586, 1444, 1270, 1096.

EXAMPLE 52

{2-Amino-4-[(4-(2,5-dichlorophenyl)piperazin-1-yl) methyl]thiophen-3-yl}(4-chlorophenyl)methanone

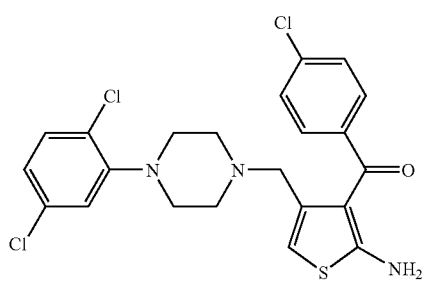

The title compound is purified by column chromatography (EtOAc:DCM/0.5:9.5 as eluent). Yellow solid, m.p. 78-80° C. $^1$H NMR (CDCl$_3$) δ: 2.07 (t, J=4.6 Hz, 4H), 2.81 (t, J=4.6 Hz, 4H), 3.03 (s, 2H), 6.08 (br s, 2H), 6.15 (s, 1H), 6.93 (s, 1H), 7.24 (d, J=9.2 Hz, 2H), 7.39 (d, J=8.6 Hz, 2H), 7.57 (d, J=8.6 Hz, 2H). IR (KBr) cm$^{-1}$: 2988, 1568, 1462, 1271.

EXAMPLE 53

{2-Amino-4-[(4-(2,3-difluorophenyl)piperazin-1-yl)methyl]thiophen-3-yl}(4-chlorophenyl)methanone

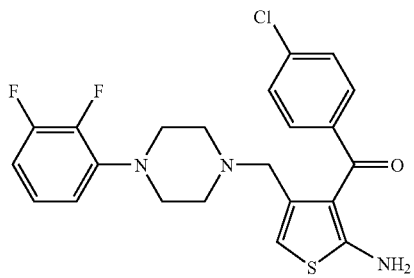

The title compound is purified by column chromatography (EtOAc:DCM/0.5:9.5 as eluent). Yellow solid, m.p. 138° C. $^1$H NMR (CDCl$_3$) δ: 1.99 (t, J=4.8 Hz, 4H), 2.78 (t, J=4.8 Hz, 4H), 2.95 (s, 2H), 6.00 (br s, 2H), 6.07 (s, 1H), 6.54 (t, J=7.6 Hz, 1H), 6.67 (d, J=7.8 Hz, 1H), 6.85 (t, J=8.2 Hz, 1H), 7.31 (d, J=8.4 Hz, 2H), 7.48 (d, J=−8.4 Hz, 2H). IR (KBr) cm$^{-1}$: 2981, 1565, 1453, 1254, 1072.

EXAMPLE 54

{2-Amino-4-[(4-(4-chlorophenyl)-3-methylpiperazin-1-yl)methyl]thiophen-3-yl}(4-chlorophenyl)methanone

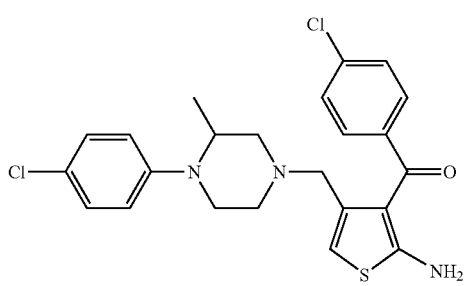

The title compound is purified by column chromatography (EtOAc:DCM/1:9 as eluent). Yellow solid, m.p. 105° C. $^1$H NMR (CDCl$_3$) δ: 1.12 (d, J=6.6 Hz, 3H), 2.12 (t, J=5.4 Hz, 2H), 2.21 (t, J=5.4 Hz, 2H), 2.67 (m, 2H), 3.11 (s, 2H), 3.21 (m, 1H), 6.08 (br s, 2H), 6.13 (s, 1H), 6.72 (d, J=8.8 Hz, 2H), 6.82 (d, J=9.0 Hz, 2H), 7.14 (d, J=8.8 Hz, 2H), 7.42 (d, J=9.0 Hz, 2H), IR (KBr) cm$^{-1}$: 3372, 1588, 1523, 1233.

EXAMPLE 55

{2-Amino-4-[(4-(4-(trifluoromethyl)phenyl)piperazin-1-yl)methyl]thiophen-3-yl}[3-(trifluoromethyl)phenyl]methanone

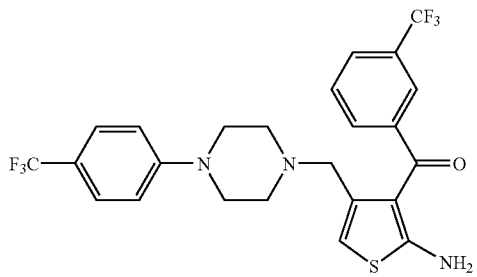

The title compound is purified by column chromatography (EtOAc:DCM/0.25:9.75 as eluent). Yellow solid, m.p. 143-145° C. $^1$H NMR (CDCl$_3$) δ: 1.95 (t, J=4.8 Hz, 4H), 2.94 (s, 2H), 2.98 (t, J=4.8 Hz, 4H), 6.14 (s, 1H), 6.28 (br s, 2H), 6.82 (t, J=8.8 Hz, 2H), 7.42 (d, J=8.8 Hz, 2H), 7.54 (t, J=8.0 Hz, 1H), 7.74 (m, 2H), 7.85 (s, 1H).

EXAMPLE 56

{2-Amino-4-[(4-(3-fluorophenyl)piperazin-1-yl)methyl]thiophen-3-yl}[3-(trifluoromethyl)phenyl]methanone

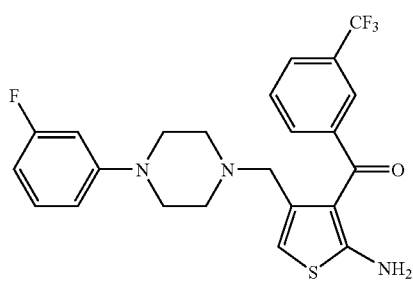

The title compound is purified by column chromatography (EtOAc:DCM/1:9 as eluent). Yellow solid, m.p. 100-102° C. $^1$H NMR (CDCl$_3$) δ: 1.94 (t, J=4.8 Hz, 4H), 2.90 (t, J=4.8 Hz, 4H), 2.93 (s, 2H), 6.14 (s, 1H), 6.29 (br s, 2H), 6.49 (m, 2H), 6.57 (d, J=9.6 Hz, 1H), 7.15 (q, J=7.2 Hz, 1H), 7.54 (t, J=8.0 Hz, 1H), 7.74 (m, 2H), 7.84 (s, 1H).

EXAMPLE 57

{2-Amino-4-[(4-(2,6-difluorophenyl)piperazin-1-yl)methyl]thiophen-3-yl}[3-(trifluoromethyl)phenyl]methanone

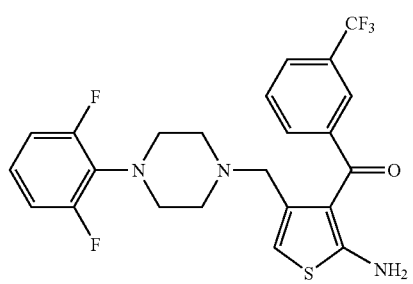

The title compound is purified by column chromatography (EtOAc:DCM/0.5:9.5 as eluent). Yellow solid, m.p. 163-165° C. $^1$H NMR (CDCl$_3$) δ: 1.92 (t, J=4.8 Hz, 4H), 2.89 (t, J=4.8 Hz, 4H), 3.02 (s, 2H), 6.73 (s, 1H), 6.84 (m, 5H), 7.34 (t, J=8.0 Hz, 1H), 7.46 (d, J=8.0 Hz, 1H), 7.84 (d, J=7.8 Hz, 1H), 8.01 (s, 1H).

EXAMPLE 58

{2-Amino-4-(spiro[benzo[d][1,3]-dioxole-2,4'piperidine]-1'-ylmethyl)thiophen-3-yl}(4-chlorophenyl) methanone

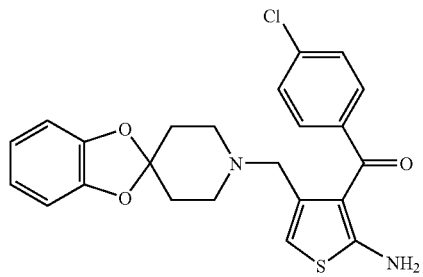

The title compound is purified by column chromatography (DCM:EtOAc/1:9 as eluent). Yellow solid, m.p. 209-211° C. $^1$H NMR (CDCl$_3$) δ: 2.06 (t, J=6.0 Hz, 4H), 3.02 (t, J=6.0 Hz, 4H), 3.52 (s, 2H), 6.02 (br s, 2H), 6.76 (m, 5H), 7.42 (d, J=8.6 Hz, 2H), 7.57 (d, J=8.6 Hz, 2H).

EXAMPLE 59

{2-Amino-4-(5-tert-butylspiro[benzo[d][1,3]-dioxole-2,4'-piperidine]-1'-ylmethyl)thiophen-3-yl}(4-chlorophenyl)methanone

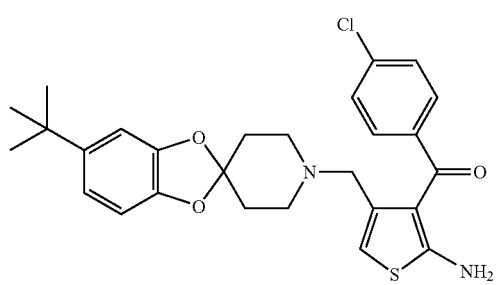

The title compound is purified by column chromatography (DCM:EtOAc/1:9 as eluent). Yellow solid, m.p. 100-102° C. $^1$H NMR (CDCl$_3$) δ: 1.27 (s, 9H), 1.96 (t, J=5.6 Hz, 2H), 2.06 (t, J=5.6 Hz, 2H), 3.01 (t, J=6.0 Hz, 4H), 3.67 (s, 2H), 6.15 (br s, 2H), 6.62 (d, J=8.2 Hz, 1H), 6.78 (m, 2H), 6.84 (s, 1H), 7.39 (d, J=8.4 Hz, 2H), 7.56 (d, J=8.4 Hz, 2H).

EXAMPLE 60

{2-Amino-4-(4-fluorospiro[benzo[d][1,3]-dioxole-2,4'-piperidine]-1'-ylmethyl)thiophen-3-yl}(4-chlorophenyl)methanone

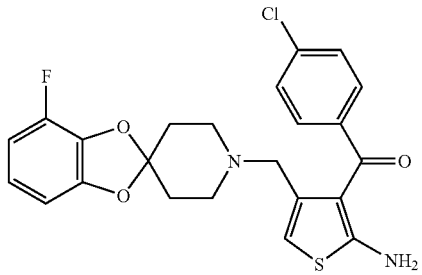

The title compound is purified by column chromatography (DCM:EtOAc/9.9:0.1 as eluent). Yellow solid, m.p. 80-81° C. $^1$H NMR (CDCl$_3$) δ: 1.81 (t, J=6.0 Hz, 4H), 2.08 (t, J=6.0 Hz, 4H), 3.03 (s, 2H), 6.10 (s, 1H), 6.13 (br s, 2H), 6.52 (d, J=7.6 Hz, 1H), 6.58 (t, J=7.6 Hz, 1H), 6.72 (m, 1H), 7.40 (d, J=8.4 Hz, 2H), 7.57 (d, J=8.4 Hz, 2H).

EXAMPLE 61

{2-Amino-4-(4-methylspiro[benzo[d][1,3]-dioxole-2,4'piperidine]-1'-ylmethyl)thiophen-3-yl}(4-chlorophenyl)methanone

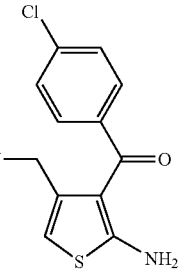

The title compound is purified by column chromatography (DCM:EtOAc/7:3 as eluent). Yellow solid, m.p. 184-186° C. $^1$H NMR (CDCl$_3$) δ: 1.93 (t, J=5.6 Hz, 4H), 2.20 (s, 3H), 3.14 (m, 4H), 3.46 (s, 2H), 5.84 (m, 2H), 6.64 (m, 3H), 6.88 (s, 1H), 7.42 (d, J=8.8 Hz, 2H), 7.53 (d, J=8.8 Hz, 2H).

EXAMPLE 62

{2-Amino-4-(5-methylspiro[benzo[d][1,3]-dioxole-2,4'-piperidine]-1-ylmethyl)thiophen-3-yl}(4-chlorophenyl)methanone

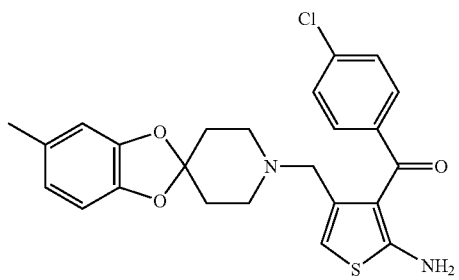

The title compound is purified by column chromatography (petroleum ether:EtOAc/2:8 as eluent). White solid, m.p. 119-121° C. $^1$H NMR (CDCl$_3$) δ: 1.77 (t, J=5.2 Hz, 4H), 2.06 (t, J=5.2 Hz, 4H), 2.23 (s, 3H), 3.02 (s, 2H), 6.08 (br s, 2H), 6.12 (s, 1H), 6.54 (m, 3H), 7.38 (d, J=8.4 Hz, 2H), 7.54 (d, J=8.4 Hz, 2H).

EXAMPLE 63

{2-Amino-4-[(4-(4-chlorophenylamino)piperidin-1-yl)methyl]thiophen-3-yl}(4-chlorophenyl)methanone

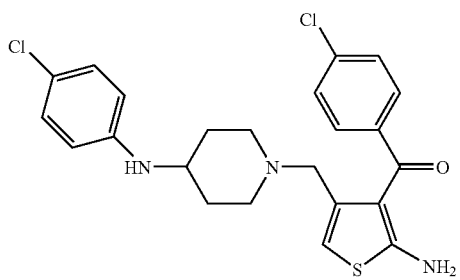

The title compound is purified by column chromatography (cyclohexane:EtOAc/8:2 as eluent). Mass (m/z): 460.48 (M+1). $^1$H NMR (CDCl$_3$) δ: 1.18 (m, 1H), 1.81 (m, 5H), 2.24 (m, 3H), 3.06 (s, 2H), 3.09 (m, 1H), 6.04 (br s, 2H), 6.18 (s, 1H), 6.36 (d, 2H, J=8.8 Hz), 7.07 (d, 2H, J=8.8 Hz), 7.38 (d, 2H, J=8.4 Hz), 7.54 (d, 2H, J=8.4 Hz).

EXAMPLE 64

{2-Amino-4-[(4-(4-chlorophenylmethylamino)piperidin-1-yl)methyl]thiophen-3-yl}(4-chlorophenyl)methanone

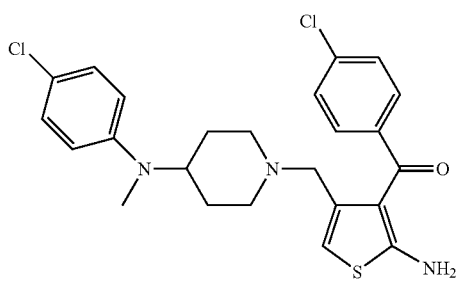

The title compound is purified by column chromatography (cyclohexane:EtOAc/8:2 as eluent). Mass (m/z): 476.47 (M+1). $^1$H NMR (CDCl$_3$) δ: 1.40 (m, 3H), 1.67 (m, 3H), 2.20 (m, 2H), 2.70 (s, 3H), 2.92 (s, 2H), 3.30 (m, 1H), 6.02 (br s, 2H), 6.11 (s, 1H), 6.62 (d, 2H, J=9.2 Hz), 7.12 (d, 2H, J=9.2 Hz), 7.39 (d, 2H, J=8.4 Hz), 7.56 (d, 2H, J=8.4 Hz).

EXAMPLE 65

{2-Amino-4-[(4-(4-chlorophenyl)-[1,4]diazepan-1-yl)methyl]thiophen-3-yl}(4-chlorophenyl)methanone

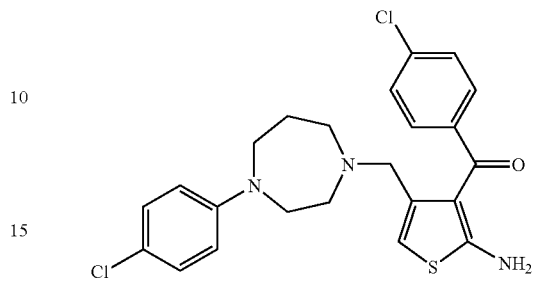

The title compound is purified by column chromatography (cyclohexane:EtOAc/8:2 as eluent). Mass (m/z): 460.56 (M+1). $^1$H NMR (CDCl$_3$) δ: 1.60 (m, 2H), 2.02 (m, 2H), 2.18 (m, 2H), 3.06 (s, 2H), 3.21 (m, 2H), 3.29 (m, 2H), 5.97 (br s, 2H), 6.11 (s, 1H), 6.49 (d, 2H, J=8.8 Hz), 7.10 (d, 2H, J=8.8 Hz), 7.36 (d, 2H, J=8.4 Hz), 7.51 (d, 2H, J=8.4 Hz).

EXAMPLE 66

{2-Amino-4-[(7-(4-chlorophenyl)-2,7-diaza-spiro[4.4]non-2-yl)methyl]thiophen-3-yl}(4-chlorophenyl)methanone

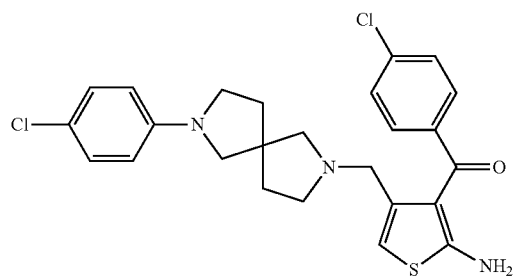

The title compound is purified by column chromatography (cyclohexane:EtOAc/8:2 as eluent). Mass (m/z): 486.48 (M+1). $^1$H NMR (CDCl$_3$) δ: 1.61 (m, 2H), 1.84 (m, 2H), 2.01-2.14 (m, 4H), 3.00-3.09 (m, 4H), 3.18 (m, 2H), 6.09 (br s, 2H), 6.11 (s, 1H), 6.39 (d, 2H, J=8.8 Hz), 7.15 (d, 2H, J=8.8 Hz), 7.34 (d, 2H, J=8.4 Hz), 7.52 (d, 2H, J=8.4 Hz).

EXAMPLE 67

{2-Amino-4-[(5-(4-chlorophenyl)hexahydropyrrolo[3,4-c]pyrrol-2-yl)methyl]thiophen-3-yl}(4-chlorophenyl)methanone

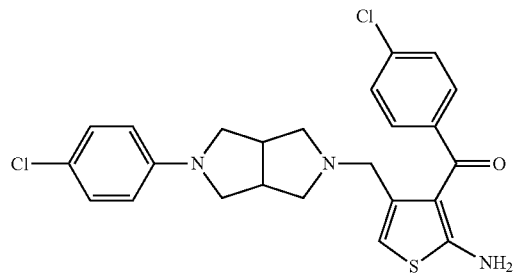

The title compound is purified by column chromatography (cyclohexane:EtOAc/8:2 as eluent). Mass (m/z): 472.42 (M+1). ¹H NMR (CDCl₃) δ: 2.03 (m, 2H), 2.10 (m, 2H), 2.73 (m, 2H), 2.85 (m, 2H), 3.06 (s, 2H), 3.34 (m, 2H), 6.06 (br s, 2H), 6.10 (s, 1H), 6.54 (d, 2H, J=8.8 Hz), 7.20 (d, 2H, J=8.8 Hz), 7.24 (d, 2H, J=8.4 Hz), 7.33 (d, 2H, J=8.4 Hz).

EXAMPLE 68

{2-Amino-4-[(5-(4-chlorophenyl)-2,5-diazabicyclo[2.2.1]hept-2-yl)methyl]thiophen-3-yl}(4-chlorophenyl)methanone

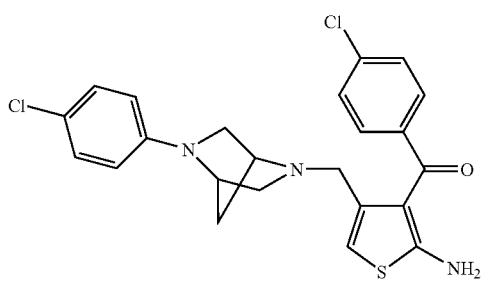

The title compound is purified by column chromatography (cyclohexane:EtOAc/8:2 as eluent). Mass (m/z): 458.64 (M+1). ¹H NMR (CDCl₃) δ: 1.62 (m, 2H), 2.04 (m, 1H), 2.35 (m, 1H), 2.79 (m, 2H), 2.96-3.12 (m, 4H), 6.01 (br s, 2H), 6.29 (d, 2H, J=8.8 Hz), 6.36 (m, 1H), 7.06 (d, 2H, J=8.8 Hz), 7.23 (d, 2H, j=8.4 Hz), 7.38 (d, 2H, J=8.4 Hz).

EXAMPLE 69

{2-Amino-4-[(4-(4-fluorophenyl)piperazin-1-yl)methyl]-5-methylthiophen-3-yl}(4-chlorophenyl)methanone

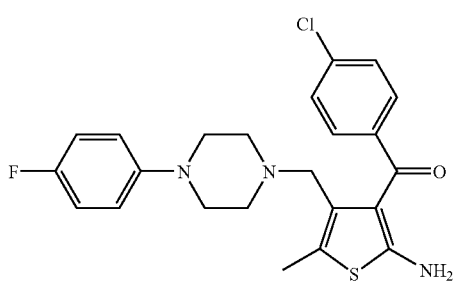

A. 2-[3-(4-Chlorobenzoyl)-4,5-dimethylthiophen-2-yl]isoindoline-1,3-dione

To a solution of (2-amino-4,5-dimethylthiophen-3-yl)(4-chlorophenyl)methanone (532 mg, 2 mmol; prepared as described in U.S. Pat. No. 6,323,214) in acetic acid (15 mL) is added phthalic anhydride (360 mg, 2.4 mmol) and the mixture is heated to reflux for 15 h. The solvent is evaporated in vacuo and the residual material is dissolved in ethyl acetate (20 mL). The organic solution is washed with a saturated aqueous solution of NaHCO₃ (5 mL), water (5 mL), then brine (5 mL), dried (Na₂SO₄), filtered, and concentrated in vacuo. The crude product is stirred for 1 h in petroleum ether (20 mL), then filtered, affording (2-[3-(4-chlorobenzoyl)-4,5-dimethylthiophen-2-yl]isoindoline-1,3-dione as a yellow powder. ¹H NMR (CDCl₃) δ: 2.10 (s, 3H), 2.43 (s, 3H), 7.24 (d, J=8.4 Hz, 2H), 7.64 (d, J=8.4 Hz, 2H), 7.78 (m, 4H).

B. 2-[4-(Bromomethyl)-3-(4-chlorobenzoyl)-5-methylthiophen-2-yl]isoindoline-1,3-dione To the title A compound (2 mmol, 798 mg) in acetonitrile (10 mL) is added N-bromosuccinimide (2 mmol, 356 mg.) and the mixture is heated at reflux for 2 h. After this time, another portion of N-bromosuccinimide (2 mmol, 356 mg.) is added and the reflux is continued for another 2 h. The solvent is then removed under reduced pressure, and the residue dissolved in DCM (15 mL), washed with water (5 mL), brine (5 mL), dried (Na₂SO₄), and concentrated to give a dark oil. This residue is then purified by flash chromatography (EtOAc:petroleum ether/2:8 as eluent) to furnish the compound as a yellow solid. The powder is suspended in petroleum ether (10 mL), the mixture is stirred for 30 min, and then filtered to give 2-[4-bromomethyl-3-(4-chlorobenzoyl)-5-methylthiophen-2-yl]isoindoline-1,3-dione: m.p. 173-175° C. ¹H NMR (CDCl₃) δ: 2.53 (s, 3H), 4.65 (s, 2H), 7.17 (d, J=8.4 Hz, 2H), 7.63 (d, J=8.4 Hz, 2H), 7.63 (m, 2H), 7.73 (m, 2H).

C. 2-[3-(4-Chlorobenzoyl)-4-((4-(4-fluorophenyl)piperazin-1-yl)methyl)-5-methylthiophen-2-yl]isoindoline-1,3-dione To a stirred solution of the title B compound (900 mg, 0.5 mmol) in dry DMF (5 mL) is added K₂CO₃ (0.6 mmol, 83 mg). The mixture is cooled with a bath of ice/water, and then the 1-(4-fluorophenyl)piperazine (3 equiv., 1.5 mmol) is added. The mixture is stirred at room temperature for one hour, the solvent is then removed under reduced pressure, and a mixture of DCM (15 mL) and water (5 mL) is added to the residue. The organic phase is washed with brine (5 mL) and dried (Na₂SO₄), filtered, then concentrated in vacuo to give a brown residue that is purified by column chromatography (ethyl acetate:DCM/1:9 as eluent) to afford 2-[3-(4-chlorobenzoyl)-4-((4-(4-fluorophenyl)piperazin-1-yl)methyl)-5-methylthiophen-2-yl]isoindoline-1,3-dione: m.p. 110-112° C. ¹H NMR (CDCl₃) δ: 2.23 (t, J=4.8 Hz, 4H), 2.42 (s, 3H), 2.72 (t, J=4.8 Hz, 4H), 3.23 (s, 2H), 6.60 (d, J=8.6 Hz, 1H), 6.64 (d, J=8.6 Hz, 1H), 6.85 (t, J=8.6 Hz, 2H), 7.32 (d, J=8.4 Hz, 2H), 7.61 (d, J=8.4 Hz, 2H), 7.68 (m, 2H), 7.72 (m, 2H).

D. {2-Amino-4-[(4-(4-fluorophenyl)piperazin-1-yl)methyl]-5-methylthiophen-3-yl}(4-chlorophenyl)methanone A stirred suspension of the title C compound (0.5 mmol) and hydrazine monohydrate (0.6 mmol, 29 µL) in absolute EtOH (10 mL) is heated to reflux for 3 h. The resulting solution is left cooled RT for 1 h. The reaction is finished after the complete solubilization of the starting material. The solvent is evaporated and the residue partitioned between DCM (10 mL) and water (5 mL). The separated organic phase is washed with brine (2 mL), dried (Na₂SO₄), filtered, and then concentrated in vacuo to obtain a residue that is purified by column chromatography (EtOAc:DCM/0.5:9.5 as eluent) to afford {2-amino-4-[(4-(4-fluorophenyl)piperazin-1-yl)methyl]-5-methylthiophen-3-yl}-(4-chlorophenyl)methanone as a yellow solid: m.p. 70-72° C. ¹H NMR (CDCl₃) δ: 1.99 (t, J=4.8 Hz, 4H), 2.23 (s, 3H), 2.83 (t, J=4.8 Hz, 4H), 2.96 (s, 2H), 5.82 (br s, 2H), 6.76 (d, J=8.6 Hz, 1H), 6.83 (d, J=8.6 Hz, 1H), 6.94 (t, J=8.6 Hz, 2H), 7.36 (d, J=8.4 Hz, 2H), 7.54 (d, J=8.4 Hz, 2H).

The following compounds are prepared analogously as described in Example 69.

EXAMPLE 70

{2-Amino-5-methyl-4-[(4-phenylpiperazin-1-yl)methyl]thiophen-3-yl}(4-chlorophenyl)methanone

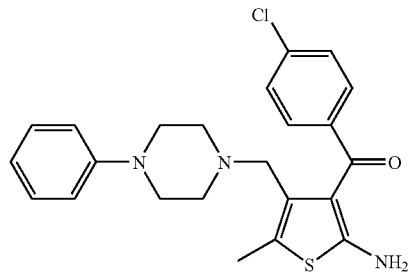

The title compound is purified by column chromatography (EtOAc:DCM/1:9 as eluent). Yellow solid, m.p. 78-80° C. $^1$H NMR (CDCl$_3$) δ: 1.98 (t, J=4.8 Hz, 4H), 2.22 (s, 3H), 2.91 (t, J=4.8 Hz, 4H), 2.95 (s, 2H), 5.80 (br s, 2H), 6.83 (d, J=8.4 Hz, 2H), 7.23 (t, J=8.4 Hz, 3H), 7.35 (d, J=8.4 Hz, 2H), 7.53 (d, J=8.4 Hz, 2H).

EXAMPLE 71

{2-Amino-5-methyl-4-[(4-(4-(trifluoromethyl)phenyl)piperazin-1-yl)methyl]thiophen-3-yl}(4-chlorophenyl)methanone

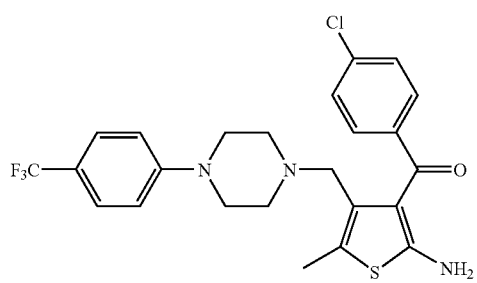

The title compound is purified by column chromatography (EtOAc:DCM/1:9 as eluent). Yellow solid, m.p. 76-78° C. $^1$H NMR (CDCl$_3$) δ: 2.04 (t, J=4.8 Hz, 4H), 2.22 (s, 3H), 2.95 (s, 2H), 3.00 (t, J=4.8 Hz, 4H), 5.82 (br s, 2H), 6.82 (d, J=8.4 Hz, 2H), 7.36 (d, J=8.4 Hz, 2H), 7.43 (d, J=8.4 Hz, 2H), 7.53 (d, J=8.4 Hz, 2H).

EXAMPLE 72

{2-Amino-4-[(4-(4-chlorophenyl)piperazin-1-yl)methyl]-5-methylthiophen-3-yl}(4-chlorophenyl)methanone

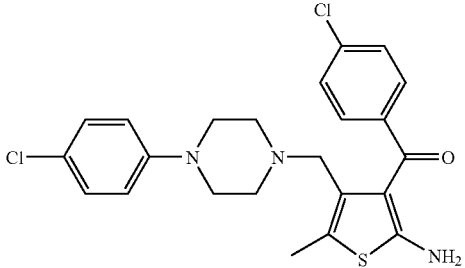

The title compound is purified by column chromatography (EtOAc:DCM/1:9 as eluent). Yellow solid, m.p. 83-85° C. $^1$H NMR (CDCl$_3$) δ: 1.98 (t, J=4.8 Hz, 4H), 2.22 (s, 3H), 2.87 (t, J=4.8 Hz, 4H), 2.95 (s, 2H), 5.80 (br s, 2H), 6.73 (d, J=9.2 Hz, 2H), 7.16 (d, J=9.2 Hz, 2H), 7.36 (d, J=8.4 Hz, 2H), 7.53 (d, J=8.4 Hz, 2H).

EXAMPLE 73

{2-Amino-4-[(4-(4-bromophenyl)piperazin-1-yl)methyl]-5-methylthiophen-3-yl}(4-chlorophenyl)methanone

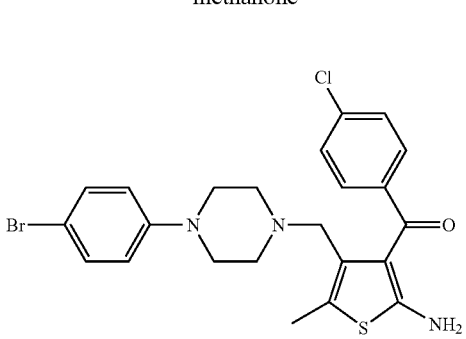

The title compound is purified by column chromatography (EtOAc:DCM/1:9 as eluent). Yellow solid, m.p. 73-75° C. $^1$H NMR (CDCl$_3$) δ: 1.96 (t, J=5.2 Hz, 4H), 2.22 (s, 3H), 2.87 (t, J=5.2 Hz, 4H), 2.94 (s, 2H), 5.81 (br s, 2H), 6.68 (d, J=9.2 Hz, 2H), 7.29 (d, J=9.2 Hz, 2H), 7.35 (d, J=8.4 Hz, 2H), 7.53 (d, J=8.4 Hz, 2H).

EXAMPLE 74

{2-Amino-4-[(4-(4-iodophenyl)piperazin-1-yl)methyl]-5-methylthiophen-3-yl}(4-chlorophenyl)methanone

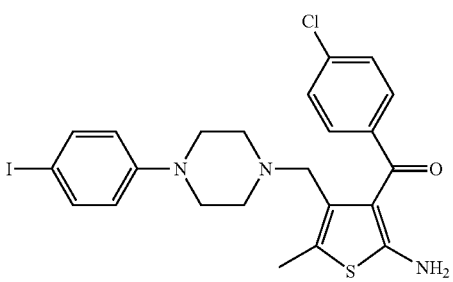

The title compound is purified by column chromatography (EtOAc:DCM/1:9 as eluent). Yellow solid, m.p. 72-73° C. $^1$H NMR (CDCl$_3$) δ: 1.99 (t, J=5.2 Hz, 4H), 2.04 (s, 3H), 2.89 (t, J=5.2 Hz, 4H), 2.98 (s, 2H), 5.80 (br s, 2H), 6.58 (d, J=8.8 Hz, 2H), 7.36 (d, J=8.4 Hz, 2H), 7.47 (d, J=8.8 Hz, 2H), 7.53 (d, J=8.4 Hz, 2H).

EXAMPLE 75

{2-Amino-5-methyl-4-[(4-(4-nitrophenyl)piperazin-1-yl)methyl]thiophen-3-yl}(4-chlorophenyl)methanone

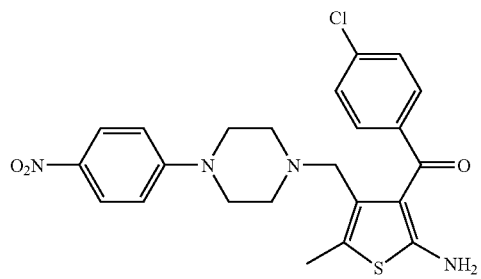

The title compound is purified by column chromatography (EtOAc:DCM/1:9 as eluent). Yellow solid, m.p. 85-87° C. $^1$H NMR (CDCl$_3$) δ: 1.98 (t, J=5.4 Hz, 4H), 2.331 (s, 3H), 3.08 (s, 2H), 3.11 (t, J=5.4 Hz, 4H), 6.26 (br s, 2H), 6.70 (d, J=8.8 Hz, 2H), 6.80 (d, J=9.2 Hz, 2H), 8.05 (d, J=9.2 Hz, 2H), 8.13 (d, J=8.8 Hz, 2H).

EXAMPLE 76

4-{4-[(5-Amino-4-(4-chlorobenzoyl)-2-methylthiophen-3-yl)methyl]piperazin-1-yl}benzonitrile

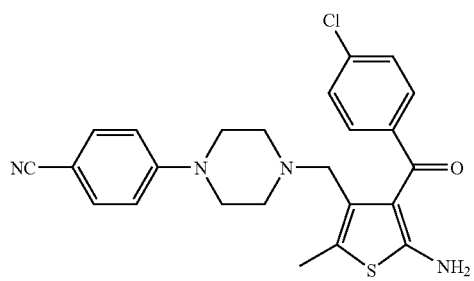

The title compound is purified by column chromatography (EtOAc:DCM/1:9 as eluent). Yellow solid, m.p. 76-77° C. $^1$H NMR (CDCl$_3$) δ: 1.96 (t, J=4.8 Hz, 4H), 2.21 (s, 3H), 2.95 (s, 2H), 3.04 (t, J=4.8 Hz, 4H), 5.84 (br s, 2H), 6.74 (d, J=8.8 Hz, 2H), 7.36 (d, J=8.4 Hz, 2H), 7.44 (d, J=8.8 Hz, 2H), 7.53 (d, J=8.4 Hz, 2H).

EXAMPLE 77

{2-Amino-4-[(4-benzylpiperazin-1-yl)methyl]-5-methylthiophen-3-yl}(4-chlorophenyl)methanone

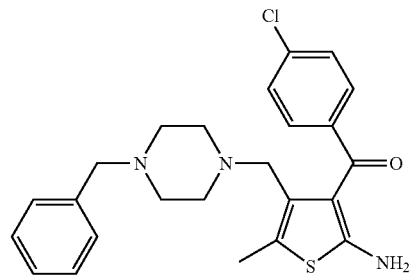

The title compound is purified by column chromatography (EtOAc as eluent). Yellow solid, m.p. 48-50° C. $^1$H NMR (CDCl$_3$) δ: 1.84 (t, J=5.2 Hz, 4H), 2.18 (s, 3H), 2.86 (t, J=5.2 Hz, 4H), 3.40 (s, 2H), 3.49 (s, 2H), 5.79 (br s, 2H), 7.26 (m, 5H), 7.33 (d, J=8.4 Hz, 2H), 7.51 (d, J=8.4 Hz, 2H).

EXAMPLE 78

{2-Amino-4-[(4-(4-methoxyphenyl)piperazin-1-yl)methyl]-5-methylthiophen-3-yl}(4-chlorophenyl)methanone

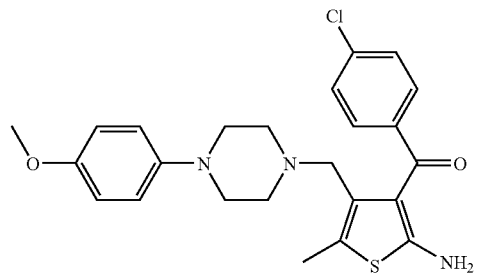

The title compound is purified by column chromatography (EtOAc:DCM/1.5:8.5 as eluent). Yellow solid, m.p. 63-65° C. $^1$H NMR (CDCl$_3$) δ: 1.98 (t, J=5.4 Hz, 4H), 2.21 (s, 3H), 2.80 (t, J=5.4 Hz, 4H), 2.94 (s, 2H), 3.75 (s, 3H), 5.81 (br s, 2H), 6.81 (s, 4H), 7.34 (d, J=8.4 Hz, 2H), 7.53 (d, J=8.4 Hz, 2H).

EXAMPLE 79

{2-Amino-5-methyl-4-[(4-p-tolylpiperazin-1-yl)methyl]thiophen-3-yl}(4-chlorophenyl)methanone

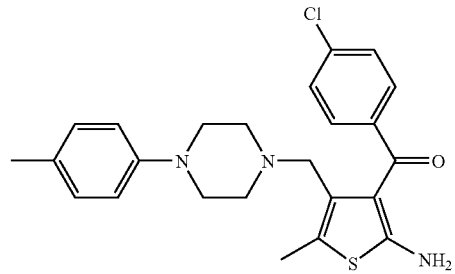

The title compound is purified by column chromatography (EtOAc:DCM/1:9 as eluent). Yellow solid, m.p. 77-79° C. $^1$H NMR (CDCl$_3$) δ: 1.98 (t, J=5.2 Hz, 4H), 2.22 (s, 3H), 2.25 (s, 3H), 2.85 (t, J=5.2 Hz, 4H), 2.94 (s, 2H), 5.81 (br s, 2H), 6.75 (d, J=8.8 Hz, 2H), 7.03 (d, J=8.8 Hz, 2H), 7.34 (d, J=8.4 Hz, 2H), 7.52 (d, J=8.4 Hz, 2H).

EXAMPLE 80

{2-Amino-4-[(4-(3,4-dichlorophenyl)piperazin-1-yl)methyl]-5-methylthiophen-3-yl}(4-chlorophenyl)methanone

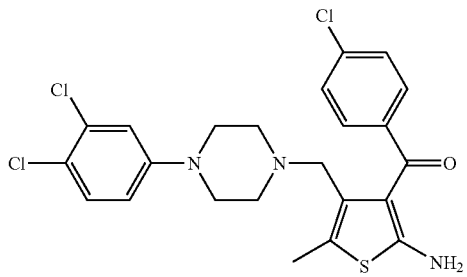

The title compound is purified by column chromatography (EtOAc:DCM/1:9 as eluent). Yellow solid, m.p. 63-65° C. $^1$H NMR (CDCl$_3$) δ: 1.96 (t, J=4.8 Hz, 4H), 2.22 (s, 3H), 2.88 (t, J=4.8 Hz, 4H), 2.94 (s, 2H), 5.82 (br s, 2H), 6.63 (dd, J=9.2 and 2.8 Hz, 1H), 6.86 (d, J=2.8 Hz, 1H), 7.22 (d, J=9.2 Hz, 1H), 7.36 (d, J=8.4 Hz, 2H), 7.53 (d, J=8.4 Hz, 2H).

EXAMPLE 81

{2-Amino-5-methyl-4-[(4-(3-(trifluoromethyl)phenyl)piperazin-1-yl)methyl]thiophen-3-yl}(4-chlorophenyl)methanone

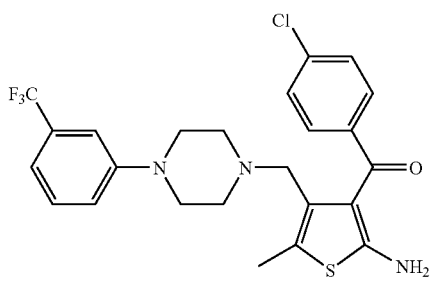

The title compound is purified by column chromatography (EtOAc:DCM/0.5:9.5 as eluent). Yellow solid, m.p. 60-61° C. $^1$H NMR (CDCl$_3$) δ: 1.99 (t, J=5.2 Hz, 4H), 2.22 (s, 3H), 2.96 (m, 6H), 5.81 (br s, 2H), 6.96 (d, J=7.6 Hz, 1H), 7.00 (s, 1H), 7.03 (d, J=7.6 Hz, 1H), 7.30 (t, J=7.6 Hz, 1H), 7.37 (d, J=8.4 Hz, 2H), 7.54 (d, J=8.4 Hz, 2H).

EXAMPLE 82

{2-Amino-4-[(4-(3-chlorophenyl)piperazin-1-yl)methyl]-5-methylthiophen-3-yl}(4-chlorophenyl)methanone

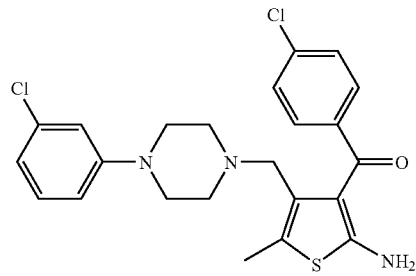

The title compound is purified by column chromatography (EtOAc:DCM/0.75:9.25 as eluent). Yellow solid, m.p. 58-60° C. $^1$H NMR (CDCl$_3$) δ: 1.96 (t, J=4.8 Hz, 4H), 2.22 (s, 3H), 2.92 (t, J=4.8 Hz, 4H), 3.00 (s, 2H), 5.82 (br s, 2H), 6.68 (d, J=7.6 Hz, 1H), 6.76 (d, J=7.6 Hz, 1H), 6.78 (s, 1H), 7.12 (t, J=8.4 Hz, 1H), 7.36 (d, J=8.4 Hz, 2H), 7.53 (d, J=8.4 Hz, 2H).

EXAMPLE 83

{2-Amino-4-[(4-(4-chloro-3-(trifluoromethyl)phenyl)piperazin-1-yl)methyl]-5-methylthiophen-3-yl}(4-chlorophenyl)methanone

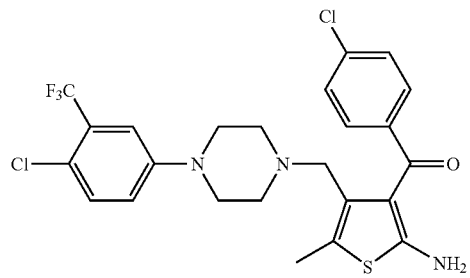

The title compound is purified by column chromatography (EtOAc:DCM/0.5:9.5 as eluent). Yellow solid, m.p. 133-135° C. $^1$H NMR (CDCl$_3$) δ: 1.98 (t, J=4.4 Hz, 4H), 2.22 (s, 3H), 2.93 (t, J=4.4 Hz, 4H), 2.96 (s, 2H), 5.82 (br s, 2H), 6.84 (dd, J=8.8 and 2.8 Hz, 1H), 7.07 (d, J=2.8 Hz, 1H), 7.29 (d, J=8.8 Hz, 1H), 7.37 (d, J=8.4 Hz, 2H), 7.54 (d, J=8.4 Hz, 2H).

EXAMPLE 84

{2-Amino-5-ethyl-4-[(4-(4-fluorophenyl)piperazin-1-yl)methyl]thiophen-3-yl}(4-chlorophenyl)methanone

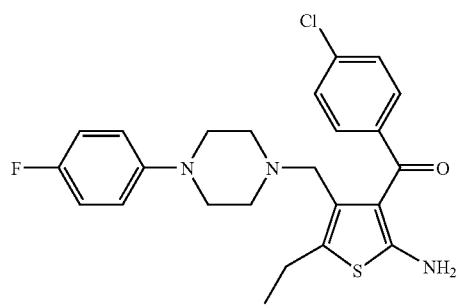

A. A mixture of (Z) and (E) 2-(4-chlorobenzoyl)-3-methylhex-2-enenitrile

A mixture of pentan-2-one (20 mmol), 3-(4-chlorophenyl)-3-oxopropanenitrile (3.6 g, 20 mmol), β-alanine (180 mg, 2 mmol), acetic acid (2.6 mL) and toluene (60 mL) is heated to reflux in a Dean-Stark system for 18 h. The solution is cooled to RT, then diluted with EtOAc (50 mL), washed with 5% NaHCO$_3$ (3×20 mL), water (20 mL), brine (20 mL), dried (Na$_2$SO$_4$) and finally concentrated in vacuo. A mixture of the two isomers is obtained as a colorless oil by chromatographic purification of the crude residue on silica gel using EtOAc:petroleum ether (0.5:9.5) as eluent.

B. (2-Amino-5-ethyl-4-methylthiophen-3-yl)(4-chlorophenyl)methanone

The title A compound(s) (5 mmol), TEA (0.7 mL, 5 mmol) and sulfur (192 mg, 6 mmol) in EtOH (10 mL) are heated at reflux for 2 h. After cooling to RT, the solvent is removed and the residue is dissolved in DCM (20 mL). The organic solution is washed with 0.1 N HCl (5 mL), 5% NaHCO$_3$ (5 mL), water (5 mL), brine (5 mL), dried (Na$_2$SO$_4$) and concentrated in vacuo. The crude residue was purified by chromatography on a silica gel column, eluting with EtOAc:petroleum ether (1:9) to afford (2-amino-5-ethyl-4-methylthiophen-3-yl)(4-chlorophenyl)methanone as a yellow oil. $^1$H-NMR (CDCl$_3$): δ 1.18 (t, J=7.6 Hz, 3H), 2.18 (s, 3H), 2.55 (q, J=7.6 Hz, 2H), 5.77 (bs, 2H), 7.36 (d, J=8.4 Hz, 2H), 7.46 (d, J=8.4 Hz, 2H).

C. 2-[3-(4-Chlorobenzoyl)-4-methyl-5-ethyl-thiophen-2-yl]-isoindole-1,3-dione The title B compound (4 mmol) is dissolved in acetic acid (25 mL). To the solution is added phthalic anhydride (5 mmol, 740 mg) and the mixture is heated under reflux for 5 h. The solvent is evaporated in vacuo and the residual material is dissolved in DCM (30 mL). The organic solution is washed with water (10 mL), brine (10 mL), dried (Na$_2$SO$_4$) and concentrated in vacuo. The crude product is first triturated for 1 h in petroleum ether (20 mL), then purified by column chromatography (EtOAc:petroleum ether/2:8 as eluent) to afford 2-[3-(4-chlorobenzoyl)-4-methyl-5-ethyl-thiophen-2-yl]-isoindole-1,3-dione as a white solid: m.p. 115-117° C. $^1$H-NMR (CDCl$_3$): δ 1.34 (t, J=7.6 Hz, 3H), 2.17 (s, 3H), 2.82 (q, J=7.6 Hz, 2H), 7.26 (d, J=8.8 Hz, 2H), 7.69 (d, J=8.4 Hz, 2H), 7.77 (m, 2H), 7.79 (m, 2H).

D. 2-[5-Ethyl-4-bromomethyl-3-(4-chloro-benzoyl)-thiophen-2-yl]-isoindole-1,3-dione To a solution of title C compound (2 mmol) in CCl$_4$ (40 mL), a mixture of N-bromosuccinimide (784 mg, 4.4 mmol) and benzoyl peroxide (32 mg) is added and the mixture refluxed for 2 h. The resulting yellow solution is then cooled to RT, during which succinimide separates and is removed by filtration. The filtrate is concentrating in vacuo, and the residue is diluted with DCM (20 mL). The organic solution is washed with 5% NaHCO$_3$ (10 mL), water (10 mL), brine (10 mL), dried (Na$_2$SO$_4$) and concentrated to give a yellow residue which is purified by column chromatography (EtOAc:petroleum ether/2:8 as eluent) to give 2-[5-ethyl-4-bromomethyl-3-(4-chloro-benzoyl)-thiophen-2-yl]-isoindole-1,3-dione as an orange oil. $^1$H-NMR (CDCl$_3$): δ 1.39 (t, J=7.6 Hz, 3H), 2.96 (q, J=7.6 Hz, 2H), 4.66 (s, 2H), 7.17 (d, J=7.6 Hz, 2H), 7.64 (d, J=7.6 Hz, 2H), 7.73 (m, 2H), 7.76 (m, 2H).

E. 2-{3-(4-Chlorobenzoyl)-4-[4-(4-fluorophenyl)-piperazin-1-ylmethyl-5-ethyl]-thiophen-2-yl}-isoindole-1,3-dione To an ice/water cooled, stirred solution of the title D compound (0.5 mmol) in dry DMF (2.5 mL) is added TEA (0.12 mL, 1 mmol) and then the appropriate 1-(4-fluorophenyl)piperazine (0.6 mmol). The mixture is then stirred at RT for 2 h. The solvent is removed under reduced pressure, the residue dissolved in DCM (10 mL), and washed with water (5 mL), brine (5 mL), and dried (Na$_2$SO$_4$). After evaporation under vacuum, the residue is purified by column chromatography on silica gel (EtOAc:petroleum ether/1.5:8.5 as eluent) to afford 2-{3-(4-chlorobenzoyl)-4-[4-(4-fluorophenyl)-piperazin-1-ylmethyl-5-ethyl]-thiophen-2-yl}-isoindole-1,3-dione as a white solid: m.p. 122-124° C. $^1$H NMR (CDCl$_3$): δ 1.20 (t, J=7.6 Hz, 3H), 1.99 (m. 4H), 2.68 (q, J=7.6 Hz, 2H), 3.02 (m, 4H), 3.22 (s, 2H), 6.84 (d, J=8.4 Hz, 2H), 7.21 (d, J=8.4 Hz, 2H), 7.38 (d, J=8.4 Hz, 2H), 7.52 (d, J=8.4 Hz, 2H), 7.72 (m, 2H), 7.84 (m, 2H).

F. {2-Amino-4-[4-(4-fluorophenyl)piperazin-1-yl)methyl]-5-ethylthiophen-3-yl}(4-chlorophenyl)methanone A stirred suspension of the title E compound (0.25 mmol) and 100% hydrazine monohydrate (0.3 mmol, 14 μL) in absolute EtOH (5 mL) is refluxed for 3 h. The solvent is evaporated and the residue is partitioned between DCM (10 mL) and water (5 mL). The separated organic phase is washed with brine (2 mL) and dried, then concentrated in vacuo to obtain a residue which is purified by column chromatography (EtOAc:DCM/8:2 as eluent) to give {2-amino-4-[4-(4-fluorophenyl)piperazin-1-yl)methyl]-5-ethylthiophen-3-yl}(4-chlorophenyl)methanone as a yellow solid: m.p. 123-125° C. $^1$H-NMR (CDCl$_3$): δ 1.21 (t, J=7.6 Hz, 3H), 1.98 (m. 4H), 2.61 (q, J=7.6 Hz, 2H), 2.84 (m, 4H), 2.96 (s, 2H), 5.77 (bs, 2H), 6.82 (m, 2H), 6.93 (d J=9.0 Hz, 2H), 7.34 (d J=8.6 Hz, 2H), 7.57 (d, J=8.6 Hz, 2H).

The following compounds are prepared analogously as described in Example 84.

EXAMPLE 85

{2-Amino-5-ethyl-4-[(4-phenylpiperazin-1-yl)methyl]thiophen-3-yl}(4-chlorophenyl)methanone

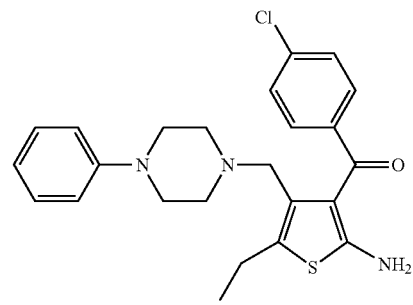

The title compound is purified by column chromatography (EtOAc:petroleum ether/1.5:8.5 as eluent). Yellow solid, m.p. 104-106° C. $^1$H-NMR (CDCl$_3$): δ 1.22 (t, J=7.6 Hz, 3H), 1.98 (m. 4H), 2.64 (q, J=7.6 Hz, 2H), 2.92 (m, 4H), 2.96 (s, 2H), 5.78 (bs, 2H), 6.85 (m 3H), 7.23 (m, 2H), 7.37 (d, J=8.4 Hz, 2H), 7.56 (d, J=8.4 Hz, 2H).

EXAMPLE 86

{2-Amino-4-[(4-(4-chlorophenyl)piperazin-1-yl)methyl]-5-ethylthiophen-3-yl}(4-chlorophenyl)methanone

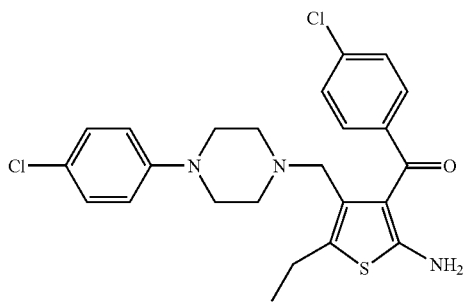

The title compound is purified by column chromatography (EtOAc:petroleum ether/1.5:8.5 as eluent). Yellow solid, m.p. 115-117° C. $^1$H-NMR (CDCl$_3$): δ 1.23 (t, J=7.6 Hz, 3H), 1.97 (m, 4H), 2.61 (q, J=7.6 Hz, 2H), 2.88 (m, 4H), 2.96 (s, 2H), 5.77 (bs, 2H), 6.72 (d J=9.0 Hz, 2H), 7.19 (d J=9.0 Hz, 2H), 7.34 (d J=8.2 Hz, 2H), 7.52 (d, J=8.2 Hz, 2H).

EXAMPLE 87

{2-Amino-5-phenyl-4-[(piperidin-1-yl)methyl]thiophen-3-yl}(4-chlorophenyl)methanone

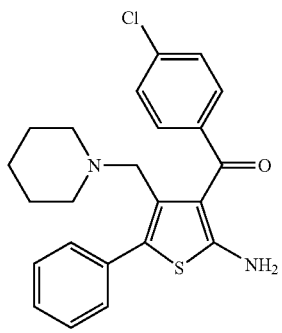

A. 2-[3-(4-Chlorobenzoyl)-4-methyl-5-phenylthiophen-2-yl]isoindole-1,3-dione The title A compound is prepared from the title C compound of Example 1 following the procedure described by Romagnoli et al. in *J. Med. Chem.* 2006, 49(13), 3906-3915. The product is purified by column chromatography (eluent EtOAc:petroleum ether/1.5:8.5 as eluent) to afford 2-[3-(4-chlorobenzoyl)-4-methyl-5-phenylthiophen-2-yl]isoindole-1,3-dione as a brown solid, m.p. 223-225° C. $^1$H NMR (CDCl$_3$) δ: 2.24 (s, 3H), 7.24 (d, J=8.4 Hz, 2H), 7.74 (m, 5H), 7.80 (m, 6H).

B. 2-[4-Bromomethyl-3-(4-chlorobenzoyl)-5-phenylthiophen-2-yl]isoindole-1,3-dione To a refluxing suspension of the title A compound (458 mg, 1 mmol) in CCl$_4$ (10 mL), is added NBS (180 mg, 1 mmol) and benzoyl peroxide (14 mg, 0.06 mmol) and the mixture is refluxed for 1 h. After this time, a mixture of N-bromosuccinimide (180 mg, 1 mmol.) and benzoyl peroxide (14 mg, 0.06 mmo) is added and the mixture refluxed for another hour. The yellow solution is then cooled to RT, and succinimide that separates upon cooling is removed by filtration and the filtercake is washed with CCl$_4$ (5 mL). The filtrate is washed with 5% NaHCO$_3$ solution (5 mL), water (5 mL), brine (50 mL), dried over Na$_2$SO$_4$, and concentrated to give a yellow solid which is suspended with petroleum ether (10 mL). The mixture is stirred for 30 min, and the solid is collected by filtration to afford 2-[4-bromomethyl-3-(4-chlorobenzoyl)-5-phenylthiophen-2-yl]isoindole-1,3-dione which is used as such for the next reaction without further purification, m.p. 160-161° C. $^1$H NMR (CDCl$_3$) δ: 4.73 (s, 2H), 7.21 (d, J=8.6 Hz, 2H), 7.48 (d, J=8.6 Hz, 2H), 7.52 (m, 1H), 7.68 (m, 8H).

C. 2-[3-(4-Chlorobenzoyl)-5-phenyl-4-((piperidin-1-yl)methyl)thiophen-2-yl]isoindole-1,3-dione To a stirred solution of the title B compound (265 mg, 0.5 mmol) in dry DMF (5 mL) is added K$_2$CO$_3$ (70 mg, 0.5 mmol). The mixture is cooled with a bath of ice/water, and then piperidine (4 equiv., 2 mmol) is added. The mixture is stirred at RT for 2 h. After this time, the solvent is removed under reduced pressure, and the residue is taken up in a mixture of EtOAc (15 mL) and water (5 mL). The organic phase is washed with brine (5 mL), dried over Na$_2$SO$_4$, and concentrated under vacuo to give a brown residue which is purified by column chromatography (EtOAc:petroleum ether/1.5:8.5 as eluent) to afford 2-[3-(4-chlorobenzoyl)-5-phenyl-4-((piperidin-1-yl)methyl)thiophen-2-yl]isoindole-1,3-dione as a yellow solid, m.p. 187-189° C. $^1$H NMR (CDCl$_3$) δ: 1.25 (m, 6H), 1.65 (m, 4H), 2.98 (s, 2H), 7.22 (d, J=8.8 Hz, 2H), 7.53 (m, 3H), 7.73 (m, 8H).

D. {2-Amino-5-phenyl-4-[(piperidin-1-yl)methyl]thiophen-3-yl}(4-chlorophenyl)methanone A stirred suspension of the title C compound (0.5 mmol) and 100% hydrazine monohydrate (1.2 eq, 0.6 mmol, 29 µL) in absolute ethanol (10 mL) is refluxed for 1 h. After this time, the solvent is evaporated and the residue is portioned between EtOAc (10 mL) and water (5 mL). The separated organic phase is washed with brine (2 mL), dried, and concentrated under vacuo to obtain a residue which is purified by column chromatography (EtOAc:petroleum ether/4:6 as eluent) to give {2-amino-5-phenyl-4-[(piperidin-1-yl)methyl]thiophen-3-yl}(4-chlorophenyl)methanone as a yellow solid, m.p. 185-187° C. $^1$H NMR (CDCl$_3$) δ: 1.24 (m, 6H), 1.66 (m, 4H), 2.99 (s, 2H), 5.69 (br s, 2H), 7.33 (m, 7H), 7.65 (d, J=8.6 Hz, 2H).

EXAMPLE 88

Example of a Scale-Up Synthesis

{2-Amino-4-[(4-(3-fluorophenyl)piperazin-1-yl)methyl]-5-methylthiophen-3-yl}(4-chlorophenyl)methanone

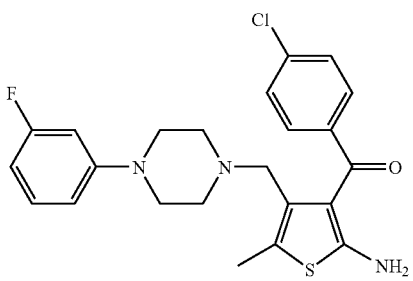

A. (2-Amino-4,5-dimethylthiophen-3-yl)(4-chlorophenyl)methanone

A 12 L, 3 neck round bottom flask equipped with a mechanical stirrer and a thermometer is charged with 3-(4-chlorophenyl)-3-oxopropanenitrile (800 g, 4.46 mol), absolute EtOH (4 L), sulphur (321 g, 4.46 mol) and ethylmethylketone (321 g, 4.46 mol). Morpholine (388 g, 4.46 mol) is added and the reaction mixture thickens, and the temperature increases from 18° C. to 30° C. The reaction mixture is stirred for 1 h at ambient temperature, heated at reflux overnight, then cooled to ambient temperature and concentrated in vacuo. The residue is combined with a previous batch of crude material from a 500 g reaction. The combined residues are taken up in EtOAc (12 L), washed with water (6 L), 10% NaHSO$_4$ (3 L) and brine (2 L), dried over anhydrous NaSO$_4$ and filtered through Celite. The filtrate is concentrated in vacuo to give a gummy solid. The solids are collected by filtration, washed with hexanes and air dried to yield (2-amino-4,5-dimethylthiophen-3-yl)(4-chlorophenyl)methanone as a tan coloured solid (680 g).

B. 2-[3-(4-Chlorobenzoyl)-4,5-dimethylthiophen-2-yl]isoindoline-1,3-dione

A 12 L, 3 neck round bottom flask equipped with a mechanical stirrer and a thermometer is charged with the title A compound (800 g, 3.01 mol), acetic acid (6 L), and phthalic anhydride (535 g, 3.62 mol). The reaction mixture is stirred at reflux overnight, then allowed to cool to ambient temperature and concentrated in vacuo. Methyl-t-butylether (MTBE, 2 L) is added to the residue, and the resulting slurry is filtered. The solids are washed with MTBE (500 mL) and hexanes (1 L), then air dried to yield 2-[3-(4-chlorobenzoyl)-4,5-dimethylthiophen-2-yl]isoindoline-1,3-dione as a tan colored solid (1050 g). The $^1$H NMR spectrum is consistent with the structure.

C. 2-[4-(Bromomethyl)-3-(4-chlorobenzoyl)-5-methylthiophen-2-yl]isoindoline-1,3-dione A three-neck 3 L round bottom flask equipped with a mechanical stirrer and a thermometer is charged with the title B compound (150 g, 0.38 mol), N-bromosuccinimide (67 g, 0.38 mol), and acetonitrile (1.5 L). The reaction mixture is stirred at reflux for 2 h, then treated with more N-bromosuccinimide (67 g, 0.38 mol). Heating at refluxing is continued for 2 h more, and the reaction mixture is allowed to cool to ambient temperature, and concentrated in vacuo. The residue is taken up in DCM (600 mL) and washed with water (200 mL), saturated NaHCO$_3$ (200 mL), water (200 mL), and brine (200 mL), dried (Na$_2$SO$_4$), filtered, and concentrated in vacuo. The dark brown solid is purified by chromatography (DCM as eluent) to yield a tan solid which is slurried in diethyl ether (Et$_2$O, 300 mL), then filtered and dried to afford 2-[4-(bromomethyl)-3-(4-chlorobenzoyl)-5-methylthiophen-2-yl]isoindoline-1,3-dione as an off-white solid (86 g). The $^1$H NMR spectrum is consistent with the structure.

D. 2-[3-(4-Chlorobenzoyl)-4-((4-(3-fluorophenyl)piperazin-1-yl)methyl)-5-methylthiophen-2-yl]isoindoline-1,3-dione A 2 L round bottom flask equipped with a mechanical stirrer is charged with the title C compound (80.7 g, 0.17 mol), CHCl$_3$ (1.2 L), and triethylamine (3 equiv). The mixture is cooled in an ice/water bath to ~5° C., then the appropriate 4-(3-fluorophenyl)piperazine (0.9 equiv) is added. The reaction mixture is stirred at 0° C. for 5 min, then at ambient temperature for 1 h. The reaction mixture is washed with water (500 mL), saturated NaHCO$_3$ (500 mL), and brine (500 mL), then dried over anhydrous Na$_2$SO$_4$, filtered and concentrated in vacuo to half volume. The crude material was purified by chromatography (2% EtOAc in DCM). The eluent is concentrated in vacuo, then slurried in Et$_2$O (300 mL), filtered and dried to give 2-[3-(4-chlorobenzoyl)-4-((4-(3-fluorophenyl)piperazin-1-yl)methyl)-5-methylthiophen-2-yl]isoindoline-1,3-dione (40 g) as an off-white solid.

E. {2-Amino-4-[(4-(3-fluorophenyl)piperazin-1-yl)methyl]-5-methylthiophen-3-yl}(4-chlorophenyl)methanone A 2 L round bottom flask is charged with the title D compound (40 g, 0.07 mol), toluene (0.2 M), and EtOH (0.2 M). Hydrazine hydrate (1.5 equiv, 64% hydrazine) is added in one portion, and the mixture is heated to reflux. Upon reaching the reflux temperature, the reaction mixture becomes a clear yellow solution, and upon continued heating a precipitate is formed. The reaction is monitored by TLC, and when the reaction is complete (usually ~5 h), the reaction mixture is allowed to cool to ambient temperature and concentrated. The residue is taken up in Et$_2$O (600 mL), washed with water (150 mL), saturated NaHCO$_3$ (150 mL), and brine (150 mL), then dried (Na$_2$SO$_4$). The solvent is removed in vacuo, and the resulting yellow solid is stirred in ethanol (80 mL) then filtered and dried to afford {2-amino-4-[(4-(3-fluorophenyl)piperazin-1-yl)methyl]-5-methylthiophen-3-yl}(4-chlorophenyl)methanone as a yellow solid (24 g), m.p. 140-141° C. ESI-MS: 444 (M+H)$^+$. Elemental Analysis: calc C, 62.22%, H, 5.22%, N, 9.46%. found C, 62.21%, H, 5.27%, N, 9.48%. $^1$H NMR (200 MHz, CDCl$_3$): δ 7.54 (d, J=8.4 Hz, 2H), 7.37 (d, J=8.4 Hz), 7.09-7.21 (m, 1H), 6.46-6.59 (m, 3H), 5.82 (s, 2H), 2.89-2.95 (m, 6H), 2.22 (s, 3H), 1.95-1.99 (m, 4H).

What is claimed is:

1. A compound of formula (I)

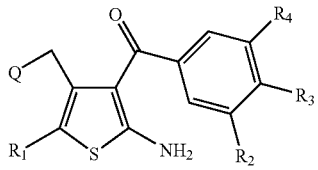

wherein
- $R_1$ is hydrogen, alkyl, substituted alkyl, aryl, substituted aryl, cycloalkyl or substituted cycloalkyl;
- $R_2$, $R_3$, and $R_4$ are, independently from each other, hydrogen, alkyl, substituted alkyl, aryl, substituted aryl, cycloalkyl, substituted cycloalkyl, halogen, hydroxyl, nitro, cyano, alkoxy or substituted alkoxy;
- Q is

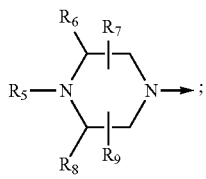

in which
- $R_5$ is hydrogen, alkyl, substituted alkyl, aryl, substituted aryl, cycloalkyl, substituted cycloalkyl, heteroaryl, substituted heteroaryl, heteroaralkyl, substituted heteroaralkyl, acyl or substituted acyl;
- $R_6$ and $R_7$ are, independently from each other, hydrogen, $C_1$-$C_3$ alkyl or $C_1$-$C_3$ substituted alkyl; or
- $R_6$ and $R_7$, provided they are attached to the same carbon atom, combined are alkylene which together with the carbon atom to which they are attached form a 3- to 7-membered spirocyclic ring;
- $R_8$ and $R_9$ are, independently from each other, hydrogen, $C_1$-$C_3$ alkyl or $C_1$-$C_3$ substituted alkyl;
- X is N;

or a pharmaceutically acceptable salt thereof.

2. A compound according to claim 1, wherein
$R_1$ is hydrogen, alkyl, substituted alkyl, aryl or substituted aryl;
or a pharmaceutically acceptable salt thereof.

3. A compound according to claim 2 of formula (IA)

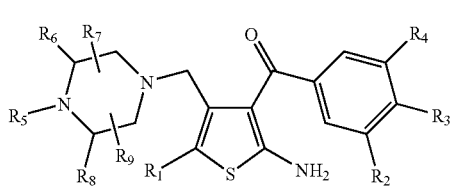

wherein
- $R_1$ is hydrogen, alkyl, substituted alkyl, aryl or substituted aryl;
- $R_2$, $R_3$, and $R_4$ are, independently from each other, hydrogen, alkyl, substituted alkyl, aryl, substituted aryl, cycloalkyl, substituted cycloalkyl, halogen, hydroxyl, nitro, cyano, alkoxy or substituted alkoxy;
- $R_5$ is alkyl, substituted alkyl, aryl, substituted aryl, cycloalkyl, substituted cycloalkyl, heteroaryl, substituted heteroaryl, heteroaralkyl, substituted heteroaralkyl, acyl or substituted acyl;
- $R_6$, $R_7$, $R_8$ and $R_9$ are, independently from each other, hydrogen, $C_1$-$C_3$ alkyl or $C_1$-$C_3$ substituted alkyl;

or a pharmaceutically acceptable salt thereof.

4. A compound according claim 3, wherein
$R_1$ is hydrogen or $C_1$-$C_3$ alkyl;
or a pharmaceutically acceptable salt thereof.

5. A compound according to claim 3, wherein
$R_5$ is monocyclic aryl optionally substituted by one to three substituents selected from the group consisting of halogen, cyano or trifluoromethyl;
or a pharmaceutically acceptable salt thereof.

6. A compound according to claim 3, wherein
$R_2$ and $R_4$ are hydrogen;
or a pharmaceutically acceptable salt thereof.

7. A compound according to claim 6, wherein
$R_3$ is halogen, cyano or trifluoromethyl;
or a pharmaceutically acceptable salt thereof.

8. A compound according to claim 3, wherein
$R_2$ and $R_3$ are hydrogen;
or a pharmaceutically acceptable salt thereof.

9. A compound according to claim 8, wherein
$R_4$ is halogen, cyano or trifluoromethyl;
or a pharmaceutically acceptable salt thereof.

10. A compound according to claim 3, wherein
$R_6$, $R_7$, $R_8$ and $R_9$ are, independently from each other, hydrogen or $C_1$-$C_3$ alkyl;
or a pharmaceutically acceptable salt thereof.

11. A compound according to claim 10, wherein
$R_5$ is monocyclic aryl optionally substituted by one to three substituents selected from the group consisting of halogen, cyano or trifluoromethyl;
or a pharmaceutically acceptable salt thereof.

12. A compound according to claim 11, wherein
$R_2$ and $R_4$ are hydrogen;
or a pharmaceutically acceptable salt thereof.

13. A compound according to claim 12, wherein
$R_3$ is halogen, cyano or trifluoromethyl;
or a pharmaceutically acceptable salt thereof.

14. A compound according claim 13, wherein
$R_1$ is hydrogen or $C_1$-$C_3$ alkyl;
or a pharmaceutically acceptable salt thereof.

15. A compound according to claim 11, wherein
$R_2$ and $R_3$ are hydrogen;
or a pharmaceutically acceptable salt thereof.

16. A compound according to claim 15, wherein
$R_4$ is halogen, cyano or trifluoromethyl;
or a pharmaceutically acceptable salt thereof.

17. A compound according claim 16, wherein
$R_1$ is hydrogen or $C_1$-$C_3$ alkyl;
or a pharmaceutically acceptable salt thereof.

18. A compound selected from the group consisting of:
{2-Amino-4-[(4-phenylpiperazin-1-yl)methyl]thiophen-3-yl}(4-chlorophenyl)methanone;
{2-Amino-4-[(4-methylpiperazin-1-yl)methyl]thiophen-3-yl}(4-chlorophenyl)methanone;
{2-Amino-4-[4-((4-fluorophenyl)piperazin-1-yl)methyl]thiophen-3-yl}(4-chlorophenyl)methanone;
{2-Amino-4-[4-((4-chlorophenyl)piperazin-1-yl)methyl]thiophen-3-yl}(4-chlorophenyl)methanone;
{2-Amino-4-[4-((4-methoxyphenyl)piperazin-1-yl)methyl]thiophen-3-yl}(4-chlorophenyl)methanone;

{2-Amino-4-[(4-p-tolylpiperazin-1-yl)methyl]thiophen-3-yl}(4-chlorophenyl)methanone;
{2-Amino-4-[(4-(pyridin-2-yl)piperazin-1-yl)methyl]thiophen-3-yl}(4-chlorophenyl)methanone;
{2-Amino-4-[(4-(pyrimidin-2-yl)piperazin-1-yl)methyl]thiophen-3-yl}(4-chlorophenyl)methanone;
{2-Amino-4-[(4-(3,4-dichlorophenyl)-piperazin-1-yl)methyl]thiophen-3-yl}(4-chlorophenyl)methanone;
4-{4-[(5-Amino-4-(4-chlorobenzoyl)thiophen-3-yl)methyl]piperazin-1-yl}benzonitrile;
{2-Amino-4-[(4-(3-chlorophenyl)-piperazin-1-yl)methyl]thiophen-3-yl}(4-chlorophenyl)methanone;
{2-Amino-4-[(4-(2-chlorophenyl)piperazin-1-yl)methyl]thiophen-3-yl}(4-chlorophenyl)methanone;
{2-Amino-4-[(4-(2-fluorophenyl)-piperazin-1-yl)methyl]thiophen-3-yl}(4-chlorophenyl)methanone;
{2-Amino-4-[(4-(3-(trifluoromethyl)phenyl)piperazin-1-yl)methyl]thiophen-3-yl}(4-chlorophenyl)methanone;
1-{4-[(5-Amino-4-(4-chlorobenzoyl)thiophen-3-yl)methyl]piperazin-1-yl}-2-(4-chlorophenyl)ethanone;
{2-Amino-4-[(4-(4-chlorobenzoyl)piperazin-1-yl)methyl]thiophen-3-yl}(4-chlorophenyl)methanone;
{2-Amino-4-[(4-(pyridin-4-yl)piperazin-1-yl)methyl]thiophen-3-yl}(4-chlorophenyl)methanone;
{2-Amino-4-[(4-(benzo[d][1,3]dioxol-5-yl)piperazin-1-yl)methyl]thiophen-3-yl}(4-chlorophenyl)methanone;
{2-Amino-4-[(4-(2,3-dichlorophenyl)piperazin-1-yl)methyl]thiophen-3-yl}(4-chlorophenyl)methanone;
{2-Amino-4-[(4-(3-fluorophenyl)piperazin-1-yl)methyl]thiophen-3-yl}(4-chlorophenyl)methanone;
{2-Amino-4-[(4-(3,5-dichlorophenyl)piperazin-1-yl)methyl]thiophen-3-yl}(4-chlorophenyl)methanone;
{2-Amino-4-[(4-(4-(trifluoromethyl)phenyl)piperazin-1-yl)methyl]thiophen-3-yl}(4-chlorophenyl)methanone;
2-{4-[(5-Amino-4-(4-chlorobenzoyl)thiophen-3-yl)methyl]piperazin-1-yl}-1-(4-chlorophenyl)ethanone;
{2-Amino-4-[(4-(2,4-difluorophenyl)piperazin-1-yl)methyl]thiophen-3-yl}(4-chlorophenyl)methanone;
{2-Amino-4-[(4-(2,6-difluorophenyl)piperazin-1-yl)methyl]thiophen-3-yl}(4-chlorophenyl)methanone;
{2-Amino-4-[(4-(3-chloro-4-fluorophenyl)piperazin-1-yl)methyl]thiophen-3-yl}(4-chlorophenyl)methanone;
{2-Amino-4-[(4-cyclohexylpiperazin-1-yl)methyl]thiophen-3-yl}(4-chlorophenyl)methanone;
{2-Amino-4-[(4-nitrophenyl)piperazin-1-yl)methyl]thiophen-3-yl}(4-chlorophenyl)methanone;
{2-Amino-4-[(4-isopropyl)piperazin-1-yl)methyl]thiophen-3-yl}(4-chlorophenyl)methanone;
{2-Amino-4-[(4-naphthalen-1-yl)piperazin-1-yl)methyl]thiophen-3-yl}(4-chlorophenyl)methanone;
{2-Amino-4-[(4-(3,4-difluorophenyl)piperazin-1-yl)methyl]thiophen-3-yl}(4-chlorophenyl)methanone;
{2-Amino-4-[(4-cyclopentylpiperazin-1-yl)methyl]thiophen-3-yl}(4-chlorophenyl)methanone;
{2-Amino-4-[(4-cycloheptylpiperazin-1-yl)methyl]thiophen-3-yl}(4-chlorophenyl)methanone;
{2-Amino-4-[(4-(4-chlorobenzyl)piperazin-1-yl)methyl]thiophen-3-yl}(4-chlorophenyl)methanone;
{2-Amino-4-[(4-benzylpiperazin-1-yl)methyl]thiophen-3-yl}(4-chlorophenyl)methanone;
(2-Amino-4-{[4-(2-(4-chlorophenyl)ethyl)piperazin-1-yl]methyl}thiophen-3-yl)(4-chlorophenyl)methanone;
{2-Amino-4-[(4-(4-fluorobenzyl)piperazin-1-yl)methyl]thiophen-3-yl}(4-chlorophenyl)methanone;
{2-Amino-4-[(4-cyclooctylpiperazin-1-yl)methyl]thiophen-3-yl}(4-chlorophenyl)methanone;

(2-Amino-4-{[4-[3-(4-chlorophenyl)propyl]piperazin-1-yl]methyl}thiophen-3-yl)(4-chlorophenyl)methanone;
{2-Amino-4-[(4-(2,4-dichlorophenyl)piperazin-1-yl)methyl]thiophen-3-yl}(4-chlorophenyl)methanone;
{2-Amino-4-[(4-(2,5-difluorophenyl)piperazin-1-yl)methyl]thiophen-3-yl}(4-chlorophenyl)methanone;
{2-Amino-4-[(4-(2-(trifluoromethyl)phenyl)piperazin-1-yl)methyl]thiophen-3-yl}(4-chlorophenyl)methanone;
{2-Amino-4-[(4-(4-chloro-3-(trifluoromethyl)phenyl)piperazin-1-yl)methyl]thiophen-3-yl}(4-chlorophenyl)methanone;
{2-Amino-4-[(4-(2,4,6-trifluorophenyl)piperazin-1-yl)methyl]thiophen-3-yl}(4-chlorophenyl)methanone;
{2-Amino-4-[(4-(2-chloro-4-fluorophenyl)piperazin-1-yl)methyl]thiophen-3-yl}(4-chlorophenyl)methanone;
{2-Amino-4-[(4-(2-fluoro-4-chlorophenyl)piperazin-1-yl)methyl]thiophen-3-yl}(4-chlorophenyl)methanone;
{2-Amino-4-[(4-(3,5-diflourophenyl)piperazin-1-yl)methyl]thiophen-3-yl}(4-chlorophenyl)methanone;
{2-Amino-4-[(4-(2,6-dichlorophenyl)piperazin-1-yl)methyl]thiophen-3-yl}(4-chlorophenyl)methanone;
{2-Amino-4-[(4-(4-(trifluoromethoxy)phenyl)piperazin-1-yl)methyl]thiophen-3-yl}(4-chlorophenyl)methanone;
{2-Amino-4-[(4-(pyridin-3-yl)piperazin-1-yl)methyl]thiophen-3-yl}(4-chlorophenyl)methanone;
{2-Amino-4-[(4-(2,5-dichlorophenyl)piperazin-1-yl)methyl]thiophen-3-yl}(4-chlorophenyl)methanone;
{2-Amino-4-[(4-(2,3-difluorophenyl)piperazin-1-yl)methyl]thiophen-3-yl}(4-chlorophenyl)methanone;
{2-Amino-4-[(4-(4-chlorophenyl)-3-methylpiperazin-1-yl)methyl]thiophen-3-yl}(4-chlorophenyl)methanone;
{2-Amino-4-[(4-(4-(trifluoromethyl)phenyl)piperazin-1-yl)methyl]thiophen-3-yl}[3-(trifluoromethyl)phenyl]methanone;
{2-Amino-4-[(4-(3-fluorophenyl)piperazin-1-yl)methyl]thiophen-3-yl}[3-(trifluoromethyl)phenyl]methanone;
{2-Amino-4-[(4-(2,6-difluorophenyl)piperazin-1-yl)methyl]thiophen-3-yl}[3-(trifluoromethyl)phenyl]methanone;
{2-Amino-4-[(4-(4-fluorophenyl)piperazin-1-yl)methyl]-5-methylthiophen-3-yl}(4-chlorophenyl)methanone;
{2-Amino-5-methyl-4-[(4-(4-phenylpiperazin-1-yl)methyl]thiophen-3-yl}(4-chlorophenyl)methanone;
{2-Amino-5-methyl-4-[(4-(4-(trifluoromethyl)phenyl)piperazin-1-yl)methyl]thiophen-3-yl}(4-chlorophenyl)methanone;
{2-Amino-4-[(4-(4-chlorophenyl)piperazin-1-yl)methyl]-5-methylthiophen-3-yl}(4-chlorophenyl)methanone;
{2-Amino-4-[(4-(4-bromophenyl)piperazin-1-yl)methyl]-5-methylthiophen-3-yl}(4-chlorophenyl)methanone;
{2-Amino-4-[(4-(4-iodophenyl)piperazin-1-yl)methyl]-5-methylthiophen-3-yl}(4-chlorophenyl)methanone;
{2-Amino-5-methyl-4-[(4-(4-nitrophenyl)piperazin-1-yl)methyl]thiophen-3-yl}(4-chlorophenyl)methanone;
4-{4-[(5-Amino-4-(4-chlorobenzoyl)-2-methylthiophen-3-yl)methyl]piperazin-1-yl}benzonitrile;
{2-Amino-4-[(4-benzylpiperazin-1-yl)methyl)-5-methylthiophen-3-yl](4-chlorophenyl)methanone;
{2-Amino-4-[(4-(4-methoxyphenyl)piperazin-1-yl)methyl]-5-methylthiophen-3-yl}(4-chlorophenyl)methanone;
{2-Amino-5-methyl-4-[(4-p-tolylpiperazin-1-yl)methyl]thiophen-3-yl}(4-chlorophenyl)methanone;

{2-Amino-4-[(4-(3,4-dichlorophenyl)piperazin-1-yl)methyl]-5-methylthiophen-3-yl}(4-chlorophenyl)methanone;

{2-Amino-5-methyl-4-[(4-(3-(trifluoromethyl)phenyl)piperazin-1-yl)methyl]thiophen-3-yl}(4-chlorophenyl)methanone;

{2-Amino-4-[(4-(3-chlorophenyl)piperazin-1-yl)methyl]-5-methylthiophen-3-yl}(4-chlorophenyl)methanone;

{2-Amino-4-[(4-(4-chloro-3-(trifluoromethyl)phenyl)piperazin-1-yl)methyl]-5-methylthiophen-3-yl}(4-chlorophenyl)methanone;

{2-Amino-4-[4-(4-fluorophenyl)piperazin-1-yl)methyl]-5-ethylthiophen-3-yl}(4-chlorophenyl)methanone;

{2-Amino-5-ethyl-4-[(4-phenylpiperazin-1-yl)methyl]thiophen-3-yl}(4-chlorophenyl)methanone;

{2-Amino-4-[(4-(4-chlorophenyl)piperazin-1-yl)methyl]-5-ethylthiophen-3-yl}(4-chlorophenyl)methanone; and {2-Amino-4-[(4-(3-fluorophenyl)piperazin-1-yl)methyl]-5-methylthiophen-3-yl}(4-chlorophenyl)methanone;

or a pharmaceutically acceptable salt thereof.

19. A pharmaceutical composition comprising a therapeutically effective amount of a compound of claim 1 in combination with one or more pharmaceutically acceptable carriers.

20. A pharmaceutical composition according to claim 19 for the treatment of pain, cardiac disease or disorder, neurological disease or injury, sleep disorder, epilepsy and depression.

21. A pharmaceutical composition according to claim 20, wherein the pain is neuropathic pain.

* * * * *